United States Patent [19]

Marfat

[11] Patent Number: 5,641,789
[45] Date of Patent: Jun. 24, 1997

[54] SULFONAMIDE DERIVATIVES OF BENZENEFUSED HYDROXY SUBSTITUTED CYCLOALKYL AND HETEROCYCLIC RING COMPOUNDS

[75] Inventor: Anthony Marfat, Mystic, Conn.

[73] Assignee: Pfizer Inc., New York, N.Y.

[21] Appl. No.: 416,681

[22] PCT Filed: Sep. 30, 1993

[86] PCT No.: PCT/US93/09171

§ 371 Date: Mar. 31, 1995

§ 102(e) Date: Mar. 31, 1995

[87] PCT Pub. No.: WO94/08996

PCT Pub. Date: Apr. 28, 1994

Related U.S. Application Data

[63] Continuation of PCT/US93/09171, Sep. 30, 1993, published as WO94/08996, Apr. 28, 1994, which is a continuation-in-part of Ser. No. 964,337, Oct. 21, 1992, abandoned.

[51] Int. Cl.⁶ .............. A61K 31/35; A61K 31/38; C07D 311/22; C07D 335/06

[52] U.S. Cl. .............. 514/314; 514/365; 514/367; 514/457; 546/172; 546/173; 548/146; 548/159; 549/23; 549/407

[58] Field of Search .............. 549/23, 407; 548/159, 548/146; 546/172, 173; 514/367, 365, 314, 457

[56] References Cited

U.S. PATENT DOCUMENTS 5,059,609  10/1991  Eggler ..................... 514/314
5,395,842   3/1995  Labrie ..................... 514/320

FOREIGN PATENT DOCUMENTS 0404440  12/1990  European Pat. Off. .

*Primary Examiner*—C. Warren Ivy
*Assistant Examiner*—D. Margaret M. Mach
*Attorney, Agent, or Firm*—Peter C. Richardson; Paul H. Ginsburg; Seymour G. Bekelnitzky

[57] ABSTRACT

Compounds of the formula

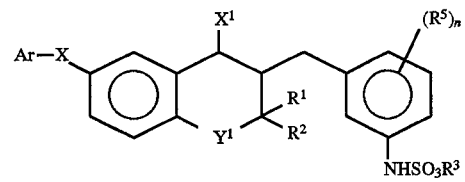

and pharmaceutically acceptable salts and prodrugs thereof, wherein $X^1$, Ar, X, $Y^1$, $R^1$, $R^2$, $R^3$, $R^5$ and n are defined below, which are inhibitors of the production of leukotrienes and/or blockers of leukotriene receptors, methods for preparing said compounds and intermediates useful in the preparation thereof, pharmaceutical compositions thereof methods of treatment therewith. The compounds of the above formula are useful in the prevention or treatment of asthma, arthritis, psoriasis, ulcers, myocardial infarction and related diseases in mammals.

11 Claims, No Drawings

SULFONAMIDE DERIVATIVES OF BENZENEFUSED HYDROXY SUBSTITUTED CYCLOALKYL AND HETEROCYCLIC RING COMPOUNDS

This application is a 371 of PCT/US93/09171, filed 30 Sep. 1993, published as WO94/08996, Apr. 28, 1994, which is a CIP of Ser. No. 07/964,337, filed 21 Oct. 1992, now abandoned.

BACKGROUND OF THE INVENTION

The present invention is directed to sulfonamide derivatives of benzenefused, hydroxy substituted alicyclic and heterocyclic compounds. The compounds inhibit the production of leukotrienes and/or block leukotriene receptors and are useful in the prevention or treatment of asthma, arthritis, psoriasis, ulcers, myocardial infarction and related disease states in mammals. The present invention is also directed to pharmaceutical compositions comprising said compounds, the use of the compounds in treatment of said disease states and intermediates useful in the synthesis of said compounds of the formula I.

U.S. Pat. No. 4,661,596, refers to compounds which are disubstituted naphthalenes, dihydronaphthalenes or tetralins having the formula

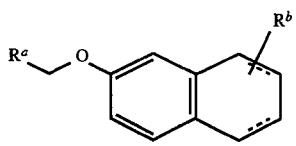

wherein the dotted lines represent optional double bonds, $R^a$ is 2-pyridyl, 2-quinolyl, 2-pyrazinyl, 2-quinoxalinyl, 2-thiazolyl, 2-benzothiazolyl, 2-oxazolyl, 2-benzoxazolyl, 1-alkyl-2-imidazolyl or 1-alkyl-2-benzimidazolyl and $R^b$ is hydroxy, lower alkoxy, lower alkyl or perfluoro alkyl.

U.S. Pat. No. 5,059,609 refers to substituted tetralins, chromans and related compounds.

The compounds of these patents are alleged to inhibit lipoxygenase enzyme and antagonize the effects of leukotriene D4 and, therefore, to be useful in the prevention and treatment of asthma.

The chemical nomenclature employed herein generally follows that of "I.U.P.A.C. Nomenclature of Organic Chemistry, 1979 Edition," Pergammon Press, New York, 1979.

SUMMARY OF THE INVENTION

The present invention is directed to racemic or optically active compounds having the structural formula

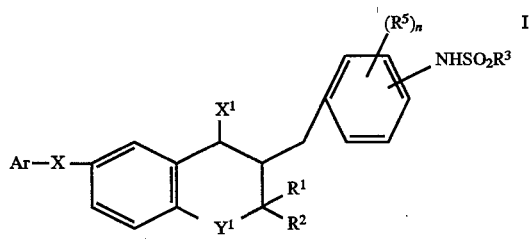

wherein $X^1$ is hydrogen or OH:

Ar is an optionally substituted 5-8 membered heteroaryl or optionally substituted benzene fused optionally substituted heteroaryl ring wherein said heteroaryl ring comprises 1 to 4 heteroatoms selected from nitrogen, oxygen and sulfur;

X is selected from the group consisting of $CH_2O$, $CH_2$—$CH_2$, $CH$=$CH$, $C$≡$C$, $CH_2S$, $CH_2SO_2$ and $CH_2SO$;

$Y^1$ is selected from the group consisting of O, $CH_2$, S, SO, $SO_2$ and $NR^6$;

$R^1$ and $R^2$ are each independently selected from hydrogen and optionally substituted ($C_1$-$C_6$)alkyl;

$R^3$ is selected from the group consisting of optionally substituted ($C_3$-$C_6$) cycloalkyl-($C_1$-$C_6$)alkyl, optionally halogenated ($C_1$-$C_6$)alkyl and optionally substituted aryl wherein the substituents are selected from the group consisting of optionally halogenated ($C_1$-$C_6$) alkyl, halogen, nitro, carboxyl, N-disubstituted carboxamide, and ($C_1$-$C_6$)alkoxy;

$R^5$ is selected from the group consisting of ($C_1$-$C_6$) alkoxy, ($C_1$-$C_6$)alkyl and halogen, $NO_2$, $CO_2R$ and $CONR_2$; wherein each R is independently selected from the group consisting of hydrogen, optionally substituted ($C_1$-$C_6$)alkyl, cycloalkyl-($C_1$-$C_6$) alkyl, aryl($C_1$-$C_6$)alkyl and optionally substituted aryl.

$R^6$ is hydrogen or ($C_1$-$C_4$)alkyl; and n is 0 or an integer between 1 and 4;

and pharmaceutically acceptable salts and prodrugs thereof, Because of their ease of preparation and valuable biological activity, in the preferred compounds of the formula I, $R^1$ and $R^2$ are each hydrogen, X is $CH_2O$, Ar is 2-, 3- or 4-pyridyl, quinol-2-yl, 7-chloroquinol-2-yl, 6-fluoroquinol-2-yl, 5-fluorobenzothiazol-2-yl, 5,6-difluorobenzothiazol-2-yl, 5-cyclobutylbenzothiazol-2-yl, 4-isopropylthiazol-2-yl, 4-cyclobutylthiazol-2-yl or pyrazin-2-yl or $R^3$ is trifluoromethyl, 4-methoxyphenyl, 3-methoxycarbonylphenyl, 4-methoxycarbonylphenyl, 3-carboxyphenyl, 4-carboxyphenyl, pyrid-2-yl or pyrid-3-yl, optionally halogenated ($C_1$-$C_6$)alkyl or optionally substituted ($C_6$-$C_{10}$)aryl wherein said substitutents are selected from the group consisting of halo, nitro, ($C_1$-$C_6$)alkyl and ($C_1$-$C_6$)alkoxy.

Preferred compounds of formula I are those wherein $Y^1$ is O, S, $NR^{10}$ or $CH_2$, wherein $R^6$ is defined above;

Most preferred are racemic or optically active compounds having the relative stereochemical formulae

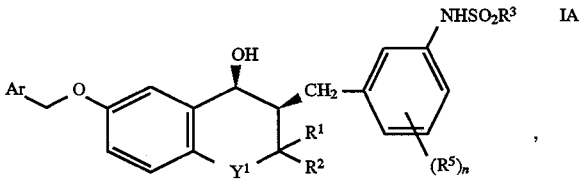

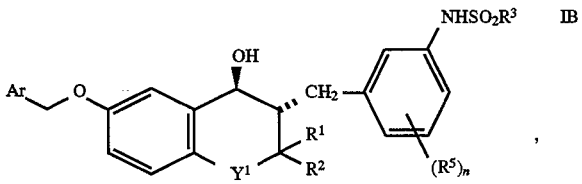

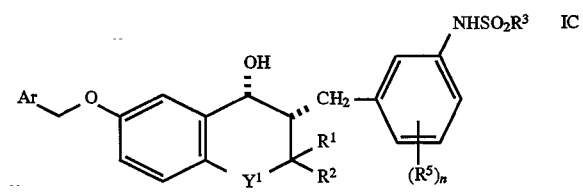

-continued
or

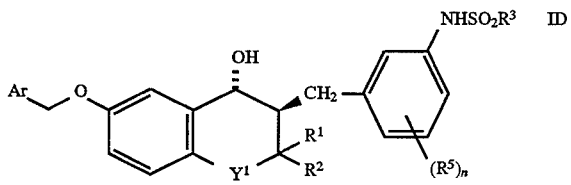

wherein $R^1$, $R^2$, $R^3$, $R^5$, $Y^1$, Ar and n are as described above, most particularly those racemic or optically active compounds of formulae IA, IB, IC and ID wherein Ar is quinol-2-yl, 7-chloroquinol-2-yl, 6-fluoroquinol-2-yl, 5-fluorobenzothiazol-2-yl, or 5,6-difluorobenzothiazol-2-yl, 4-isopropylthiazol-2-yl, or 4-cyclobutylthiazol-2-yl and $R^3$ is trifluoromethyl.

Pharmaceutically-acceptable acid addition salts include, but are not limited to, those with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic acid and succinic acid. In the case of those compounds of the formula I which contain a further basic nitrogen, it will, of course, be possible to form diacid addition salts (e.g., the dihydrochloride) as well as the usual monoacid addition salt. Pharmaceutically-acceptable cationic salts include, but are not limited to, those of sodium, potassium, calcium, magnesium, ammonium, N,N'-dibenzylethylenediamine, N-methylglucamine (meglumine), ethanolamine and diethanolamine.

The 4-hydroxy group of the chromanol; 1,2,3,4-tetrahydro-quinoline or isoquinoline; or 2,3-dihydrobenzothiopyran group or the α-hydroxy group of the tetralol may comprise an acyloxy or alkoxy group which is hydrolyzed to a hydroxy group, or the sulfonamide may comprise a disulfonimide which is hydrolyzed to form a sulfonamide under physiological conditions. They are esters, ethers and disulfonimides of a type which are frequently referred to as "pro-drugs." Such esters, ethers and disulfonimides are now as well-known and common in the medicinal art as pharmaceutically-acceptable salts. The esters are generally used to enhance oral absorption, but in any event are readily hydrolyzed in vivo to the parent hydroxy compound. The more preferred acyloxy groups are those in which the acyl moiety is the alpha-aminoacyl residue of a naturally occurring L-alpha-amino acid, e.g.,

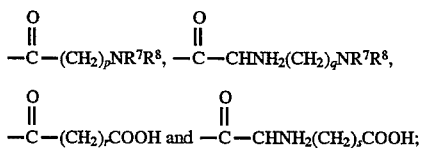

wherein
$R^7$ and $R^8$ are taken separately and are each independently hydrogen or $(C_1-C_4)$alkyl, or $R^7$ and $R^8$ are taken together with the nitrogen to which they are attached to form a pyrrolidine, piperidine, perhydroazepin or morpholine ring;
p is an integer from 1 to 4;
q is an integer from 1 to 3;
r is an integer from 2 to 3; and
s is an integer from 1 to 3.

Preferred compounds of the formula I are selected from the group consisting of:
cis-(±)-N-[3-(6-(5-fluorobenzothiazol-2ylmethoxy)-4-hydroxy-chroman-3-ylmethyl)phenyl]trifluoromethanesulfonamide;
cis-(+)-N-[3-(6-(5-fluorobenzothiazol-2ylmethoxy)-4-hydroxy-chroman-3-ylmethyl)phenyl]trifluoromethanesulfonamide;
cis-(−)-N-[3-(6-(5-fluorobenzothiazol-2ylmethoxy)-4-hydroxy-chroman-3-ylmethyl)phenyl]trifluoromethanesulfonamide;
cis-(±)-N-(3-[6-(5,6-difluorobenzothiazol-2-ylmethoxy)-4-hydroxy-chroman-3-ylmethyl)-phenyl]-trifluoromethanesulfonamide;
cis-(+)-N-[3-(6-(5,6-difluorobenzothiazol-2-ylmethoxy)-4-hydroxy-chroman-3-ylmethyl)phenyl]trifluoromethanesulfonamide;
cis-(−)-N-[3-(6-(5,6-difluorobenzothiazol-2-ylmethoxy)-4-hydroxy-chroman-3-ylmethyl)phenyl]trifluoromethanesulfonamide;
cis-(±)-N-[3-(6-(7-chloroquinolin-2-ylmethoxy)-4-hydroxy-chroman-3-ylmethyl)phenyl]trifluoromethanesulfonamide;
cis-(+)-N-[3-(6-(7-chloroquinolin-2-ylmethoxy)-4-hydroxy-chroman-3-ylmethyl)phenyl]trifluoromethanesulfonamide;
cis-(−)-N-[3-(6-(7-chloroquinolin-2-ylmethoxy)-4-hydroxy-chroman-3-ylmethyl)phenyl]trifluoromethanesulfonamide;
cis-(±)-N-[3-(6-(4-isopropylthiazol-2-ylmethoxy)-4-hydroxy-chroman-3-ylmethyl)phenyl]trifluoromethansulfonamide;
cis-(+)-N-[3-(6-(4-isopropylthiazol-2-ylmethoxy)-4-hydroxy-chroman-3-ylmethyl)phenyl]trifluoromethansulfonamide;
cis-(−)-N-[3-(6-(4-isopropylthiazol-2-ylmethoxy)-4-hydroxy-chroman-3-ylmethyl)phenyl]trifluoromethansulfonamide;
cis-(±)-N-[3-(6-(4-cyclobutylthiazol-2-ylmethoxy)-4-hydroxy-chroman-3-ylmethyl)phenyl]trifluoromethansulfonamide;
cis-(+)-N-[3-(6-(4-cyclobutylthiazol-2-ylmethoxy)-4-hydroxy-chroman-3-ylmethyl)phenyl]trifluommethansulfonamide;
cis-(−)-N-[3-(6-(4-cyclobutylthiazol-2-ylmethoxy)-4-hydroxy-chroman-3-ylmethyl)phenyl]trifluoromethansulfonamide;
cis-(±)-N-(3-[6-(6-fluoroquinolin-2-ylmethoxy)-4-hydroxy-chroman-3-ylmethyl)phenyl]-trifluoroomethanesulfonamide;
cis-(+)-N-(3-[6-(6-fluoroquinolin-2-ylmethoxy)-4-hydroxy-chroman-3-ylmethyl)phenyl]-trifluoromethanesulfonamide;
cis-(−)-N-(3-[6-(6-fluoroquinolin-2-ylmethoxy)-4-hydroxy-chroman-3-ylmethyl)phenyl]-trifluoromethanesulfonamide;
cis-(±)-N-(3-[6-(quinolin-2-ylmethoxy)-4-hydroxy-chroman-3-ylmethyl)-phenyl]-trifluoromethanesulfonamide;
cis-(+)-N-(3-[6-(quinolin-2-ylmethoxy)-4-hydroxy-chroman-3-ylmethyl)-phenyl]-trifluoromethanesulfonamide;
cis-(−)-N-(3-[6-(quinolin-2-ylmethoxy)-4-hydroxy-chroman-3-ylmethyl)-phenyl]-trifluoromethanesulfonamide;
cis-(±)-N-(3-(7-((5-fluorobenzothiazol-2ylmethoxy)-1-hydroxy-1,2,3,4-tetrahydronaphthalen-2-ylmethyl)phenyl]-trifluoromethanesulfonamide;
cis-(+)-N-(3-(7-((5-fluorobenzothiazol-2ylmethoxy)-1-hydroxy-1,2,3,4-tetrahydronaphthalen-2-ylmethyl)phenyl]-trifluoromethanesulfonamide;
cis-(−)-N-(3-(7-((5-fluorobenzothiazol-2ylmethoxy)-1-hydroxy-1,2,3,4-tetrahydronaphthalen-2-ylmethyl)phenyl]-trifluoromethanesulfonamide;

cis-(±)-C,C,C-Trifluoro-N,N-{3-[6-(5-fluorobenzothiazol-2-ylmethoxy)-4-hydroxy-trans-2-methylchroman-3-ylmethyl]phenyl}-methanesulfonamide;

cis-(+)-C,C,C-Trifluoro-N-{3-[6-(5-fluorobenzothiazol-2-ylmethoxy)-4-hydroxy-trans-2-methylchroman-3-ylmethyl]-phenyl}methanesulfonamide;

cis-(−)-C,C,C-Trifluoro-N-{3-[6-(5-fluorobenzothiazol-2-ylmethoxy)-4-hydroxy-trans-2-methylchroman-3-ylmethyl]phenyl}methanesulfonamide;

cis-(+)-N-{3-[6-(7-Chloroqinolin-2-ylmethoxy)-4-hydroxychroman-3-ylmethyl]-4-methoxyphenyl}-C,C,C-trifluoromethanesulfonamide;

cis-(−)-N-{3-[6-(7-Chloroqinolin-2-ylmethoxy)-4-hydroxychroman-3-ylmethyl]-4-methoxyphenyl}-C,C,C-trifluoromethanesulfonamide;

cis-(+)-N-{3-[6-(5,6-Difluorobenzothiazol-2-ylmethoxy)-4-hydroxychroman-3-ylmethyl]-4-methoxyphenyl}-C,C,C-trifluoromethanesulfonamide;

cis-(+)-N-{3-[6-(5,6-Difluorobenzothiazol-2-ylmethoxy)-4-hydroxychroman-3-ylmethyl]-4-methoxyphenyl}-C,C,C-trifluoromethanesulfonamide;

cis-(±)-N-{3-[6-(7-Chloroqinolin-2-ylmethoxy)-1-hydroxyindan-2-ylmethyl]phenyl}-C,C,C-trifluoromethanesulfonamide;

cis-(+)-N-{3-[6-(4-Cyclobutylthiazol-2-ylmethoxy)-4-hydroxychroman-3-ylmethyl]-4-methoxyphenyl}-C,C,C-trifluoromethanesulfonamide;

cis-(−)-N-{3-[7-(5,6-Difluorobenzothiazol-2-ylmethoxy)-1-hydroxy-1,2,3,4-tetrahydronapth-2-ylmethyl]-phenyl}-C,C,C-trifluoromethanesulfonamide;

cis-(−)-N-{3-[7-(7-Chloroqinolin-2-ylmethoxy)-1-hydroxy-1,2,3,4-tetrahydronapth-2-ylmethyl]-phenyl}-C,C,C-trifluoromethanesulfonamide;

cis-(+)-N-{3-[7-(7-Chloroqinolin-2-ylmethoxy)-1-hydroxy-1,2,3,4-tetrahydronapth-2-ylmethyl]-phenyl}-C,C,C-trifluoromethanesulfonamide;

cis-(+)-N-{3-[7-(5,6-Difluorobenzothiazol-2-ylmethoxy)-1-hydroxy-1,2,3,4-tetrahydronapth-2-ylmethyl]-phenyl}-C,C,C-trifluoromethanesulfonamide;

cis-(−)-N-{3-[7-(7-Chloroqinolin-2-ylmethoxy)-1,2,3,4-tetrahydronapth-2-ylmethyl]phenyl}-C,C,C-trifluoromethanesulfonamide;

cis-(+)-N-{3-[7-(7-Chloroqinolin-2-ylmethoxy)-1,2,3,4-tetrahydronapth-2-ylmethyl]phenyl}-C,C,C-trifluromethanesulfonamide;

cis-(+)-C,C,C-Trifluoro-N-{3-[7-(6-fluoroqinolin-2-ylmethoxy)-1-hydroxy-1,2,3,4-tetrahydronapth-2-ylmethyl]-phenyl}-methanesulfonamide;

cis-(+)-N-{3-[7-(4-Cyclobutylthiazol-2-ylmethoxy)-1-hydroxy-1,2,3,4-tetrahydronapth-2-ylmethyl]-phenyl}-C,C,C-trifluoromethanesulfonamide;

cis-N-{3-[6-(5,6-Difluorobenzothiazol-2-ylmethoxy)-chroman-3-ylmethyl]-phenyl}-C,C,C-trifluoromethanesulfonamide;

cis-N-{3-[6-(7-Chloroqinolin-2-ylmethoxy)-chroman-3-ylmethyl]-phenyl}-C,C,C-trifluoromethanesulfonamide;

cis-(±)-N-{4-Chloro-3-[6-(7-chloroqinolin-2-ylmethoxy)-4-hydroxychroman-3-ylmethyl]-phenyl}-C,C,C-trifluoromethanesulfonamide;

cis-(+)-N-{4-Chloro-3-[6-(7-chloroqinolin-2-ylmethoxy)-4-hydroxychroman-3-ylmethyl]-phenyl}-C,C,C-trifluoromethanesulfonamide;

cis-(±)-N-{4-Chloro-3-[6-(5,6-difluorobenzothiazol-2-ylmethoxy)-4-hydroxychroman-3-yl-methyl]phenyl}-C,C,C-trifluoromethanesulfonamide;

cis-N-{3-[6-(5,6-Difluorobenzothiazol-2-ylmethoxy)-4-hydroxy-trans-2-methylchroman-3-ylmethyl]-phenyl}-C,C,C-trifluoromethanesulfonamide;

cis-(±)-N-{3-[6-(5,6-Difluorobenzothiazol-2-ylmethoxy)-4-hydroxy-2,2-dimethylchroman-3-yl]-phenyl}C,C,C-trifluoromethanesulfonamide;

cis-(+)-N-{3-[6-(5,6-Difluorobenzothiazol-2-ylmethoxy)-4-hydroxy-2,2-dimethylchroman-3-yl]phenyl}-C,C,C-trifluoromethanesulfonamide;

cis-(−)-N-{3-[6-(5,6-Difluorobenzothiazol-2-ylmethoxy)-4-hydroxy-2,2-dimethylchroman-3-yl]phenyl}-C,C,C-trifluoromethanesulfonamide;

cis-(+)-N-{4-Chloro-3-[6-(5,6-difluorobenzothiazol-2-ylmethoxy)-4-hydroxychroman-3-yl-methyl]phenyl}-C,C,C-trifluoromethanesulfonamide;

cis-(−)-N-{4-Chloro-3-[6-(5,6-difluorobenzothiazol-2-ylmethoxy)-4-hydroxychroman-3-yl-methyl]phenyl}-C,C,C-trifluoromethanesulfonamide;

cis-(+)-N-{4-Chloro-3-[6-(5,6-difluorobenzothiazol-2-ylmethoxy)-4-hydroxy-2,2-dimethyl-chroman-3-ylmethyl]-phenyl}-C,C,C-trifluoromethanesulfonamide;

cis-(±)-N-{4-Chloro-3-[7-(5,6-difluorobenzothiazol-2-ylmethoxy)-1-hydroxy-1,2,3,4-tetrahydronaphth-2-ylmethyl]-phenyl}-C,C,C-trifluoromethanesulfonamide;

cis-(+)-N-{4-Chloro-3-[7-(5,6-difluorobenzothiazol-2-ylmethoxy)-1-hydroxy-1,2,3,4-tetrahydronaphth-2-ylmethyl]-phenyl}-C,C,C-trifluoromethanesulfonamide;

cis-(±)-N-{3-[6-(5,6-Difluorobenzothiazol-2-ylmethoxy)-1-hydroxyindan-2-ylmethyl]-phenyl}-C,C,C-trifluoromethanesulfonamide;

cis-(+)-N-{3-[6-(5,6-Difluorobenzothiazol-2-ylmethoxy)-1-hydroxyindan-2-ylmethyl]-phenyl}-C,C,C-trifluoromethanesulfonamide;

cis-(−)-N-{3-[6-(5,6-Difluorobenzothiazol-2-ylmethoxy)-1-hydroxyindan-2-ylmethyl]phenyl}-C,C,C-trifluoromethanesulfonamide;

cis-N-{3-[6-(5,6-Difluorobenzothiazol-2-ylmethoxy)-2,2-dimethyl-2H-chromen-3-ylmethyl]-4-methoxyphenyl}-C,C,C-trifluoromethanesulfonamide;

cis-N-{3-[6-(7-Chloroqinolin-2-ylmethoxy)-4-hydroxy-chorman-3-ylmethyl]-4-methoxyphenyl}-C,C,C-trifluoromethanesulfonamide;

cis-(±)-N-{3-[6-(5,6-Difluorobenzothiazol-2-ylmethoxy)-4-hydroxy-2,2-dimethylchroman-3-ylmethyl]-4-methoxyphenyl}-C,C,C-trifluoromethanesulfonamide;

cis(+)-N-{3-(5,6-Difluorobenzothiazol-2-ylmethoxy)-4-hydroxy-2,2-dimethylchroman-3-ylmethyl]-4-methoxyphenyl}-C,C,C-trifluoromethanesulfonamide;

cis-N-{3-[6-(7-Chloroqinolin-2-ylmethoxy)-4-hydroxychroman-3-ylmethyl]-4-hydroxyphenyl}-C,C,C-trifluoromethanesulfonamide;

cis-N-{3-[6-(7-Chloroquinolin-2-ylmethoxy)-4-hydroxychroman-3-ylmethyl]-4-hydroxyphenyl}-C,C,C-trifluoromethanesulfonamide;

cis-N-{3-[6-(5,6-Difluorobenzothiazol-2-ylmethoxy)-4-hydroxychroman-3-ylmethyl]-4-methoxyphenyl}-C,C,C-trifluoromethanesulfonamide;

cis-N-{3-[6-(5,6-Difluorobenzothiazol-2-ylmethoxy)-4-hydroxy-2,2-dimethylchroman-3-ylmethyl]-4-methoxyphenyl}-C,C,C-trifluoromethanesulfonamide; and cis-3-[6-(5,6-Difluorobenzothiazol-2-ylmethoxy)-4-hydroxy-2,2-dimethylchroman-3-ylmethyl]-4-methoxybenzoic acid.

The present invention is also directed to valuable intermediate compounds having the structural formula

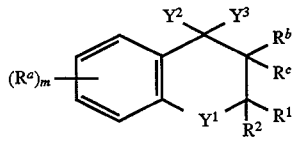

IV wherein $R^1$, $R^2$ and n are defined as above;

$Y^1$ is O, S, $NR^6$ or $CH_2$; and m is an integer from 1 to 4 a) in a first alternative $Y^2$ and $Y^3$ are taken together and form a carbonyl group, or $Y^2$ and $Y^3$ are taken separately, and $Y^2$ is hydrogen and $Y^3$ is hydroxy;

$R^a$ is hydroxy or benzyloxy;

$R^b$ and $R^c$ are taken separately and $R^b$ is hydrogen and $R^c$ is

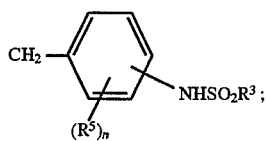

and $R^3$, $R^5$ and n are defined as above;

or b) in a second alternative $R^b$ and $R^c$ are taken together and are hydroxymethylene or diazo; or $R^b$ and $R^c$ are taken separately, $R^b$ is hydrogen and $R^c$ is

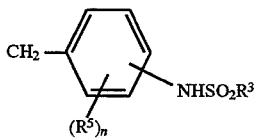

and $R^a$ is hydroxy or

wherein $R^9$ is hydrogen, $(C_1-C_6)$alkyl, phenyl or a value of Ar as defined above and $R^3$, $R^5$, and n are defined as above.

Preferred compounds of the formula IV are those wherein $R^a$ is Ar, $Y^1$ is $CH_2$, $NR^6$, S or O wherein $R^6$ is defined as above, $R^1$, $R^2$, $R^5$ and $R^b$ are each hydrogen, n is 0, m is 1, $R^c$ is

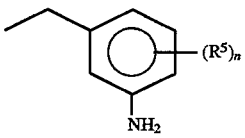

and Ar is selected from the group consisting of 7-chloroquinol-2-yl, 5,6-difluorobenzothiazol-2-yl, 6-fluoroquinol-2-yl, quinol-2-yl, 5-fluorobenzothiazol-2-yl, 4-isopropylthiazol-2-yl and 4-cyclobutylthiazol-2-yl.

Most preferred compounds of the formula IV are selected from the group consisting of (+) 3-[(3-aminophenyl)methyl]-6-[(7-chloroquinol-2-yl)methoxy]-4-chromanol;

(+) 3-[(3-aminophenyl)methyl]-6-[(5,6-difluorobenzothiazol-2-yl)methoxy]-4-chromanol;

(+) 3-[(3-aminophenyl)methyl]-6-[(6-fluoroquinol-2-yl)methoxy]-4-chromanol;

(+) 3-[(3-aminophenyl)methyl]-6-[(quinol-2-yl)methoxy]-4-chromanol;

(+) 3-[(3-aminophenyl)methyl]-6-[(5-fluorobenzothiazol-2-yl)methoxy]-4-chromanol;

(+) 3-[(3-aminophenyl)methyl]-6-[(4-cyclobutylthiazol-2-yl)-methoxy]-4-chromanol;

(+) 3-[(3-aminophenyl)methyl]-6-[(4-isopropylthiazol-2-yl)-methoxy]-4-chromanol;

(+) 2-[(3-aminophenyl)methyl]-7-[(7-chloroquinol-2-yl)methoxy]-α-tetralol;

(+) 2-[(3-aminophenyl)methyl]-7-[(5,6-difluorobenzothiazol-2-yl)methoxy]-α-tetralol;

(+) 2-[(3-aminophenyl)methyl]-7-[(6-fluoroquinol-2-yl)methoxy]-α-tetralol;

(+) 2-[(3-aminophenyl)methyl]-7-[(quinol-2-yl)methoxy]-α-tetralol;

(+) 2-[(3-aminophenyl)methyl]-7-[(5-fluorobenzothiazol-2-yl)methoxy]-α-tetralol;

(+) 2-[(3-aminophenyl)methyl]-7-[(4-cyclobutylthiazol-2-yl)methoxy]-α-tetralol;

(+) 2-[(3-aminophenyl)methyl]-7-[(4-isopropylthiazol-2-yl)methoxy]-α-tetralol;

(+) 3-(3-benzyloxycarbonylaminobenzyl)-4,6-chromandiol;

(+) 3-(3-aminobenzyl)-4,6-chromandiol;

(+) 2-(3-benzyloxycarbonylamino-benzyl)-1,7-dihydroxytetralin;

and (+) 2-(3-aminobenzyl)-1,7-dihydroxytetralin.

Other preferred compounds of the formula IV are those wherein $Y^1$, $R^1$, $R^2$, $R^5$, $R^b$ and $R^c$, n and m are as defined above and $R^a$ is OH.

Yet other preferred compounds of the formula IV are those wherein $Y^1$, $R^1$, $R^2$, $R^5$, $R^b$, n and m are defined as above $R^a$ is OH and $R^c$ is

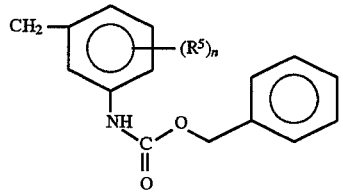

Also forming a part of the present invention are pharmaceutical compositions for administration to a mammal (including a human) which comprise a compound of the formula I or a pharmaceutically acceptable salt or prodrug thereof (hereinafter referred to as the active compounds of the present invention) and a pharmaceutically acceptable carrier; and a method of inhibiting leukotriene production and/or blocking leukotriene D4 receptors in a mammal so as to prevent or treat asthma (particularly in man), arthritis, psoriasis, ulcers, or myocardial infarction comprising administering to said mammal an asthma, arthritis, psoriasis, ulcers and myocardial infarction treating amount of a compound according to claim 1.

As used herein, halogen includes fluoro, chloro, bromo and iodo. Unless otherwise indicated, the alkyl group referred to herein, as well as the alkyl portions of other groups (e.g., alkoxy), wherein said alkyl group comprises more than two carbon atoms, may be straight chain, branched or cyclic or may have both straight chain and cyclic or branched and cyclic portions.

DETAILED DESCRIPTION OF THE INVENTION

The compounds of the present invention are readily prepared, according to Scheme 1, where the symbols $R^1$, $R^2$, $R^3$, $R^5$, $R^9$, n and Ar are defined as above.

The condensation of compound 1 with compound 2, in Scheme 1, is typically carried out with the phenolic group of the chromanone or tetralone protected by a group $R^9$—$CH_2$. The methyl and benzylic groups are a preferred protecting groups. The preferred conditions employ a molar excess of the required aldehyde in a molar excess of a secondary amine such as pyrrolidine or piperidine as base. (It is understood that such a base facilitates the condensation by forming an enamine intermediate.)

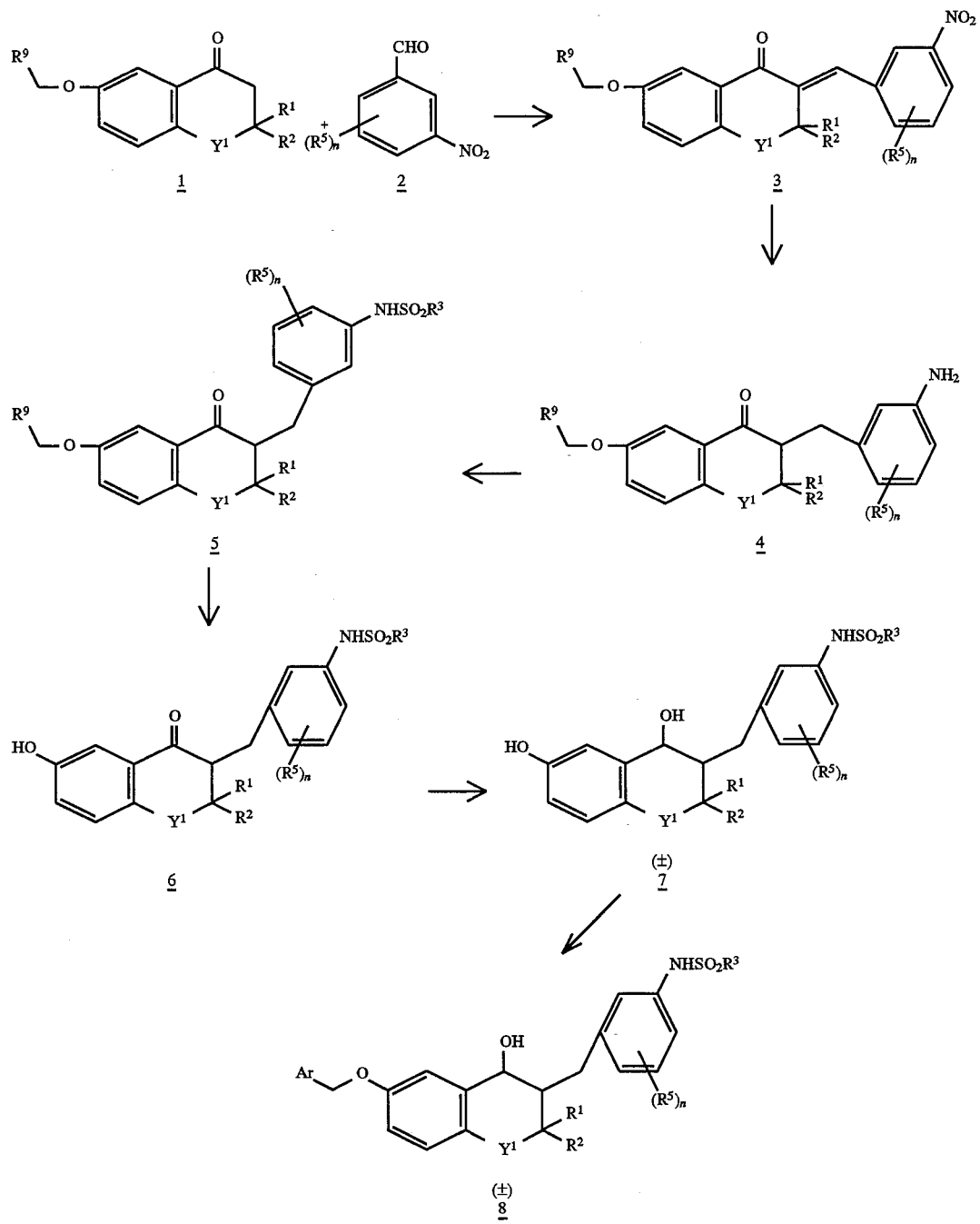

Scheme 1

Scheme 2
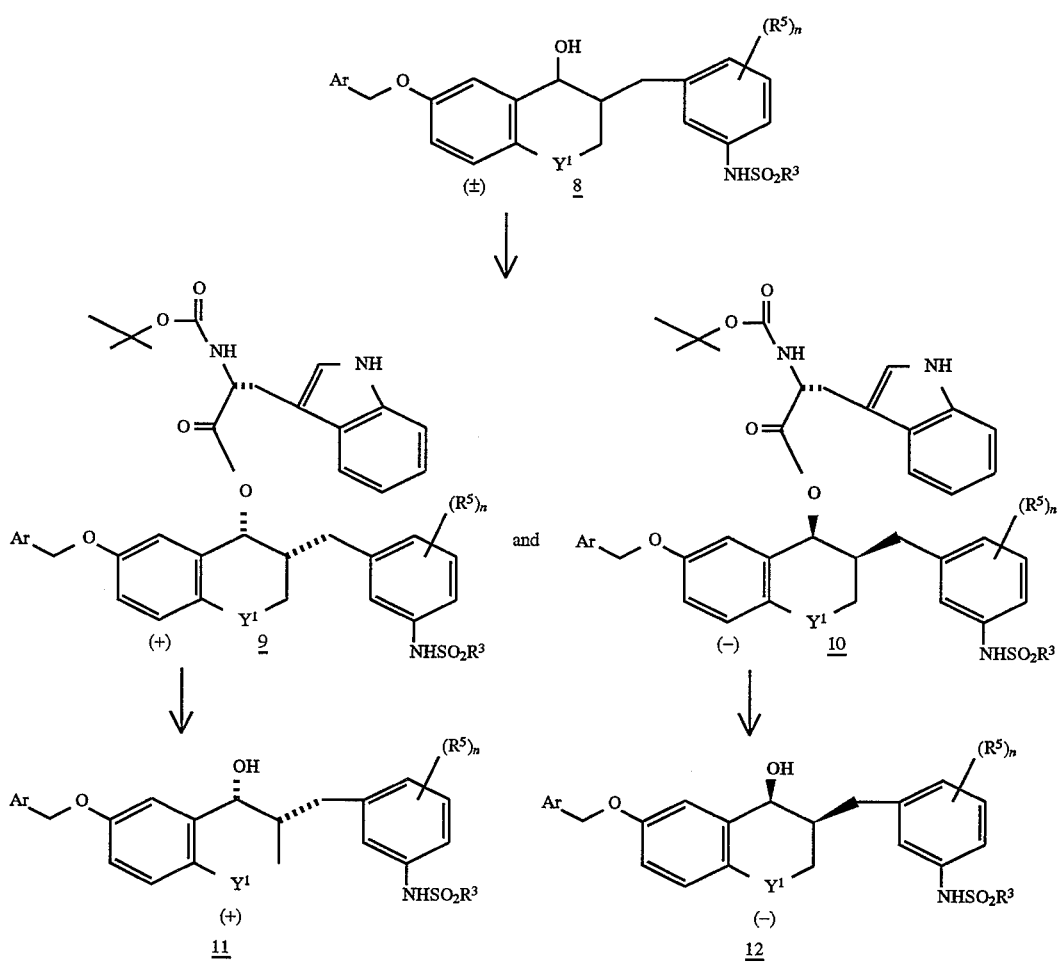
Scheme 3
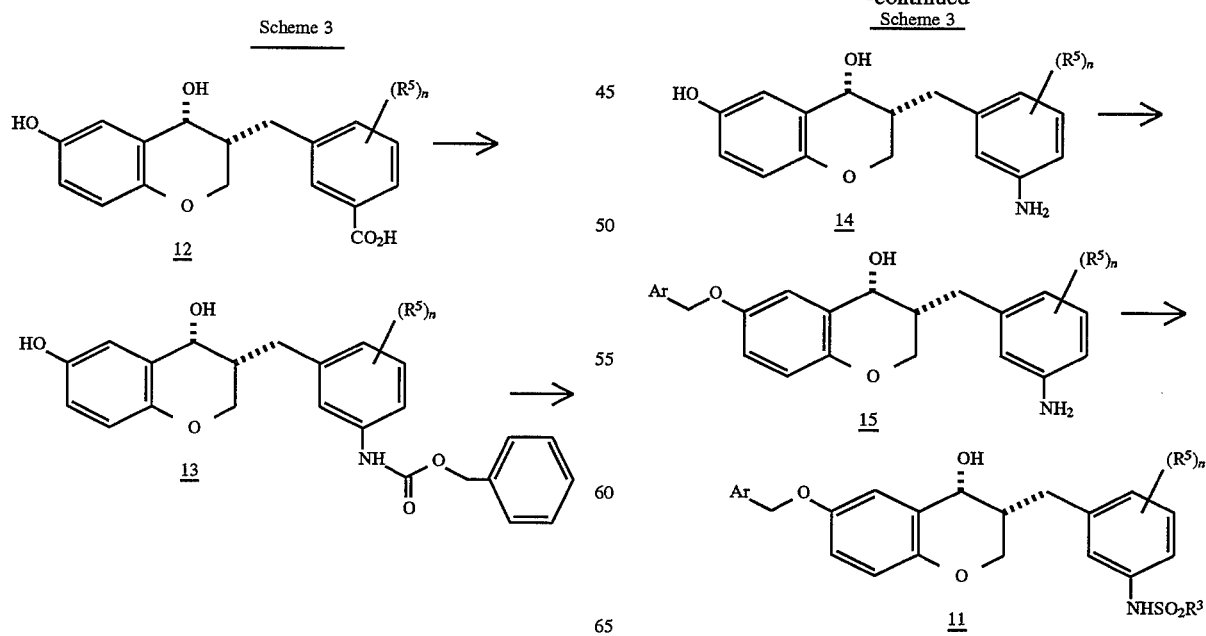

Scheme 4
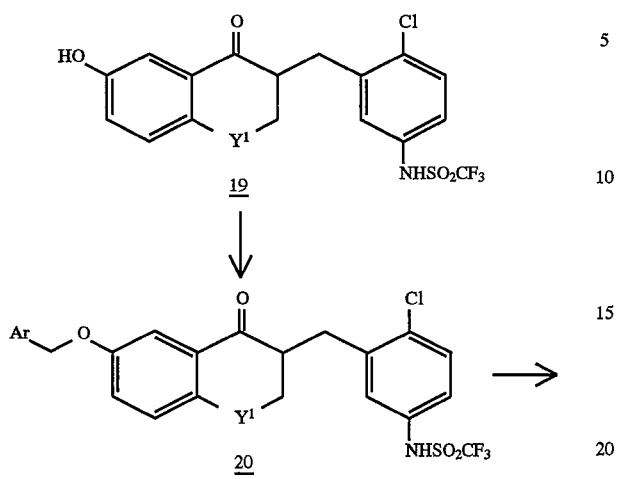
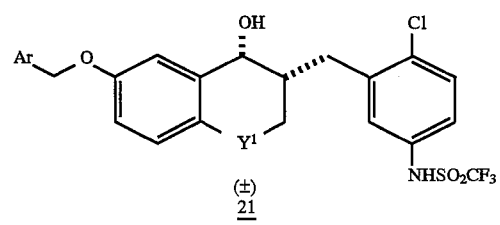
Scheme 5
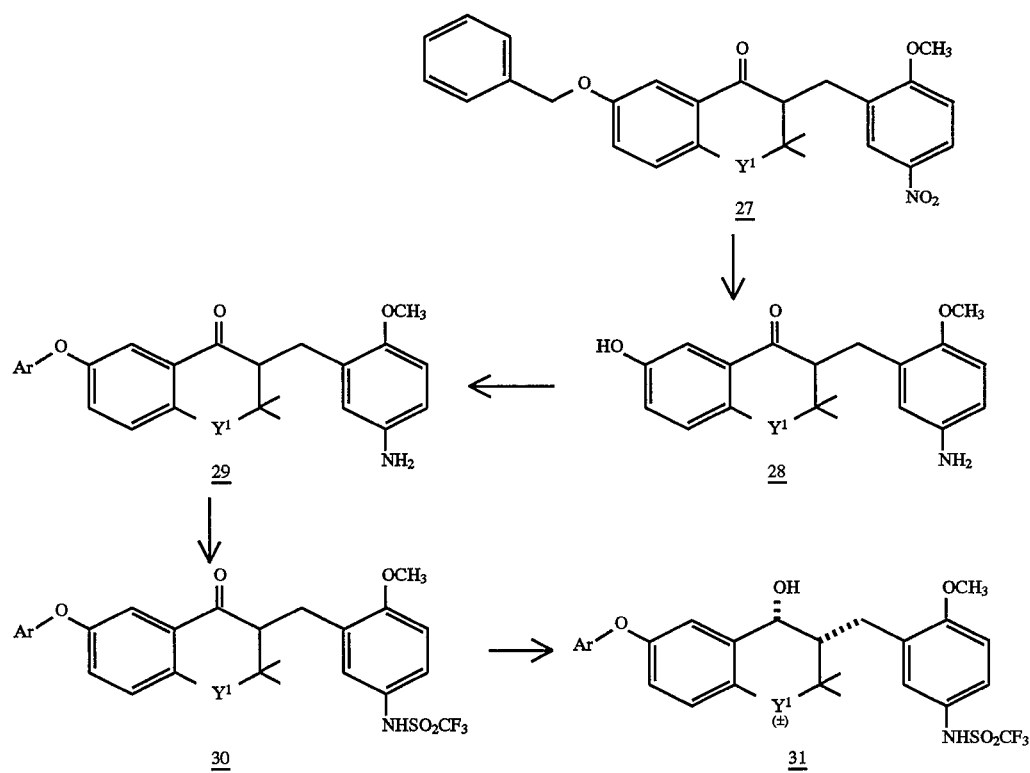

Scheme 6
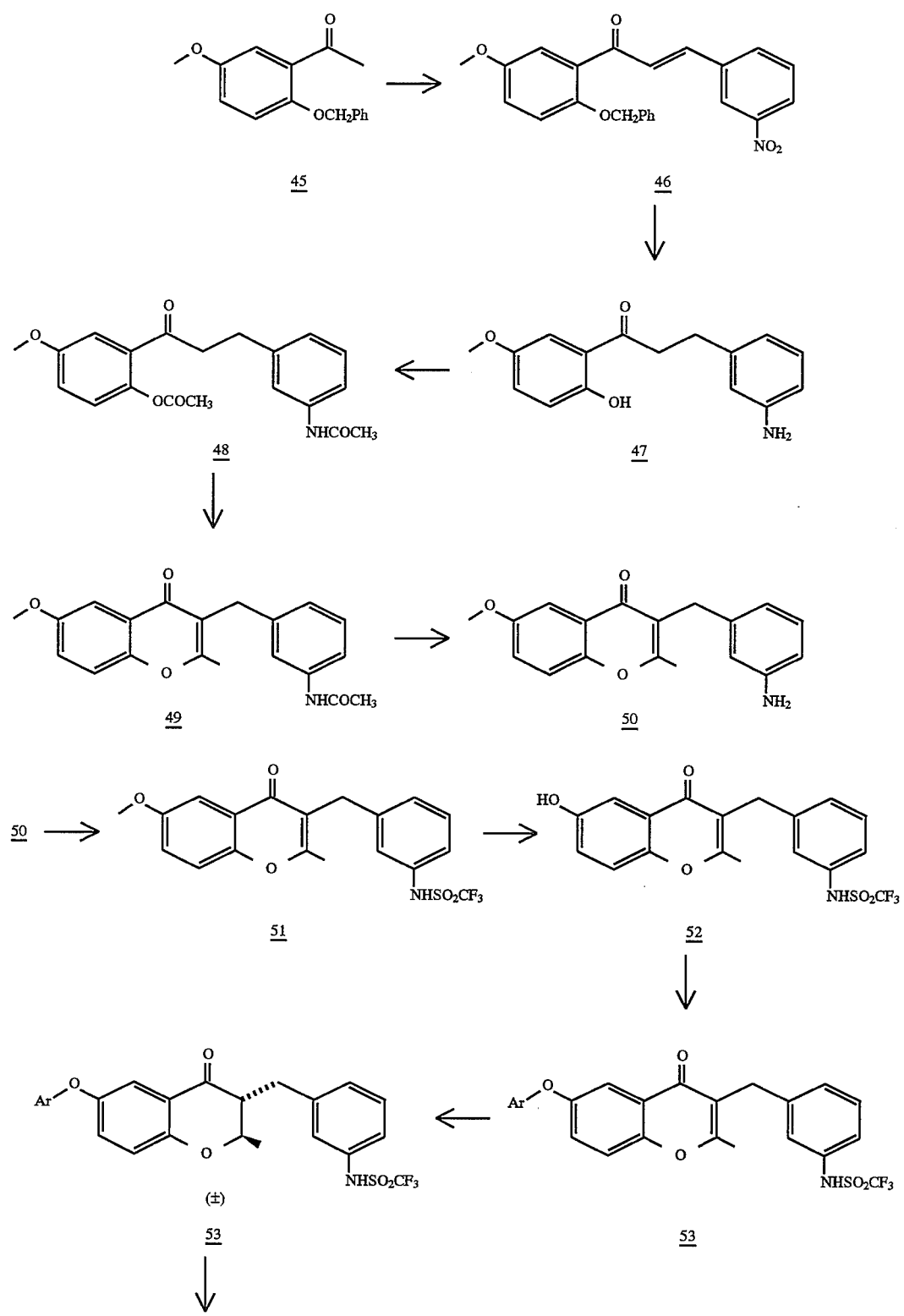

-continued
Scheme 6

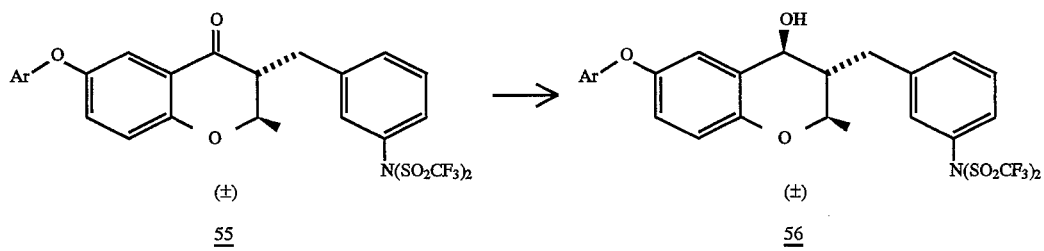

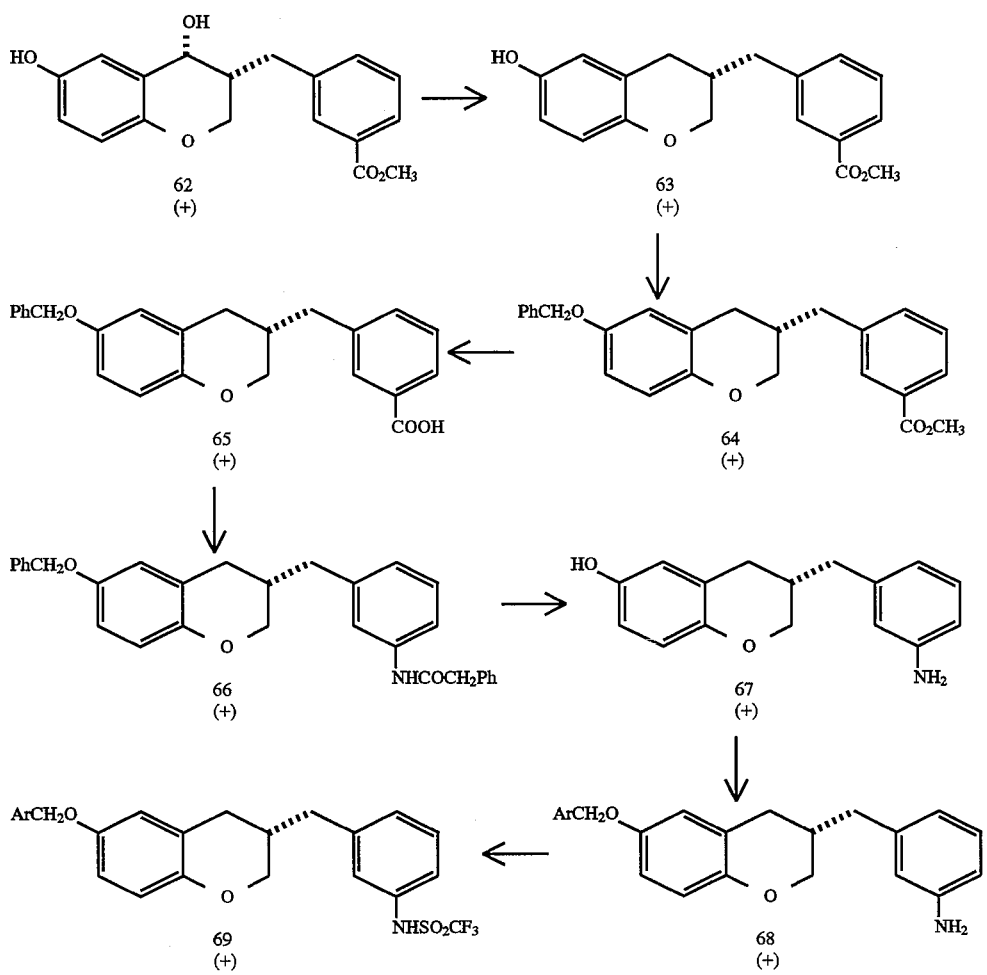

The reaction is generally carried out in a reaction-inert solvent, lower alcohols such as methanol being particularly well suited for this purpose. The temperature conditions for this transformation are not critical, e.g., about 0° to 70° C. is generally satisfactory, with ambient temperature particularly well suited as a matter of convenience.

As used here and elsewhere herein, the expression "reaction-inert solvent" refers to a solvent which does not interact with starting materials, reagents, intermediates or products in a manner which adversely affects the yield of the desired product.

The catalytic hydrogenation transformations (e.g., hydrogen addition to the double bond and reduction of the nitro group in compound 3, of Scheme 1 ) are carried out under conventional conditions, generally in a reaction-inert solvent, and preferably using a noble metal catalyst and moderate conditions of temperature (e.g., about 0° to about 70° C.) and hydrogen pressure (e.g., about 1 to about 10 atmospheres). While higher pressures may be desirable in selected instances, such moderate pressures permit the use of much less elaborate and expensive equipment. Suitable noble metal catalysts include platinum, palladium, rhenium, rhodium and ruthenium, either of the supported or non-supported type, as well as the known catalytic compounds thereof such as the oxides, chlorides, etc. Examples of suitable catalyst supports include carbon, silica and barium sulfate. The elemental catalysts may be preformed or formed in situ by prereduction of an appropriate salt of the catalytic compound. Examples of preferred catalysts are 5% palladium-on-carbon, 5% platinum-on-carbon; 5% rhodium-on-carbon, platinum chloride, palladium chloride, platinum oxide and ruthenium oxide. Most preferred in the present instance is palladium-on-carbon. Solvents generally suitable for the present hydrogenation include lower alcohols, ethyl acetate and tetrahydrofuran.

The ethers (i.e., compound 5) in Scheme 1 are deblocked to form the corresponding phenol derivative, again, by conventional methods; for example, using aqueous HBr, or BBr$_3$.

The phenolic alkylations found in Scheme 1 represent conventional nucleophilic displacement reactions. These displacements are generally carried out in the presence of a base of sufficient strength to convert the displacing phenol, alcohol or thiol to its salt, and in a quantity at least sufficient to neutralize the by-product acid (HX$^2$, HBr). In those substrates which contain an aliphatic alcohol group (e.g., a compound IV wherein Y$^2$ is H and Y$^3$ is OH), bases of sufficient strength to convert that group to the anion will generally be used in an amount no more than sufficient to convert the more acidic phenol to the salt. When either of the reactants contains a group of acidity similar to or greater than that of the nucleophilic displacing compound, such potentially interfering groups are best introduced in protected form (e.g., a heteroaromatic phenolic group as methoxy or benzyloxy, a carboxy group as methyl or benzyl ester, removable by hydrolysis or hydrogenolysis according to methods detailed elsewhere herein). The present nucleophilic displacements are carried out in a reaction-inert solvent, preferably one which is much less acidic than the displacing phenol, alcohol or mercaptan. Most preferred are polar, aprotic solvents such as dimethylformamide or acetone, usually with a molar excess of the more readily available of the two reactants. Temperature is not critical, e.g., about 10° to about 70° C. is usually satisfactory with ambient temperature most convenient. In one preferred variant, the phenol, alcohol or mercaptan is irreversibly converted to the anion with a base such as sodium hydride. Other preferred variants employ K$_2$CO$_3$ as base in the presence of NaI, or Cs$_2$CO$_3$ as base in the presence of CsI.

The "reduction" reactions of Scheme 1 require the reduction of a ketone to a secondary alcohol, for which a number of selective reagents are available. Where no other LiAlH$_4$ reducible groups (such as carboxy, methoxycarbonyl) are present, that reagent is well suited for this purpose. On the other hand, NaBH$_4$ is preferred as the reducing agent when such reducible groups are present. In either case, these hydride reductions are generally carried out in a reaction-inert solvent (such as tetrahydrofuran in the case of LiAlH$_4$ and methanol or a combination of methanol and tetrahydrofuran in the case of NaBH$_4$). The temperatures are between about −50° to about 50° C. A temperature between about −45° to about −50° C. preferred. The present reduction step offers the potential of producing a mixture of cis- and trans-isomers (as illustrated in the formulae IA and IB, above) and in the present hydride reduction, that is the result which is generally observed. If one or the other of these isomers is particularly desired, one can usually find a reduction method and set of conditions which will favor the desired isomer. For example, NaBH$_4$ reduction in the presence of cerium chloride will generally strongly favor the cis-isomer. Catalytic hydrogenation is also a generally useful reduction method, usually carried out under conditions which are somewhat more vigorous than those described above (e.g., prolonged time, higher catalyst level, higher temperature and/or higher pressure). Hydrogenation is preferably carried out on substrates such as

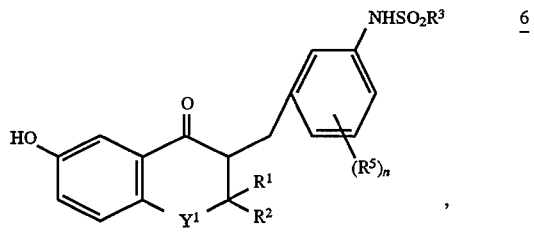

wherein R$^1$, R$^2$, R$^3$, R$^5$, Y$^1$ and n are defined as above, which contain no other readily hydrogenated group. The cis- and trans-isomers formed in the present reduction are generally separable by standard chemical methods (e.g., selective or fractional crystallization, chromatography, etc.)

Those ketone compounds of the formula I or compounds of the formula IV in the first alternative, wherein Y$^2$ and Y$^3$ form a carbonyl group, and contain an asymmetric carbon at the alpha-position which is adjacent to the carbonyl group and, therefore, are racemic compounds capable of resolution into optically active enantiomers, e.g., by conversion of the racemate into diastereomeric salts with an optically active acid, which are generally separable by a fractional crystallization process. Alternatively, if the substrate contains a carboxy group, separable diastereomeric salts are formed with an optically active organic amine. Optical activity can also be induced by use of an optically active reagent in the step by which the asymmetric carbon is formed, e.g., use of an optically active Wilkinson type catalyst, or a noble metal supported on an optically active support, in the hydrogenation step. The optically active ketones are also available by conventional reoxidation of an optically active alcohol of the next paragraph, e.g., via the Jones oxidation, which is exemplified below.

The hydroxy compounds of the formula I contain two asymmetric carbons-corresponding to two racemates and four optically active compounds. One of these racemates is the cis-isomer, and the other the trans-isomer. Each of these racemates is capable of resolution into a pair of enantiomers via diastereomeric salts, as detailed in the preceding paragraph. It is preferred, however, to convert the racemic alcohol to corresponding diastereomeric esters, as illustrated in Scheme 2, or urethanes formed with an optically active acid or isocyanate. Such covalently bonded derivatives may generally be subjected to a broader variety of separation methods .(e.g., chromatography) than are diastereomeric salts. As illustrated in Scheme 2 such diastereomeric esters e.g., 9 and 10 are formed from the alcohols 8 and the optically active acids by standard methods, generally those involving activation of the acid, e.g., as the acid chloride, as a mixed anhydride with an alkyl chloroformate, or with a dehydrative coupling agent such as dicyclohexylcarbodiimide. Preferred optically active acids in the present case are S-O-acetyl-mandelic acid and t-boc-D-tryptophan. Most preferred is t-boc-D-tryptophan. The resulting diastereomeric esters are separated, e.g., by chromatographic methods, and hydrolyzed by conventional methods, e.g., aqueous acid or aqueous base, to obtain the enantiomeric, optically active alcohols 11 and 12.

An alternative method for the preparation of a compound of formula 11 wherein Y$^1$ is O is illustrated in Scheme 3 wherein the enantiomeric acid 12, (prepared by the method of Murtiashaw, as described in the copending U.S. patent application filed Oct. 21, 1992 is converted to the optically active compound 14 by means of a Curtius degradation.

Alkylation of the phenolic hydroxyl of compound 14 and sulfonation of the resultant compound 15 to form the compound 11 (corresponding to formula IC) are described above with respect to Scheme 1.

Alternatively, as shown in scheme 4, the phenolic group of compound 19 is converted to an ether 20 as described with respect to scheme 1 for the conversion of compound 7 to compound 8. The chromanone ether 20 is then converted to the racemic chromanol 21 by the method described in scheme 1 for the conversion of compound 6 to compound 7 thereof.

As shown in scheme 5 the ethers wherein $R^9$ is phenyl, i.e., compound 28 wherein the 6-hydroxy group of the chromanone is deblocked and the nitro group simultaneously reduced, are formed by treating compound 27 with hydrogen over a hydrogenation catalyst in a "reaction-inert" medium. Compound 31 is prepared by treatment of compound 28 with a phenolic alkylating agent to form compound 29 which is then converted to compounds 30 and 31 by the methods described with respect to scheme 1. The racemic compound 31 is resolved by the method described with respect to scheme 2.

Scheme 6 illustrates an alternative method for preparing a compound 56, corresponding to compound 8 of scheme 1, wherein $R^1$ is hydrogen and $R^2$ is $(C_1-C_6)$alkyl. Preferably $R^2$ is methyl. According to this method compound 45 is converted to compound 47 by the method described with respect to scheme 1 for converting compounds 1 and 2 to compound 4. Compound 47 is then converted to the esteroxamide 48 by treatment with an acylating agent, in an inert solvent, in the presence of a tertiary amine. Acylating agents useful in this aspect of the invention include acyl halides, e.g., chlorides and bromides, and acyl anhydrides. Tertiary amines include tri($[C_1-C_6]$alkyl)aminopyridines and the like.

Compound 50 is formed by treatment of compound 48 with a metal hydride followed by a mineral acid in a $(C_1-C_6)$alkanoic acid to form compound 49 which is then treated with a mineral acid in aqueous alcohol. Compound 52 is prepared from compound 50 by the methods described, in scheme 1 for preparing compound 6 from compound 4. Compound 53 is prepared, according to the method of scheme 4 for preparing compound 20 from compound 19, from compound 52. Compound 54 is prepared from compound 53 by treatment with a regiospecific reducing agent, i.e., one which will selectively reduce double bonds in the presence of keto groups. Such reducing agents include L-Selectride® (lithium tri-s-butylborohydride, 1.0M solution in tetrahydrofuran). Compound 56 is prepared from compound 54 by further sulfonation of the sulfonylamino group by known methods followed by reduction of the oxochromanyl group by known means. The racemic 56 is resolved by the method described with respect to scheme 2.

As shown in scheme 7 compound 62, prepared from the corresponding carboxylic acid (compound 12 in scheme 3) is treated with hydrogen over Pd(OH)$_2$ in glacial acetic acid to form compound 62 which is then converted to its benzyl ether 64 by treatment with a benzyl halide in the presence of a base and an inert solvent. A preferred base for this step is potassium acetonate. The benzylether is converted to the free acid 65 which is then converted to the phenylacetamide 66 by known methods. Hydrogenolysis of compound 66 followed by treatment with a benzylhalide in the presence of a base yields compound 68 which is converted to its trifluorosulfonamide by the methods indicated above. In this case the optically pure sulfonamide is obtained and further resolution is not required.

The prodrug esters of the present invention are prepared by methods similar to those used in the synthesis of esters in the preceding paragraph. Esters with alpha-amino acids, including natural L-amino acids, will generally be prepared from the appropriate amino acid in which the alpha-amino group, substituent NH$_2$ or NH groups (e.g., lysine, ornithine, arginine, histidine, tryptophan), hydroxy groups (serine, homoserine, threonine, tyrosine), mercapto groups (cysteine) and substituent carboxy groups (glutamic acid, aspartic acid) are in protected forms (e.g., N-benzyloxycarbonyl, O- and S-benzyl) which may, generally, be deprotected by catalytic hydrogenation in a subsequent step. Similarly, in the case of esters with primary or secondary amino substituents, the acids will be coupled with amino group protectors. Such protection is, of course, unnecessary with those acids containing tertiary amino substitutents. Finally, the carboxy substituted esters are most conveniently prepared from the cyclic anhydrides:

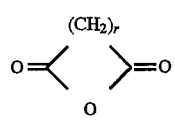

wherein r is 2 or 3.

The invention also relates to the salts of the compounds of formula I, their enantiomers, diastereomers and racemates thereof, which salts can be prepared by the reaction of the said compounds with a base having a non-toxic, pharmaceutically acceptable cation. In general, any base which will form a pharmaceutically acceptable salt with a sulfonamide and whose pharmacological properties will not cause an adverse physiological effect when ingested is considered as being within the scope of this invention. Suitable bases thus include, for example, inorganic bases such the alkali metal and alkaline earth metal hydroxides and carbonates; ammonia; and organic bases such as primary, secondary and tertiary amines, such as, monoalkylamines, dialkylamines, trialkylamines and nitrogen containing heterocyclic amines.

The pharmaceutical compositions of the present invention comprise a compound of formula I, or a pharmaceutically acceptable salt or prodrug thereof, and may also contain a pharmaceutically acceptable carrier and optionally other therapeutic ingredients. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted mines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethlenediamine, glucosamine, methylglucamine, theobromine, purines, piperidine, piperazine, N-ethylpiperazine, polyamine resins and the like.

The pharmaceutically acceptable acid addition salts of the compounds of formula 1 wherein $Y^1$ is $NR^6$, wherein $R^6$ is defined as above, or any of the substituents Ar, $R^1$, $R^2$, $R^3$ and $R^5$ is basic are those in which the anion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, ethanol, ethyl acetate and preferably acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of acid addition salt formation of the substances of Formula I include inorganic acids such as sulfuric, phosphoric, nitric, hydrochloric, hydrobromic and hydroiodic and organic acids such as aliphatic, alicyclic, araliphatic, aromatic, or heterocyclic monobasic or polybasic carboxylic or sulfonic acids including citric, acetic, benzoic, cinnamic, mandelic, mucic, isethionic, palmitic, heptanoic, formic, propionic, pivalic, oxalic, malonic, succinic, pimelic, fumaric, tartaric, maleic, malic, aminocarboxylic, sulfamic, salicyclic, phenylpropionic, gluconic, ascorbic, nicotinic, isonicotinic, methanesulfonic, ethanesulfonic, β-hydroxy-ethanesulfonic, p-toluenesulfonic, naphthalene-mono- and di- carboxylic and sulfonic acids and the like.

These salts can easily be prepared by simply treating the basic compounds of formula I with an aqueous solution of the desired pharmacologically acceptable cation, and then evaporating the resulting solution to dryness, preferably under reduced pressure. Alternatively, they may also be prepared by mixing lower alkanolic solutions of the acidic and basic compounds and then evaporating the resulting solution to dryness in the same manner as before. In either case, stoichiometric quantities of reagents are preferably employed in order to ensure completeness of reaction and maximum yields of the desired final product.

For instance, the salt-formation step may be carried out by using a substantially equimolar amount of the appropriate acid in an aqueous solvent medium or in a suitable organic solvent such as methanol or ethanol. Upon careful evaporation of the solvent, the solid salt product is readily obtained.

For a useful discussion of pharmaceutical salts see S. M. Berge et al., Journal of Pharmaceutical Sciences, 66, 119 (1977), the disclosure of which is incorporated herein by reference.

Concerning the biological activity of the present compounds, it is known that arachidonic acid is metabolized in mammals by means of two distinct pathways, one leading to prostaglandins and thromboxanes, the other to several oxidative products called leukotrienes, which are designated by letter number combinations such as $B_4$, $C_4$ and $D_4$. The first step in this oxidative pathway is the oxidation of arachidonic acid under the influence of 5-lipoxygenase enzyme, an enzyme whose action is generally inhibited by the active compounds of the present invention, thus blocking the synthesis of all leukotrienes. The active compounds of the present invention are, therefore, useful in the treatment or prevention of asthma (where $LTC_4$ and $LTD_4$ are understood to be mediators), arthritis (where $LTB_4$ is understood to be a mediator in inflammation), psoriasis (where $LTB_4$ is understood to be a mediator), ulcers (where $LTC_4$ and $LTD_4$ are understood to be mediators) and myocardial infarction (where $LTB_4$ is understood to be a mediator). Supplementing this enzyme inhibitory activity is the general ability of the active compounds to antagonize leukotriene $D_4$ (i.e., block $LTD_4$ receptors). In general, the active compounds also antagonize leukotriene $B_4$. For a review concerning leukotrienes, see Bailey et al., Ann. Reports Med. Chem. 17, pp. 203–217 (1982).

The in vitro activity of the active compounds is tested as follows. RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed 1 time with RPMI 1640 (GIBCO) and resuspended n RPMI 1640 plus 1 microM glutathione to a cell density of $1\times10^7$ cells/ml. A volume of 0.5 ml of the cell suspension is incubated at 30° C. with 0.001 ml of dimethylsulfoxide solution of drug for 10 minutes. The reaction is started by a simultaneous addition of 0.005 ml ($^{14}$C)-arachidonic acid in ethanol and 0.002 ml A23187 in dimethylsulfoxide to give final concentrations of 5.0 and 7.6 microM, respectively. After a 5 minute incubation at 30° C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent system of acetonitrile/$H_2O$/acetic acid (0.1%) with a linear acetonitrile gradient from 35% to 70% over 15 minutes at 1 ml/minute. Quantitation is accomplished with a Berthold (trademark) Radioactivity Monitor equipped with a built-in integrator and a 0.2 ml flow cell mixing 2.4 ml/minute Omnifluor (NEN) with column effluent. Integration units for each product are calculated as a percentage of total integration units, and then compared to the average control levels. The results are expressed as "Percent of Control" and are plotted vs the log of drug concentration. The $IC_{50}$ values are estimated by graphical inspection.

The leukotriene $D_4$ ($LTD_4$ receptor assay tests the ability of a compound to compete with radiolabelled $LTD_4$ for specific $LTD_4$ receptor sites on guinea pig lung membranes. In this test, normal 3–4 week-old guinea pigs are acclimatized under standard conditions for 3 days prior to being sacrificed. Final animal age: 24–31 days. The guinea pigs are stunned by a blow to the back of the neck, and exsanguinated by cutting the carotid artery. The chest cavity is opened and the lungs are removed, rinsed in 50 mM Tris buffer (pH 7.0) and placed in clean buffer. In this and all subsequent operations, all tissue and buffer are kept on ice throughout the preparation, and all centrifugation is carried out at 4° C. Bronchi and connective tissue are trimmed from the lungs. The tissue is weighed and placed in 50 ml polycarbonate tubes with buffer at a ratio of 1 gm tissue/3 ml buffer. The tissue is homogenized by a Tekmar Tissumizer (trademark) at full speed for 30 seconds and centrifuged in a Sorvall (trademark) SS-34 rotor at 3250 rpm×15 minutes. The supernatant is centrifuged at 19,000 rpm×10 minutes. The resulting pellet is resuspended in buffer with the Tissumizer at medium speed (position 75) for 10 seconds. The resuspension is again centrifuged at 19,000 rpm×10 minutes. The resulting pellet is resuspended by the Tissumizer at slow speed (position 50) for 10 seconds in 1 ml buffer/g of starting tissue. This final suspension is stirred at 4° C. while aliquoted to polypropylene tubes and stored at −70° C. The following are added to a 12×75 mm polystyrene tube:

(1) 25 microL of one of the following:
   A. Dimethylsulfoxide (to determine total binding)
   B. 1 μM LTD$_4$ (to determine non-specific binding)
   C. 30 nM to 100 μM of the compound of Formula I in dimethylsulfoxide (2) 0.025 ml 3H-LTD, (specific activity 30–60 Ci/mmol) in 50 mM Tris (pH 7.0)+10 μM L-cysteine (12,000–15,000 cpm/0.025 ml)

(3) 0.2 ml diluted membrane preparation (1 mg/ml) (The preparation is diluted in 50 μM Tris buffer+MgCl$_2$ such that in 200 μL protein, a 10 μM MgCl$_2$ concentration is achieved).

The reaction tubes are incubated at 25° C. for 30 minutes. Four ml of cold Tris buffer+10 μM MgCl$_2$ are added to each tube. The contents are quickly filtered through a Whatman GF/C filter with a Yeda separation device. The filter is washed 3X with 4 ml Tris-MgCl$_2$ buffer. The filter is transferred to a scintillation vial. Ultrafluor scintillation fluid is added. The vial is capped, vortexed and counted for 3 hours. Percent specific binding (% SB) is calculated using the formula $$\% \, SB = (X - NSB)/(TB - NSB),$$

where

X=cpm sample
NSB=cpm non-specific binding
TB=cpm total binding

Percent specific binding is graphed as a function of compound concentration. IC$_{50}$ is that concentration at which 50% SB occurs. K$_i$ is calculated by using the formula:

$$K_i = (IC_{50})/[1 + (L/Kd)],$$

where

L=concentration of ligand added (μM)
=cpm added/cpm of 1 μM $^3$H-LTD$_4$
K$_d$=1 microM (dissociation constant)

To evaluate the active compounds of the present invention, in vivo, they are tested by the so-called PAF lethality assay procedure: Materials:

Mice: CD1 males, all approximately the same weight (about 26 grams), 12 per group.

Vehicle for oral drug dosing: EES (5% ethanol, 5% emulphor, 90% saline). Stored at room temperature.

Drugs: For routine screening at 50 mg/kg, 20 mg drug is dissolved in 4 ml EES, using sonication in a sonicator bath or grinding in a Ten Broeck (trademark) grinder to dissolve drug if necessary. If solubility is still a problem, the drug is used as a suspension.

Vehicle for i.v. Injection: Saline with 2.5 mg/ml Bovine Serum Albumin (BSA, Sigma #A4378) and 0.05 mg/ml Propranolol (Sigma #P0884). Prepared fresh daily and kept at room temperature.

Platelet Activating Factor (PAF): A 10 μM stock solution is prepared by dissolving 1 mg PAF (Calbiochem #429460) in 0.18 ml ethanol. This stored at −20° C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.

Positive Control: Phenidone is used at 25 mg/kg (its approximate ED 50).

Method:

45 minutes before PAF injection, mice are treated orally with drug using 0.1 ml/10 grams body weight. 35 to 40 minutes later they are placed under a heat lamp to dilate the caudal vein for PAF injection. PAF is injected i.v. at 0.1 ml/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided. Variations:

1. The time for oral dosing can be changed.
2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

For use in the prevention or treatment of asthma, arthritis, psoriasis and gastrointestinal ulcers in a mammal, including man, a compound of the formula I is given in a 5-lipoxygenase inhibiting and/or leukotriene receptor blocking amount of about 0.5–50 mg/kg/day, in single or divided daily doses. A more preferred dosage range is 2–20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow.

The active compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in, e.g., the U.S. Pat. Nos. 4,256,108; 4,166,452;and 4,265,874 to form osmotic therapeutic tablets for control release.

The hard capsules for oral use may also be presented as gelatin capsules wherein the active ingredient is mixed with an inert solid diluent, for example, calcium carbonate, calcium phosphate or kaolin, or whereas the soft capsules may be presented as gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinyl pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monocleate, or condensation products of ethylene oxide with partial esters derived from fatty acids and hexitol anhydrides, for example polyethylene sorbitan monocleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents may also be present.

The pharmaceutical compositions of the invention may also be in the form of oil-in water emulsions. The oily phase may be a vegetable oil, for example, olive oil or arachis oil; a mineral oil such as liquid paraffin or mixtures of these. Suitable emulsifying agents may be naturally occurring gums, for example, gum acacia or gum tragacanth; naturally-occurring phosphatides such as example soy bean and lecithin; and esters or partial esters derived from fatty acids and hexitol anhydrides, for example, sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulation may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The active compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For topical use, creams, ointments, jellies, solutions or suspensions, etc., containing the active compounds of the invention are employed.

For administration by inhalation, the active compounds of the invention are conveniently delivered in the form of an aerosol spray presentation from pressurized packs or a nebulizer. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

The amount of active ingredient that may be combined with the carrier materials to produce a single dosage form will vary depending upon the host treated and the particular mode of administration. Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The present invention is illustrated by the following examples, but is not limited to the details thereof.

EXAMPLE 1

Synthesis of 6-methoxy-3-(3-nitrobenzylidene)-chroman-4-one

A mixture of 10.0 g (56.1 mmol) of 6-methoxychromanone, 8.48 g (56.1 mmol) of 3-nitrobenzaldehyde and 4.7 mL (56.1 mmol) of pyrrolidine in 30 mL methanol was allowed to stir at room temperature under $N_2$ atmosphere. After 48 hours, the reaction mixture was filtered and the precipitate washed with methanol and dried to yield 11.44 g of yellow powder (65%). A small sample was recrystallized from isopropylether/$CH_2Cl_2$ for analytical data. M.p. 157°–159° C.; MS: C: 311.0794;F: 311.0796; $^1H$ NMR (AC 300, $CDCl_3$): δ5.27 (d, 2H, J=1.9 Hz); 3.84 (s, 3H); IR: 1670, 1490 $cm^{-1}$. Analysis: calculated: C. 65.59, H 4.21, N 4.50%; found: C. 65.33, H4.57, N 4.47%.

EXAMPLE 2

Synthesis of 3-(3-aminobenzyl)-6-methoxy-chroman-4-one

A mixture of 10.20 g (32.8 mmol) of the product of Example 1 and 2 g of 10% Pd/C in 200 mL $CH_3OH$ and 200 mL tetrahydrofuran was shaken on a Parr (trademark) hydrogenation apparatus at 25 psi $H_2$ at room temperature. After 30 minutes the reaction mixture was filtered through diatomaceous earth (Celite [trademark]), and the filtrate concentrated in vacuo to yield 9.94 g of a yellow solid. Silica gel chromatography eluting with 5% ethyl acetate-$CH_2Cl_2$ afforded 8.53 g of a yellow solid (92%). A small sample was recrystallized from ethyl acetate-hexane to obtain analytical data. M.p. 137°–139° C.; MS: 283$M^+$, 107 Base; $^1H$ NMR (AC 300, $CDCl_3$): δ4.3 (1H, m); 4.15 (1H, m), 3.82 (3H, s); 3.7 (1H, m); 3.67 (1H, m); 2.9 (1H, m); 2.6 (1H, m); IR: 3430, 3250, 1660 $cm^{-1}$. Analysis: calculated: C. 72.07, H 6.05, N 4.94%; found: C: 71.69, H 6.01, N 4.96%.

EXAMPLE 3

Synthesis of N-[3-(6-methoxy-4-oxo-chroman-3-ylmethyl)phenyl]trifluoromethanesulfonamide A room temperature solution of 5.35 mL (31.8 mmol) of trifluoromethanesulfonic acid anhydride (triflic anhydride) in 50 mL $CH_2Cl_2$ was added to a 0° C. solution of 8.18 g (28.9 mmol) of the product of Example 2 and 4.43 mL (31.8 mmol) of triethylamine in 300 mL $CH_2$ $Cl_2$. After 30 minutes at 0° C., the reaction mixture was warmed to room temperature, and chromatographed directly on a silica gel column eluting with 3% ethyl acetate-$CH_2Cl_2$. The yield was 10.23 g of an amber oil (85%). An analytical sample was obtained by recrystallization from ethyl ether-hexane. M.p.: 114°–116° C.; MS: C: 415.0702, F: 415.0708; $^1H$ NMR (AC 300, $CDCl_3$) δ3.81 (3H, s); IR: 3100, 1655 $cm^{-1}$.

EXAMPLE 4

Synthesis of N-[3-(6-hydroxy-4-oxo-chroman-3-ylmethyl)phenyl]trifluoromethanesulfonamlde A solution of 10.21 g (24.6 mmol) of the product of Example 3 in 100 mL 48% HBr and 100 mL of glacial acetic acid was heated to reflux under $N_2$. After 2½ hours, the reaction mixture was cooled to room temperature, diluted with 2 L of $H_2O$/ice and the pH adjusted to 5 with 2N NaOH. The aqueous mixture was extracted three times with ethyl acetate, and the ethyl acetate extracts were combined, washed once with brine, then dried over $Na_2SO_4$ and concentrated in vacuo to yield 9.25 g of brown crystals. Silica gel chromatography eluting with 4% $CH_3OH$—$CH_2Cl_2$ afforded 8.89 g of off-white powder (90%). A small sample was recrystallized from ethyl acetate-hexane for analytical data. M.p.: 176°–178° C.; MS: 401$M^+$, 136 Base; $^1H$ NMR (AC 300, dimethylsulfoxide-$d_6$): δ9.39 (1H, br s); 4.3 (dd, 1H); 4.1 (dd, 1H); 3.1 (dd, 1H); 3.0 (m, 1H); 2.7 (dd, 1H); IR: 3430, 3260, 1675 $cm^{-1}$. Analysis: calculated: C. 50.86, H 3.52, N 3.49; found: C. 50.76, H 3.42, N 3.46%.

EXAMPLE 5

Synthesis of (±) N-[3-(4,6-dihydroxy-chroman-3-ylmethyl)phenyl]trifluoromethanesulfonamide 822 mg (21.7 mmol) of $NaBH_4$ were added in 3 portions to a −55° C. solution of 8.72 g (21.7 mmol) of the product of Example 4 and 8.89 g (23.9 mmol) of $CeCl_3$•$7H_2O$ in 150 mL $CH_3OH$ and 50 mL tetrahydrofuran. After 2 hours at −55° C., the reaction mixture was warmed to room temperature, concentrated in vacuo, diluted with 1 L ethyl acetate, washed twice with $NH_4Cl$, once with $H_2O$, once with brine and then dried over $Na_2SO_4$. Filtration, concentration and drying yielded 11.0 g of white oily foam, which was purified on a silica gel column eluting with 3% $CH_3OH$—$CH_2Cl_2$ to afford 7.25 g of white foam (83%). A sample was recrystallized from ethyl acetate-hexane for analysis.

M.p. 68°–73° C.; MS: C: 403.0702, F: 403.0722; $^1H$ NMR (AC 300, dimethylsulfoxide-$d_6$): δ4.28 (1H, d); 3.8 (2H, m); IR: 3320, 1498 $cm^{-1}$. Analysis: calculated: C. 50.61, H 4.00, N 3.47%; found C. 50.04, H 4.18, N 3.24%.

EXAMPLE 6

Synthesis of (±) N-[3-(6-(5-fluorobenzothiazol-2ylmethoxy)-4-hydroxy-chroman-3-ylmethyl)-phenyl]trifluoromethanesulfonamide 599 mg (2.97 mmol) of 2-chloromethyl-5-fluorobenzothiazole were added to a room temperature suspension of 1.00 g (2.48 mmol) of the product of Example 5 and 1.02 g (7.44 mmol) of $K_2CO_3$ in 10 mL of dry DMF. After being stirred 64 hours at room temperature, the reaction mixture was diluted with 400 mL ethyl acetate and 400 mL of 0.5N HCl were added. After being stirred for 5–10 minutes, the layers were separated. The ethyl acetate layer was washed twice with $H_2O$, once with brine, and dried over $Na_2SO_4$. Filtration, concentration and drying in vacuo afforded a yellow oil, which was purified on a silica gel column eluting with 2% $CH_3OH$—$CH_2Cl_2$ to afford 0.85 g of a yellow amorphous solid (60%). Recrystallization from ethyl acetate/hexane yielded 648 mg of pale yellow crystals. M.p.: 102°–106° C.; MS: 568M+; $^1H$ NMR (AC 300, dimethylsulfoxide-$d_6$): δ8.14 (1H, dd); 7.84 (1H, dd); 5.49 (2H, s); 3.89 (d, 2H); IR: 1740 $cm^{-1}$. Analysis: calculated: C 52.81, H 3.55, N 4.93%: found: C 53.17, H 3.34, N 4.52%.

The compounds of Examples 7 and 8 were prepared according to the method of Example 6.

| Example | Ar | Yield (%) | m.p. | | | | |
|---------|----|-----------|------|---|---|---|---|
| 7 | (7-chloroquinolin-2-yl) | 53 | 126–130° (d) | CHN | C: | C 56.01 | H 3.83 | N 4.84 |
| | | | | | F: | 55.90 | 3.81 | 4.70 |

MS: 578 M+, Base
$^1$H NMR (AC 300, dimethylsulfoxide-$d_6$):
δ 5.27 (s, 2H)
IR: 2800–3500, 1495 cm$^{-1}$

| 8 | (5,6-difluorobenzothiazol-2-yl) | 45 | 95 (d) | MS: | C: 586.0657 |
| | | | | | F: 586.0615 |

$^1$H NMR (AC 300, dimethylsulfoxide-$d_6$): δ 5.48 (s, 2H)
IR: 3540, 2400–3200, 1502 cm$^{-1}$

EXAMPLE 9

Resolution of (±) N-[3-(6-(5-fluorobenzothiazol-2ylmethoxy)-4-hydroxy-chroman-3-ylmethyl)-phenyl]trifluoromethanesulfonamide: formation of (+) 2-t-butoxycarbonylamino-3-(1H-indol-3-yl) propionic acid 6-(5-fluorobenzothiazol-2ylmethoxyl-3-[3-trifluoromethanesulfonylamino) benzyl]-chroman-4-ylester[Compound 9A] and (−) 2-t-butoxycarbonylamino-3-(1H-indol-3-yl) propionic acid 6-(5-fluorobenzothiazol-2ylmethoxy)-3-[3-trifluoromethanesulfonylamino)benzyl]-chroman-4-yl ester [Compound 9B]

836 mg (4.05 mmol) of dicyclohexylcarbodiimide were added in one portion to a room temperature solution of 2.30 g (4.05 mmol) of the product from Example 6, 1.23 g (4.05 mmol) of t-BOC-D-tryptophan, and 495 mg (4.05 mmol) of 4-dimethylaminopyridine in 50 mL of anhydrous CH$_2$Cl$_2$. After being stirred 40 hours at room temperature under N$_2$, the reaction mixture was filtered, and the filtrate concentrated in vacuo. The residue was triturated with about 150 mL ethyl acetate, filtered, and the second filtrate diluted with about 350 mL ethyl acetate. The ethyl acetate layer was washed twice with 1N HCl, once with H$_2$O, once with brine, and dried over Na$_2$SO$_4$. Filtration, concentration, and drying in vacuo yielded 3.66 g of crude product, an orange foam. Silica gel chromatography, eluting with 10% ethyl acetate/CH$_2$Cl$_2$ followed by 20% ethyl acetate-CH$_2$Cl$_2$, afforded the following: Compound 9A (LP product), 1.41 g yellow foam, 82% yield; Compound 9B (MP product), 1.47 g yellow foam, 85% yield.

MS (LSIMS): Compound 9A 855 (M+H), 551 (Base); Compound 9B 855 (M+H), 854 (M+), 551 (Base); $^1$H NMR (AC 300, CDCl$_3$): Compound 9A has a doublet of doublets at δ5.23; and Compound 9B has a singlet at δ5.29.

EXAMPLES 10 AND 11

The compounds of Examples 10 and 11 were prepared according to the method of Example 9.

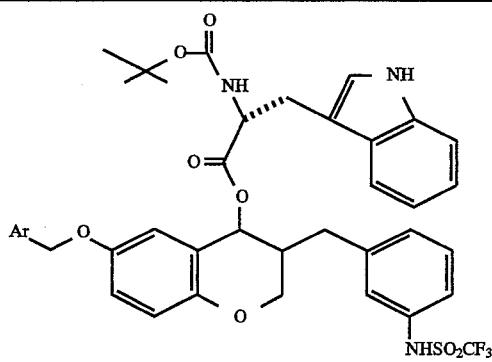

| Example | Ar | Enantiomer | |
|---|---|---|---|
| 10 | (chlorine-substituted quinoline) | (+) | ¹H NMR(AC 300, CDCl₃): δ 1.45 (s, 9H); δ 5.05, 5.18 (2H, AB)<br>MS (LSIMS): 865 (M + H), 561 (Base) |
|  |  | (−) | ¹H NMR (AC 300, CDCl₃): δ 1.44 (s, 9H), 5.20 (s, 2H)<br>MS (LSIMS): 865 (M + H), 561 (Base) |
| 11 | (difluorobenzothiazole) | (+) | ¹H NMR (AC 300 CDCl₃): δ 1.46 (s, 9H); δ 5.21 (2H)<br>MS (LSIMS): 872 (M + H), 569 Base |
|  |  | (−) | ¹H NMR (AC 300, CDCl₃): δ 1.43 (s, 9H): δ 5.28 (s, 2H)<br>MS (LSIMS): 872 M+, 184 Base |

EXAMPLE 12

(+) N-[3-(6-(5-fluorobenzothiazol-2ylmethoxy)-4-hydroxy-chroman-3-ylmethyl)phenyl] trifluoromethanesulfonamide 1.37 g (1.60 mmol) of the compound 9A from Example 9 was suspended in 45 mL CH₃OH and 15 mL 1N NaOH, and the reaction mixture was allowed to reflux for 30 minutes. After cooling to room temperature, about ½ the volume of the reaction mixture was removed on a rotary evaporator. The residue was diluted with 500 mL H₂O, acidified to pH 1–2, stirred for 5–10 minutes, then extracted three times with ethyl acetate. The ethyl acetate extracts were combined, washed once with H₂O, once with brine, and dried over Na₂SO₄. Filtration, concentration and drying in vacuo yielded 1.41 g of crude product. Silica gel chromatography eluting with 2% methanol-CH₂Cl₂ afforded 811 mg of yellow crystalline powder, which was recrystallized from ethyl acetate-hexane to give 778 mg of yellow cottony-needles. (85% yield) m.p.: 155°–157° C.; HRMS C: 568.0751, F: 568.0621; [α]$_D$=+57.8°, c=0.670 in tetrahydrofuran; ¹H NMR (AC 300, dimethylsulfoxide-d₆): δ5.46 (s, 2H). Identical with NMR spectrum of the compound from Example 6; ¹⁹F NMR (AC 300, dimethylsulfoxide-d₆): −75.8 (s, 3H); −116.4 (s, 1H); IR (cm⁻¹): 3400, 1498.

EXAMPLE 13

(−) N-[3-(6-(5-fluorobenzothiazol-2ylmethoxy)-4-hydroxy-chroman-3-ylmethyl)phenyl] trifluoromethanesulfonamide 1.44 g (1.68 mmol) of the compound 9B from Example 9 was suspended in 45 mL of CH₃OH and 15 mL in NaOH, and the reaction mixture was allowed to reflux for 30 minutes. After cooling to room temperature, ca. ½ the volume of the reaction mixture was removed on a rotary evaporator. The residue was diluted with 500 mL H₂O, acidified to pH 1.5, stirred 10 minutes, and extracted three times with ethyl acetate. The ethyl acetate extracts were combined, washed once with H₂O, once with brine, and dried over Na₂SO₄. Filtration, concentration and drying in vacuo yielded 1.43 g of yellow foam. Silica gel chromatography with elution by 2% CH₃OH/CH₂Cl₂ afforded 720 mg of yellow powdery crystals, which were recrystallized from ethyl acetate-hexane to give 660 mg of yellow cottony needles. (69% yield) m.p. 155°–157° C.; [α]$_D$=−55.5°, c=0.580 in tetrahydrofuran; MS (LSIMS) 569 M+H, 551 Base; HRMS (EI) C: 568.0751, F: 568.0786; ¹H NMR (AC 300, dimethylsulfoxide-d₆): δ5.49 (s, 2H). (identical with the NMR spectrum of the product of Example 12); ¹⁹F NMR (AC 300, dimethylsulfoxide-d₆): −75.8 ppm (s, 3H); −116.4 (s, 1H); IR (cm⁻¹) 3420 broad, 1498.

The compounds of Examples 14 and 15 were prepared according to the methods of Examples 12 and 13.

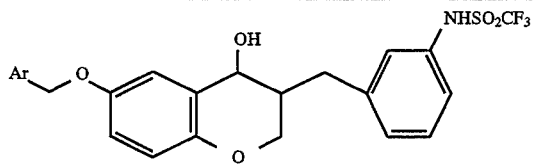

| Example | Ar | Enantiomer | m.p. | |
|---|---|---|---|---|
| 14 | (Cl-quinoline group) | (+) | 102–104 (d) | [α]$_D$ = +67.1°, C = 0.550 in tetrahydrofuran<br><br>CHN: C: C 55.24  H 3.95  N 4.77*<br>F: 55.50  3.80  4.70<br><br>MS (EI): C: 578.0890<br>F: 578.1159<br>$^1$H NMR (AC 300, dimethylsulfoxide-d$_6$): δ 5.27 (s, 2H).<br>Identical with the racemate of Example 7.<br>IR (cm$^{-1}$): 2800–3400; 1620; 1500<br>*Calcalualted for C$_{27}$H$_{22}$N$_2$O$_6$SF$_3$Cl.¼H$_2$O |
| | | (−) | 98–102 ° (d) | CHN: C: C 56.01  H 3.83  N 4.84*<br>F: 55.77  3.90  4.77<br>[α]$_D$ = −70.0°, c = 0.550 in tetrahydrofuran<br>MS (EI): C: 578.0890<br>F: 578.0921<br>$^1$H NMR (AC 300, dimethylsulfoxide-d$_6$): 5.27 (s, 2H).<br>Identical with racemate of Example 7.<br>IR (cm$^{-1}$): 2800–3400; 1620; 1500<br>*Calcalualted for C$_{27}$H$_{22}$N$_2$O$_6$SF$_3$Cl |
| 15 | (difluorobenzothiazole group) | (+) | 176–178 | CHN: C: C 51.18  H 3.26  N 4.78<br>F: 51.27  3.02  4.85<br><br>[α]$_D$ = +58.9°, c = 0.630 in tetrahydrofuran<br>MS (LSIMS): 587 M + H, 184 Base<br>$^1$H NMR (AC 300, dimethylsulfoxide-d$_6$): δ 5.48 (s, 2H).<br>Identical with racemate of Example 8.<br>IR (cm$^{-1}$): 3520, 1498, 1479 |
| | | (−) | 176–179 | CHN: C: C 51.18  H 3.26  N 4.78<br>F: 51.08  3.06  4.73<br><br>[α]$_D$ = −61.2°, c = 0.580 in tetrahydrofuran<br>MS (LSIMS): 587 M + H, 184 Base<br>$^1$H NMR (AC 300, dimethylsulfoxide-d$_6$): δ 5.48 (s, 2H).<br>Identical with racemate of Example 8.<br>IR (cm$^{-1}$): 3520, 1498, 1470 |

EXAMPLE 16

(+) N-[3-{4,6-dihydroxychroman-3-yl methyl}phenyl]benzoxamide 28.6 mL (134 mmol) of diphenylphosphorylazide were added neat to a room temperature solution of 38.3 g (128 mmol) of (3R-cis)-3-(4,6-dihydroxychroman-3-ylmethyl) benzoic acid (prepared according to the method described in co-pending U.S. patent application of Murtiashaw et al., attorney's docket no. PC 8328 filed concurrently herewith), 39.3 mL (282 mmol) of triethylamine, and 14.5 mL (140 mmol) of benzyl alcohol in 1100 mL of 1,4-dioxane. The reaction mixture was allowed to reflux for 3.5 hours, at which point it was cooled to room temperature. The reaction mixture was concentrated in vacuo to a volume of about 500 mL, and the residue was then diluted with 2.5 L of ethyl acetate. The ethyl acetate solution was washed twice with 500 mL $H_2O$ and once with brine and then dried over $Na_2SO_4$. Filtration, concentration and drying in vacuo yielded a brown oil, which was purified on a silica gel column (2%–5% $CH_3OH/CH_2Cl_2$) to afford 26.6 g of a white foam (51%). $[\alpha]_D$=+69.8°, c=0.860 in tetrahydrofuran; MS (LSI MS): 406 M+H, 405 Base; $^1$H NMR (AC 300, dimethylsulfoxide-$d_6$): δ5.13 (s, 2H); IR (cm$^{-1}$): 3300 Broad, 1705.

EXAMPLE 17

Synthesis of 3-(3-aminobenzyl-chroman-4,6-diol

A mixture of 25.5 g (62.9 mmol) of the title compound of Example 16, and 2.55 g of Pd(OH)$_2$/C (Pearlman's Catalyst, 20% Pd) in 500 mL $CH_3OH$ and 500 mL tetrahydrofuran was shaken on a Parr hydrogenation apparatus under 25 psi $H_2$. After 30 minutes, the reaction mixture was filtered through diatomaceous earth (Celite [trademark]) and the filtrate concentrated to yield 17.17 g of white foam. Chromatography on a silica gel column eluting with (4%–6% $CH_3OH$—$CH_2Cl_2$) yielded 15.6 g of pure product, a white powder (91% yield).

A sample was recrystallized from ethyl acetate-hexane for analytical data.

m.p.: 153°–156° C. MS (LSIMS): 272 M+, 155 Base; $^1$H NMR (AC 300, dimethylsulfoxide-$d_6$): δ8.82 (s, 1H); 4.96 (s, 2H, NH$_2$); IR (cm$^{-1}$): 3250 Broad, 3380, 3470, 1620. Analysis: calculated: C 70.83, H 6.32, N 5.16%; found C 70.38, H 6.06, N 5.11%.

EXAMPLE 18

Synthesis of 3-(3-aminobenzyl-6-(5,6-clfluorobenzothiazol-2-ylmethoxy)-chroman-4-ol 0.31 g (8.1 mmol) of sodium hydride (60% oil dispersion) was added in one portion to a room temperature solution of 2.0 g (7.37 mmol) of the product of Example 17 in 65 mL of anhydrous dimethylformamide. After being stirred for 40 minutes at room temperature under $N_2$ atmosphere, 2.1 g (9.58 mmol) of 2-chloromethyl-5,6-difluorobenzothiazole were added in one portion. The reaction mixture was allowed to stir 1 hour at room temperature, at which point 1.0 g of the chloride followed by 100 mg of sodium hydride were added. After being stirred an additional 20 minutes at room temperature, the reaction mixture was diluted with $H_2O$, neutralized to pH 6–7 and extracted twice with ethyl acetate. The ethyl acetate extracts were combined, washed three times with $H_2O$, and once with brine, and then dried over $Na_2SO_4$. Filtration, concentration, and drying gave a brown oil, which was chromatographed on a silica gel column (2% $CH_3OH$—$CH_2Cl_2$) to yield 2.36 g of an orange foam. (70% yield)

A small sample was crystallized from ethyl acetate-hexane to obtain analytical data. m.p.: 141°–143° C. $^1$H NMR (AC 300, CDCl$_3$): δ5.35 (s, 2H); 3.66 (s, 2H, NH$_2$); MS (LSIMS): 454 M+, 135 Base; R (cm$^{-1}$): 3380, 1495. Analysis: calculated: C 63.42, H 4.44, N 6.16%; found: C 63.66, H 4.45, N 5.96%.

The compounds of Examples 19–22 were prepared according to the method of Example 18.

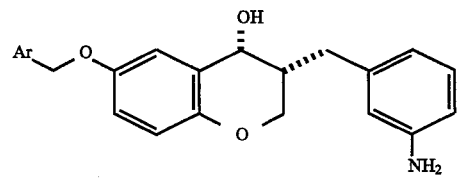

| Example | Ar | m.p. (°C.) | | | |
|---|---|---|---|---|---|
| 19 | (6-chloroquinolin-2-yl) | 150–152 | CHN: C: | C 69.87 | H 5.19 | N 6.27 |
| | | | F: | 69.88 | 5.19 | 6.21 |

MS (LSIMS): 447 M + H, Base
$^1$H NMR (AC 300, CDCl$_3$):
δ 5.27 (s, 2H); 3.65
(br s, 2H).
IR (cm$^{-1}$): 3200–3400, 1498

| 20 | (6-fluoroquinolin-2-yl) | | |

$[\alpha]_D$= +79.7°
MS: M+ = 430.1581

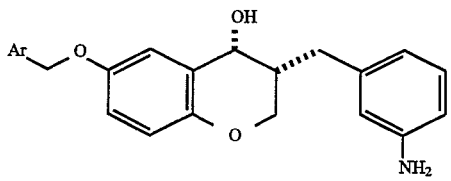

| Example | Ar | m.p. (°C.) | |
|---|---|---|---|
| 21 | (quinoline) | | $[\alpha]_D = +88.4°$<br>MS: M+ = 412.1720 |
| 22 | (cyclobutylmethyl-thiazole) | 46(d) | $^1$H NMR(AC 300, CDCl$_3$):<br>δ 5.19 (s, 2H); 3.98 (m, 2H);<br>3.7–4.1 (bs, 2H); 3.61 (q, 1H) |

EXAMPLE 23

Synthesis of N-(3-[6-(5,6-difluorobenzothiazol-2-ylmethoxy)-4-hydroxy-chroman-3-ylmethyl)-phenyl]-trifluoromethanesulfonamide 1.41 mL (8.37 mmol) of trifluoromethanesulfonic anhydride were added, dropwise, to a 0° C. solution of 3.46 g (7.61 mmol) of the product from Example 18, and 1.59 mL (11.4 mmol) of triethylamine in 300 mL anhydrous CH$_2$Cl$_2$. After being stirred 20 minutes at 0° C. under nitrogen atmosphere, 0.53 mL triethylamine and 0.64 mL trifluoromethanesulfonic anhydride were added to the reaction mixture. After 20 more minutes at 0°, the reaction mixture was diluted with 1.2 L of ethyl acetate, washed once with H$_2$O, once with brine and then dried over Na$_2$SO$_4$. Filtration, concentration and drying afforded 5.44 g of crude product, an amber foam, which was carried on to the next step directly.

35 mL of 1N NaOH were added to a solution of 5.44 g of the above crude product (mixture of mono- and bis-sulfonamides) in 150 mL CHaOH at about 5° C. After being stirred 40 minutes at room temperature, the reaction mixture was concentrated to about ½ the initial voldilute a rotary evaporator. The residue was diluted with 500 mL H$_2$O, acidified to pH 1.5, stirred 5 minutes, and extracted three times with ethyl acetate. The ethyl acetate extracts were combined, washed once with H$_2$O and once with brine and then dried over Na$_2$SO$_4$. Filtration, concentration and drying afforded an orange foam, which was chromatographed on a silica gel column (15%–20% ethyl acetate-CH$_2$Cl$_2$) to yield 3.31 g of pure product, a yellow foam. (74%) Recrystallization from ethyl acetate-hexane gave 2.96 g of yellow needles. m.p.: 177°–179° C. $[\alpha]_D$=+61.0°, c=0.790 in tetrahydrofuran; MS: (LSIMS) 587 M+H, 183 Base; $^1$H NMR (AC 300, dimethylsulfoxide-d$_6$): δ5.48 (s, 2H); IR (cm$^{-1}$): 3520, 1498, 1470.

Analysis: calculated: C 51.18, H 3.26, N 4.78%; found: C 51.0, H 2.99, N 4.71%.

The compounds of Examples 24–27 were prepared according to the method of Example 23.

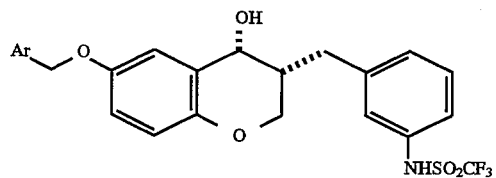

| Example | Ar | m.p. (°C.) | |
|---|---|---|---|
| 24 | (chloroquinoline) | 105–109 (d) | CHN: C: C 56.01 H 3.83 N 4.84<br>F: 56.64 4.02 4.58<br>$[\alpha]_D$ = +68.4°, c = 0.920<br>in tetrahydrofuran<br>MS (LSIMS): 579 M + H. 177<br>Base; $^1$H NMR (AC 300,<br>dimethylsulfoxide-d$_6$) δ 5.27<br>(5, 2H); Identical with CP-152,667<br>synthesized via resolution of<br>CP-146,742; IR (cm$^{-1}$):<br>Identical with the<br>CP-152,667 synthesized via |

-continued

| Example | Ar | m.p. (°C.) | |
|---------|----|-----------|--|
| | | | resolution of CP-146,742. |
| 25 | [structure: 6-fluoroquinoline] | 170–172 | $[\alpha]_D=$ 69.4° (tetrahydrofuran) |
| 26 | [structure: quinoline] | 166–167 | $[\alpha]_D=$ 68.54° (tetrahydrofuran) |
| 27 | [structure: cyclobutyl-vinyl-N-S] | 48(d) | $^1$H NMR (AC 300, CDCl$_3$) δ 6.92 (s, 1H); 5.28 (d, 2H); 3.56 (q, 1H) |

EXAMPLE 28

Synthesis of 7-methoxy-2-(3-nitrobenzylidene)-3,4-dihydro-2H-napthalen-1-one 2.5 mL (30.1 mmol) of pyrrolidine were added to a room temperature (about 25° C.) solution of 5.30 g (30.1 mmol) of 7-methoxy-1-tetraione and 4.55 g (30.1 mmol) of 3-nitrobenzaldehyde in 25 mL methanol. The reaction flask was fitted with a soxhlet extractor containing a thimble filled with 3 Å molecular sieves and a reflux condenser was placed on top of the soxhlet extractor. The reaction mixture was heated to reflux under N$_2$ for 18 hours, cooled to room temperature and filtered. The precipitate was washed twice with CH$_3$OH, and then dried on the funnel for 24 hours to yield 6.62 g of light tan powder. (71% yield).

This product was identical by $^1$H NMR, m.p., and MS, with the previously produced material. m.p.: 127°–129° C. MS (LSIMS): 310M+H, Base; $^1$H NMR (AC 300, CDCl$_3$): δ3.88 (s, 3H); 3.1 (m, 2H); 2.9 (m, 2H); IR (cm$^{-1}$): 1660, 1525. Analysis: calculated: C 69.89, H 4.89, N 4.53%; found: C 69.68, H 4.69, N 4.69%.

EXAMPLE 29

Synthesis of 2-(3-aminobenzyl-7-methoxy-3,4-dihydro-2H-napthalen-1-one

A mixture of 626 mg (2.02 mmol) of the product of Example 28 and 125 mg of 10% Pd/C in 15 mL tetrahydrofuran and 15 mL CH$_3$OH was hydrogensted on a Parr (trademark) Hydrogenator under 25 psi H$_2$ at room temperature. After 30 minutes, the reaction mixture was filtered through diatomaceous earth [Celite (trademark)], the filtrate concentrated in vacuo, and the residue purified by silica gel chromatography (5% ethyl acetate-CH$_2$Cl$_2$) to yield 369 mg of pure product, a yellow solid. m.p.: 159°–161° C. MS (LSIMS): 282 M+H, 155 Base; $^1$H NMR (AC 300, CDCl$_3$): δ3.84 (s, 3H); 3.64 (br s, 2H, NH$_2$); IR (cm$^{-1}$): 3360, 6450, 1665. Analysis calculated: C 76.85, H 6.81, N 4.98%; found: C 75.94, H 6.66, N 4.77%.

EXAMPLE 30

Synthesis of N-(3-(7-methoxy-1-oxo-1,2,3,4-tetrahydronaphthalen-2-ylmethyl)phenyl]-trifluoromethanesulfonamide 235 μl (1.40 mmol) of trifluoromethanesulfonic anhydride were added neat to a 0° solution of 356 mg (1.27 mmol) of the product of Example 29 and 195 μl (1.40 mmol) triethylamine in 20 mL anhydrous CH$_2$Cl$_2$. After 15 minutes at 0°, the reaction mixture was warmed to room temperature, and chromatographed directly on a silica gel column eluting with 3% ethyl acetate-CH$_2$Cl$_2$ to yield 455 mg of pure product, an off-white solid. (87%). M.p.: 152°–154° C.; HRMS: C: 413.0909; F: 413.0949; $^1$H NMR (AC 300, CDCl$_3$): δ3.84 (s, 3H); IR (cm$^{-1}$): 3170 broad, 1660.

EXAMPLE 31

Synthesis of N-(3-(7-hydroxy-1-oxo-1,2,3,4-tetrahydronaphthalen-2-ylmethyl)phenyl]-trifluoromethanesulfonamide A mixture of 439 mg (1.06 mmol) of the product of Example 30 in 8 mL 48% HBr and 8 mL acetic acid was heated to reflux for 75 minutes under N$_2$. The reaction mixture was cooled to room temperature, diluted with 300 mL H$_2$O, pH adjusted to 3–4 using 2N NaOH, and extracted with twice with 150 mL ethyl acetate. The ethyl acetate extracts were combined and washed once with brine and then dried over Na$_2$SO$_4$. Filtration, concentration and drying yielded 0.42 g of tan solid, which was purified by silica gel chromatography (4% methanol-CH$_2$Cl$_2$) to yield 357 mg of pure product, an off-white powder. (84% yield) m.p.: 191°–194° C.; MS (LSIMS): 400 M+H, Base; $^1$H NMR (AC 300, dimethylsulfoxide-d$_6$): δ9.58 (br s, 1H, phenol OH); IR (cm$^{-1}$): 3330, 3280, 1670. Analysis calculated: C 54.13, H 4.04, N 3.51%; C 53.99, H 3.95, N 3.49%.

EXAMPLE 32

Synthesis of N-(3-(1,7-dihydroxy-1-oxo-1,2,3,4-tetrahydronaphthalen-2-ylmethyl)phenyl]-trifluoromethanesulfonamide 31 mg (0.829 mmol) of sodium borohydride were added in one portion to a −55° C. solution of 331 mg (0.829 mmol) of the title compound of Example 31 and 340 mg (0.912 mmol) of cerium (111) chloride heptahydrate in 10 mL CH$_3$OH and 3 mL tetrahydrofuran. After stirring at −55° C. for 40 minutes, the reaction mixture was allowed to warm to room temperature. The reaction mixture was then concentrated in vacuo, the residue diluted with 150 mL ethyl acetate, and then washed twice with saturated NH$_4$Cl, once with H$_2$O and once with brine and then dried over Na$_2$SO$_4$.

Filtration, concentration and drying in vacuo yielded 0.39 g of a white foam, which was purified by silica gel chromatography (2% $CH_3OH/CH_2Cl_2$–5%) to afford 209 mg of pure product, a white foam. (63% yield) HRMS: C: 401.0909; F: 401.0864; $^1H$ NMR (AC 300, dimethylsulfoxide-$d_6$): δ9.04 (br s, 1H); 4.23 (d, 1H, J=2.9 Hz); IR ($cm^{-1}$): 2800–3600, 1615.

EXAMPLE 33

Synthesis of N-(3-(7-((5-fluorobenzothiazol-2ylmethoxy)methoxy)-1-hydroxy-1,2,3,4-tetrahydronaphthalen-2-ylmethyl)phenyl]-trifluoromethanesulfonamide 119 mg (0.591 mmol) of (5-fluorobenzothiazol-2-yl) methyl chloride were added to a room temperature suspension of 190 mg (0.473 mmol) of the title compound of Example 32) and 196 mg (1.42 mmol) of $K_2CO_3$ in 4 mL of anhydrous dimethylformamide. After 24 hours at room temperature, the reaction mixture was diluted with about 100 ml of 0.1N HCl, and extracted three times with ethyl acetate. The ethyl acetate extracts were combined, washed once with $H_2O$ and once with brine and then dried over sodium sulfate. Filtration, concentration and drying in vacuo gave 0.36 g of a brown oil, which was purified by silica gel chromatography (1% $CH_3OH$—$CH_2Cl_2$) to yield 126 mg of pure product, a yellow foam. (47%). Recrystallization from ethyl acetate-hexane yielded 108 mg of yellow needles. M.p.: 172°–174° C.; MS (LSIMS): 567 M+H, 549 Base; $^1H$ NMR (AC 300, Acetone-$D_6$): δ5.51 (s, 2H); 4.46 (m, 1H); 4.03 (m, 1H); IR ($cm^{-1}$): 3590, 1390. Analysis calculated: C 55.11, H 3.91, N 4.94%; found: C 55.05, H 3.86, N 4.87%.

EXAMPLE 34

6-Hydroxychroman-4-one

A mixture of 50.0 g (281 mmol) of 6-methoxychroman-4-one in 350 mL 48% HBr and 350 mL acetic acid was heated to reflux under $N_2$. After 4 hours, the reaction mixture was cooled to room temperature in a Rotovap (trademark) and 1 L $H_2O$ was added. The suspension was kept at 0° C. overnight. The mixture was filtered, and the precipitate washed two times with $H_2O$, two times with hexanes and then dried under vacuum to give 43.0 g of the title product as a dark purple/black solid. 93% yield.

TLC: $R_f$ 0.45 in 5% $CH_3OH$ in —$CH_2Cl_2$

EXAMPLE 35

6-Benzyloxychroman-4-one

A mixture of 42.9 g (261 mmol) of the title product of Example 34, 48.7 g (352 mmol) of $K_2CO_3$, and 32.0 mL (269 mmol) of benzyl bromide in 250 mL acetone was heated to reflux under $N_2$. After 20 hours, the reaction mixture was cooled to room temperature, diluted with 1.5 L ethyl acetate, and filtered through Celite (trademark). The filtrate was concentrated, chromatographed (one time with $CH_2Cl_2$, one time with 1:3 ethyl acetate-hexanes) on silica gel, and triturated with 10% diethyl ether in hexanes to give 58.37 g of the title product as a tan powder. 88% yield.

$^1H$ NMR (300 m Hz, $CDCl_3$): δ5.05 (s, 2H); 4.5 (t, 2H); 2.79 (t, 2H). MS (Cl, $NH_3$): 255 M+H, Base.
Mp: 108°–110° C.

EXAMPLE 36

3-Formyl-4-hydroxybenzoic acid 140 g (1.01 mol) of 4-hydroxybenzoic acid were added to a hot solution of 250 g (6.25 mol) of sodium hydroxide in 500 mL $H_2O$. 150 mL of $CHCl_3$ were cautiously added to the hot solution, and after the foaming had ceased, the reaction mixture was stirred overnight at room temperature. The reaction mixture was then diluted to 4 L with $H_2O$, acidified to pH 1 by addition of about 300 mL of concentrated HCl, and extracted two times with 2 L and then three times with 1 L ethyl ether. The ether extracts were combined and a solution of 750 g sodium bisulfite in 3 L $H_2O$ was added. This mixture was stirred thoroughly for 2 minutes, then the layers were separated and the aqueous layer was extracted two times with 500 ml ethyl ether. The aqueous layer was acidified by slow addition of a solution of 230 mL concentrated $H_2SO_4$ in 230 mL $H_2O$. Vigorous $SO_2$ evolution was noted. The solution was then heated on a steam bath, and a stream of $N_2$ was blown through the hot solution for about 15 minutes until a large amount of crystals formed. The mixture was allowed to stand at room temperature overnight, then cooled to –10° C. for ½0 hour, then filtered. The crystals were washed two times with $H_2O$ and then dried under vacuum to yield 38.46 g of the title product as a tan powder. 23% yield.

$^1H$ NMR (300 m Hz, DMSO-$d_6$): δ10.3 (s, 1H). MS (Cl, $NH_3$): 183 M+17, 166 (M+), 165 Base.
Mp: 247°–249° C.

EXAMPLE 37

3-Formyl-4-methoxybenzoic acid methyl ester 24.8 mL (398 mmol) of methyl iodide were added dropwise to a room temperature suspension of 30.0 g (181 mmol) of 3-formyl-4-hydroxybenzoic acid (from Example 36) and 75 g (542 mmol) of $K_2CO_3$ in 250 mL of dry dimethylformamide (DMF). After stirring 4 hours at room temperature, the reaction mixture was diluted with 2 L $H_2O$ and extracted four times with 750 mL ethyl acetate. The ethyl acetate extracts were washed three times with 500 mL $H_2O$, one time with 300 mL 1N NaOH, one time with 500 mL $H_2O$, one time with 250 mL brine, and dried over $Na_2SO_4$. Filtration, concentration of filtrate and drying under vacuum gave 20.35 g of pure product as pale yellow needles. 58% yield.

$^1H$ NMR (300 m Hz, $CDCl_3$): δ4.01 (s, 3H); 3.90 (s, 3H).
Mp: 98°–102° C.

EXAMPLE 38

3-(6-Benzyloxy-4-oxochroman-3-ylidenemethyl)-4-methoxybenzoic acid methyl ester 19.1 g (98.3 mmol) of 3-formyl-4-methoxybenzoic acid methyl ester (from Example 37) were added to a room temperature suspension of 25.0 g (98.3 mmol) of 6-benzyloxychroman-4-one and 8.21 mL (98.3 mmol) of pyrrolidine in 350 mL $CH_3OH$. After stirring 20 hours at room temperature, the reaction mixture was filtered, washed two times with $CH_3OH$ and the precipitate dried under vacuum to give 33.93 of the title product as a yellow powder. Mp: 167°–169° C. 80% yield. $^1H$ NMR (300 m Hz, $CDCl_3$): δ3.93 (s, 3H); 3.91 (s, 3H); 12 aromatic resonances δ6.8→8.1.

EXAMPLE 39

3-(6-Benzyloxy-4-oxochroman-3-ylmethyl)-4-methoxybenzoic acid methyl ester

A mixture of 33.9 g (78.8 mmol) of the product of Example 38 and 3 g of 10% Pd/C in 500 mL tetrahydrofuran (THF) and 500 mL ethyl acetate was placed on a Parr (trademark) shaker and hydrogenated at 20 psi $H_2$ at room temperature. After 40 minutes the reaction mixture was filtered though Celite, and the filtrate concentrated on a Rotovap. The residue was purified by silica gel chromatography (2 columns, first $CH_2Cl_2$, then 1:3 ethyl acetate:hexanes) to give 19.6 g of pure product, a pale yellow solid. 67% yield.

$^1$H NMR (300 m Hz, $CDCl_3$): δ5.05 (s, 2H); 3.89 (s, 3H); 3.86 (s, 3H) MS (LSIMS): 433 M+H, Base.

EXAMPLE 40 cis-(±)-3-(6-Benzyloxy-4-hydroxychroman-3-ylmethyl)-4-methoxybenzoic acid methyl ester 1.71 g (45.3 mmol) of sodium borohydride were added in one portion to a −50° C. solution of 19.6 g (45.3 m mmol) of $CeCl_3 \cdot 7 H_2O$ in 250 mL $CH_3OH$ and 700 mL THF. After 1.5 hours, the reaction mixture was warmed to room temperature and concentrated to remove half of the solvent. The residue was diluted with 2.5 L ethyl acetate, washed two times with 500 mL saturated $NH_4Cl$, one time with $H_2O$, one time with brine, and dried over $Na_2SO_4$. Filtration, concentration and drying afforded 20.8 g of an off-white foam, which was purified on a silica gel column (1:3 to 1:2 ethyl acetate:hexanes) to yield 15.77 g of the title product as a white crystalline solid. Mp: 133°–135° C. 80% yield. $^1$H NMR (300 m Hz, $CDCl_3$): δ4.35 (t, 1H); 3.91 (s, 3H); 3.88 (s, 3H). MS (LDIMD): 434 m+, 179 Base.

EXAMPLE 41

(+)-2-t-Butoxycarbonylamino-3-(1H-indol-3-yl) propionic acid methyl-3-6-benzyloxy-4-hydroxychroman-3-ylmethyl)-4-methoxybenzoate ester 9.74 g (50.8 mmol) of 1-ethyl-3-(3-dimethylaminopropyl) carbodiimide were added to a room temperature solution of 15.75 g (36.3 mmol) of the product of Example 40, 15.46 g (50.8 mmol) of t-Boc-D-tryptophan, and 6.21 g (50.8 mmol) of 4-dimethylaminopyridine (DMAP) in 250 mL $CH_2Cl_2$. After 18 hours at room temperature, the reaction mixture was concentrated on a Rotovap, the residue dissolved in 2 L ethyl acetate, then washed two times with 250 mL 1N HCl, two times with 250 mL 1N NaOH, one time with 250 mL $H_2O$, one time with 500 mL brine, then dried over $MgSO_4$. Filtration, concentration and drying gave 35 g of impure product, which was purified on a silica gel column (5% ethyl acetate in $CH_2Cl_2$) to give 11.96 g of pure product as a white amorphous foam. 46% yield (92% of theory).

$^1$H NMR (300 m Hz, $CDCl_3$): δ3.89 (s, 3H); 3.82 (s, 3H); 1.47 (s, 9H). MS (EI): 720 M+, 179 Base. $[α]_D$: +135°, C=0.750, $CHCl_3$.

EXAMPLE 42 cis-(+)-3-(6-Benzyloxy-4-hydroxychroman-3-ylmethyl)-4-methlxybenzoic acid

A mixture of 11.89 g (16.5 mmol) of the product of Example 41 in 250 mL $CH_3OH$ and 75 mL 1N NaOH was heated to reflux. After 1 hour, the reaction mixture was cooled to room temperature and concentrated to about ⅓ of its volume on a Rotovap. The residue was diluted with 1.5 L $H_2O$, acidified to pH 1–2 with 1N HCl, and extracted two times with 500 mL ethyl acetate. The ethyl acetate extracts were combined, washed one time with 300 mL $H_2O$, one time with 300 mL brine and dried over $MgSO_4$. Filtration, concentration and drying gave 13.0 g of a white foam, which was purified on a silica gel column (5% $CH_3OH$ in $CH_2Cl_2$) to yield 6.30 g of the title product as a white crystalline solid. 91% yield.

$^1$H NMR (300 m Hz, DMSO-$d_6$): δ4.99 (s, 2H); 3.84 (s, 3H). MS (EI): 420 m+, 165 Base. $[α]_D$: +84.0°, c=0.535 (THF).

Mp: 130°–134° C.

EXAMPLE 43

(+)-N-[3-{4-Hydroxy-6-benzyloxychroman-3-ylmethyl}-4-methoxyphenyl]benzoxamide 2.44 mL (11.3 mmol) of diphenylphosphorylazide were added in one portion to a room temperature solution of 4.53 g (10.8 mmol) of the product of Example 42, 1.23 mL (11.9 mmol) of benzyl alcohol, and 3.31 mL (23.8 mmol) of triethylamine in 50 mL in 1,4-dioxane. The reaction mixture was heated to reflux and stirred for 24 hours, at which point it was cooled to room temperature and concentrated on a Rotovap. The residue was diluted with 600 mL ethyl acetate, washed three times with $H_2O$, one time with brine, and dried over $Na_2SO_4$. Filtration, concentration and drying gave 6.0 g of a yellow oil, which was purified on a silica gel column (1:3 ethyl acetate:hexanes) to afford 3.55 g of the title product as a white amorphous foam. 63% yield.

$^1$H NMR (300 m Hz, $CDCl_3$): δ5.18 (s, 2H); 4.95 (AB doublet, 2H); 3.84 (s, 3H). MS (CI, $NH_3$): 526 M+H, 400 Base. $[α]_D$: +82.9°, c=0.764 ($CHCl_3$).

EXAMPLE 44 cis-(+)-3-(5-Amino-2-methoxybenzyl)-chroman-4,6-diol

A mixture of 3.50 g (6.66 mmol) of the product of Example 43 and 1.0 g of Pd(OH)$_2$/C (Pearlman's catalyst) in 40 mL $CH_3OH$ and 40 mL THF was placed in a Parr hydrogenator and shaken under 40 psi $H_2$ at room temperature. After 1.5 hours, the reaction mixture was filtered through Celite, concentrated, and the residue purified on a silica gel column (4%→10% $CH_3OH$ in $CH_2Cl_2$) to give 1.87 g of the title product as a white solid. 93% yield.

$^1$H NMR (300 m Hz, DMSO-$d_6$): δ8.80 (s, 1H); 3.66 (s, 3H). MS (CI, $NH_3$): 302 M+H, 284 Base. $[α]_D$: +110°, c=0.813 (THF).

The compounds of Examples 45, 46 and 47 were prepared according to the method of Examples 18 and 23 using the product of Example 44 as starting material.

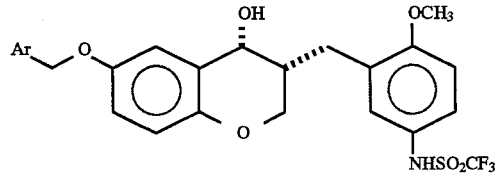

| Example | Ar | |
|---|---|---|
| 45 | 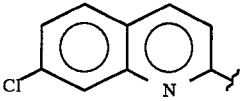 | MS (CI): 609 M + H, 204 Base<br>[α]_D: +76.2°, c = 0.307 (CHCl₃) |
| 46 | 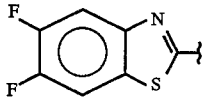 | MS(CI): 617 M + H, 204 Base<br>[α]_D: +68.8°, c = 0.464 (CHCl₃)<br><br>CHN  C: <u>C</u> 50.64  <u>H</u> 3.43  N <u>4.54</u><br>     F:    50.84    3.61     4.14 |
| 47 | 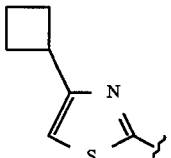 | MS (CI): 585 M + H, 154 Base<br>[α]_D: +59°, c = 0.145, (CHCl₃) |

EXAMPLE 48

The compound of Example 48 was prepared according to the method of Examples 41–44, using the diastereomer from the resolution in Example 41 as starting material.

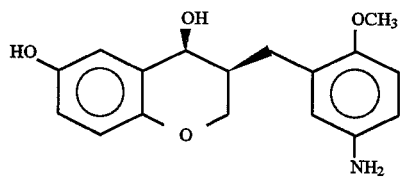

¹H NMR (DMSO-d₆): δ8.80 (s, 1H); 4.55 (br s, 2H); 4.28 (m, 1H) [α]_D: −92.0°, c=0.880 (THF)

The compounds of Examples 49 and 50 were prepared according to the method of Examples 18 and 23 using the product of Example 48 as starting material.

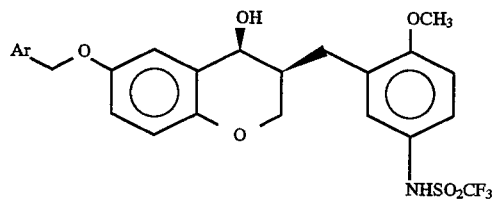

EXAMPLE 51 cis-(+)-N-{-3-[6-(7-Chloroquinolin-2-ylmethoxy)-4-hydroxychroman-3-ylmethyl]-4-methoxyphenyl}-C,C,C-trifluoromethane sulfonamide, mono sodium salt 1.81 mL (3.63 mmol) of 2N NaOH were added in one portion to a room temperature solution of 2.21 g (3.63 mmol) of the product of Example 45 in 125 mL of absolute ethanol. The reaction mixture was stirred at room temperature under N₂ for 18 hours, then was concentrated to dryness on a Rotovap and co-stripped with ether two times. The light yellow powder that formed was dissolved in hot CH₂Cl₂ and isopropyl ether was added until a white solid precipitated. The suspension was cooled to room temperature, then the crystals were filtered and dried under vacuum to yield 2.00 g of the title product as a white powder, 88% yield.

Mp: 159° (dec)

¹H NMR (300 m Hz, acetone-d₆): δ5.27 (s, 2H); 3.73 (s, 3H). MS 631 M+H, 609 Base. [α]_D=+77.7°, c=0.830 (THF).

The compounds of Examples 52–55 were prepared according to the method of Example 51.

| Example | Ar | |
|---|---|---|
| 49 | 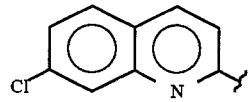 | mp: 78° (d)<br>[α]_D: −67.8°, c = 0.338 (CHCl₃)<br>MS (LSIMS): 608 M+, Base |
| 50 | 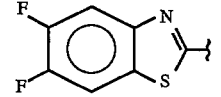 | mp: 85° (d)<br>[α]_D: −64.5°, c = 0.259 (CHCl₃)<br><br>CHN  C: <u>C</u> 50.64  <u>H</u> 3.43  N <u>4.54</u><br>     F:    50.92    3.73     4.30 |

49

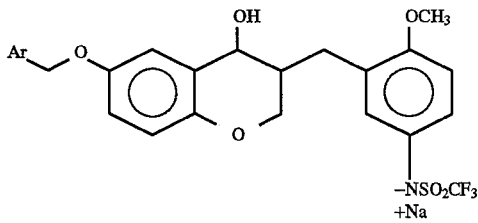

50

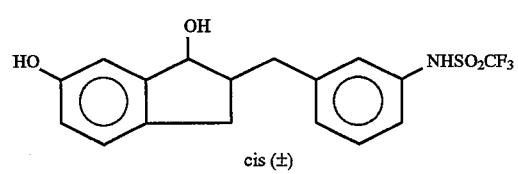

cis (±)

| Example | Ar | Stereo-chemistry | |
|---|---|---|---|
| 52 | ![F,F-benzothiazole] | cis(+) | mp: 165° (d)<br>MS: 639 M + H, 599 Base<br>[α]$_D$: +65.5°, c = 0.563 (THF) |
| 53 | ![cyclobutyl-thiazole] | cis(+) | mp: 125° (d)<br>MS: 607 M + H, 585 Base<br>[α]$_D$: +65.8°, c = 0.304 (THF) |
| 54 | ![Cl-quinoline] | cis(−) | mp: 165° (d)<br>$^1$H NMR (acetone-d$_6$): δ 5.27 (s, 2H); 3.73 (s, 3H)<br>[α]$_D$: −60.0°, c = 0.175 (THF) |
| 55 | ![F,F-benzothiazole] | cis(−) | mp: 165° (d)<br>$^1$H NMR (acetone-d$_6$): δ 5.46 (s, 2H); 3.73 (s, 3H)<br>[α]$_D$: −63.3°, c = 0.166 (THF) |

EXAMPLE 56 cis-(±)-N-[3-(1,6-Dihydroxyindan-2-ylmethyl)-phenyl]-C,C,C-trifluoromethanesulfonamide The title compound was synthesized according to the method of Examples 1–5, substituting 6-methoxy-1-indanone for 6-methoxychroman-4-one in Example 1.

| MS (Cl, NH$_3$): 405 M + 18,387 M + H, Base | | | |
|---|---|---|---|
| | C | H | N |
| CHN C: | 52.70 | 4.16 | 3.62 |
| F: | 52.31 | 4.21 | 3.38 |

EXAMPLE 57

The title compound was synthesized according to the method of Example 6, substituting the product of Example 56 for the product of Example 5 as a starting material.

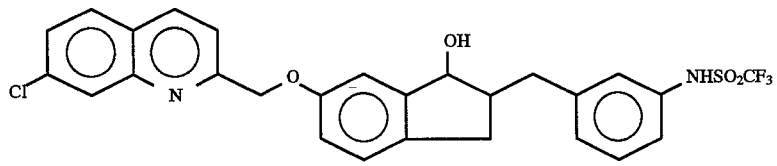

cis (±)

mp: 153–5° MS (Cl): 563 M+H, 178 Base $^1$H NMR (acetone-d$_6$): δ5.34 (s, 2H); 4.91 (d, 1H, J=4.8 Hz).

EXAMPLE 58

N-{3-[6-(5,6-Difluorobenzothiazol-2-ylmethoxy)-1-hydroxyindan-2-ylmethyl]phenyl}-C,C,C-trifluoromethane sulfonamide 382 mg (9.54 mmol) of sodium hydride, 60% oil dispersion, were added in one portion to a room temperature solution of 1.76 g (4.54 mmol) of the product of Example 56 in 30 mL of anhydrous DMF. After 20 minutes, a room temperature solution of 1.40 g (6.36 mmol) of 2-chloromethyl-5,6-difluorobenzothiazole in 10 mL of anhydrous DMF was added over 15–20 minutes. After stirring 18 hours at room temperature, the reaction mixture was poured into 500 mL $H_2O$, acidified to pH 1, and extracted two times with 300 mL ethyl acetate. The ethyl acetate extracts were combined, washed three times with 150 mL $H_2O$, one time with 100 mL brine, and dried over $Na_2SO_4$. Filtration, concentration and drying gave 3.3 g of a brown oil, which was purified by silica gel chromatography (15% to 25% ethyl acetate in $CH_2Cl_2$) to afford 1.52 g of the title product as an off-white solid. 59% yield.

Mp: 170°–2°.

|  | C | H | N |
|---|---|---|---|
| CHN C: | 52.63 | 3.36 | 4.91 |
| F: | 52.77 | 3.21 | 4.60 |

The compounds of Examples 59 and 60 were prepared according to the method of Examples 9 and 12 using the product of Example 58 as starting material.

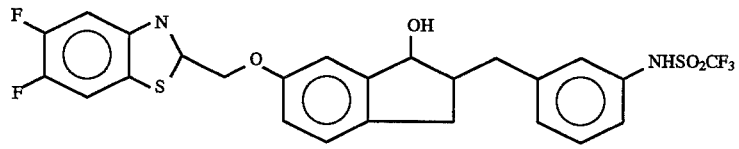

| Example | Stereochemistry | | | | |
|---|---|---|---|---|---|
| 59 | cis (−) | mp: 151–3° | | | |
| | | MS(Cl): 571 M + H, 217 Base | | | |
| | | | C | H | N |
| | | CHN C: | 52.63 | 3.36 | 4.91 |
| | | F: | 52.67 | 3.22 | 4.67 |
| | | $[\alpha]_D$: −25.7°, c = 0.534 ($CH_3OH$) | | | |
| 60 | cis (+) | mp: 151–54° | | | |
| | | MS (Cl): 571 M + H, 234 Base | | | |
| | | | C | H | N |
| | | CHN C: | 52.63 | 3.36 | 4.91 |
| | | F: | 52.64 | 3.22 | 4.94 |
| | | $[\alpha]_D$: +24.7°, c = 0.425 ($CH_3OH$) | | | |

EXAMPLE 61

The compound of Example 61 was synthesized according to the method of Examples 1–5, substituting 7-methoxy-1-tetralone for 6-methoxychroman-4-one in Example 1.

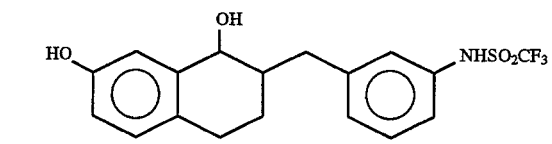

(+) cis

HRMS C: 401.0909 F: 401.0864

$^1$H NMR (DMSO-$d_6$): δ9.04 (s, 1H); 4.23 (d, 1H, J=2.9 Hz)

EXAMPLE 62 cis-(+)-N-[3-(7-Benzyloxy-1-hydroxy-1,2,3,4-tetrahydronaphth-2-ylmethyl)-phenyl]-C,C,C-trifluoromethanesulfonamide 5.4 mL (45.6 mmol) of benzyl bromide were added to a room temperature suspension of 17.42 g (43.4 mmol) of the product of Example 61 and 15.0 g (109 mmol) of $K_2CO_3$ in 750 mL of acetone. The reaction mixture was stirred at room temperature for 18 hours, then heated to reflux for 3.5 hours. The reaction mixture was cooled to room temperature, concentrated, diluted with 2 L $H_2O$, acidified to pH 1–2, and extracted three times with 1 L ethyl acetate. The ethyl acetate layers were combined, washed one time with brine and dried over $Na_2SO_4$. Filtration, concentration and drying gave 22.9 g of an off-white foam which was purified by silica gel chromatography (3% $CH_3OH$ in $CH_2Cl_2$) to afford 16.19 g of pure product as a white amorphous foam. 76% yield.

MS (Cl): 509 M+18, 491 M+, Base $^1$H NMR ($CDCl_3$): δ4.95 (br dd, 2H)

The compounds of Examples 63 and 64 were prepared according to the method of Examples 9 and 12 using the product of Example 62 as starting material.

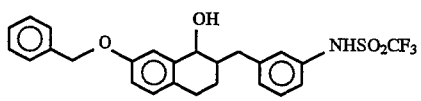

| Example | Stereochemistry | | | | |
|---|---|---|---|---|---|
| 63 | cis (+) | MS(Cl, $NH_3$): | | | |
| | | 509 M + H, 491 M+, Base | | | |
| | | $[\alpha]_D$: +48.9°, c = 0.441 ($CHCl_3$) | | | |
| | | | C | H | N |
| | | CHN C: | 61.05 | 4.92 | 2.85 |
| | | F: | 60.80 | 4.80 | 2.77 |
| 64 | cis (−) | MS (Cl, $NH_3$): | | | |
| | | 509 M + 18,491 M+, Base | | | |
| | | $[\alpha]_D$: −51.6°, c = 0.510 ($CHCl_3$) | | | |

-continued

| Example | Stereochemistry | | | |
|---|---|---|---|---|
| | | C | H | N |
| | CHN C: | 61.05 | 4.92 | 2.85 |
| | F: | 60.97 | 4.66 | 2.79 |

EXAMPLE 65 and 66

(+)-C,C,C-Trifluoro-N-[3-(7-hydroxy-1,2,3,4-tetrahydronaphth-2-ylmethyl)-phenyl]methanesulfonamide (Example 65)

and cis-(+)-N-[3-(1,7-Dihydroxy-1,2,3,4-tetrahydronaphth-2-ylmethyl)-phenyl]-C,C,C-trifluoro-methanesulfonamide (Example 66)

A mixture of 3.05 g (6.21 mmol) of the product of Example 63 and 1.2 g of 10% Pd/C in 75 mL $CH_3OH$ was placed in a Parr hydrogenation apparatus and shaken under 35 psi $H_2$ for 1 hour. The reaction mixture was filtered through Celite and concentrated to give 2.6 g of a white oily foam. Silica gel chromatography (4% to 10% $CH_3OH$ in $CH_2Cl_2$) gave 0.80 g (33% yield) of the desoxy compound as a clear oil (Example 65) and 1.51 g (61% yield) of the diol compound as a white solid (Example 66).

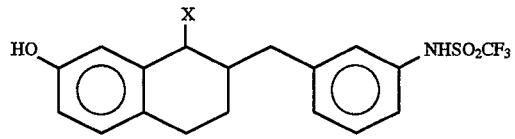

| Example | X | Stereo-chemistry | |
|---|---|---|---|
| 65 | H | (+) | MS(Cl, $NH_3$): 403 M + 18, Base |
| | | | $[\alpha]_D$: +53.8°, c = 0.416 ($CHCl_3$) |
| 66 | OH | cis (+) | mp: 167–169° |
| | | | MS (Cl, $NH_3$): |
| | | | 419, M + 18, 401 M+, Base |

| | C | H | N |
|---|---|---|---|
| CHN C: | 53.86 | 4.52 | 3.49 |
| F: | 54.20 | 4.34 | 3.41 |
| $[\alpha]_D$: +47.5°, c = 0.600 (THF) | | | |

The compounds of Examples 67 and 68 were prepared according to the methods of Examples 55 and 56 using the product of Example 64 as starting material.

| Example | X | Stereo-chemistry | |
|---|---|---|---|
| 67 | H | (−) | MS(Cl, $NH_3$): 403 M + 18, Base, 386 M + H |
| | | | $[\alpha]_D$: −53.1°, c = .0510 ($CHCl_3$) |
| 68 | OH | cis (−) | mp: 166–168° |
| | | | MS (Cl, $NH_3$): |
| | | | 419, M + 18, 401 M+, Base |
| | | | $[\alpha]_D$: −51.4°, c = 0.642 (THF) |

The compounds of Examples 69 through 76 were prepared according to the method of Example 58, substituting the products of Examples 65, 66, 67 or 68 for the product of Example 56 in Example 58.

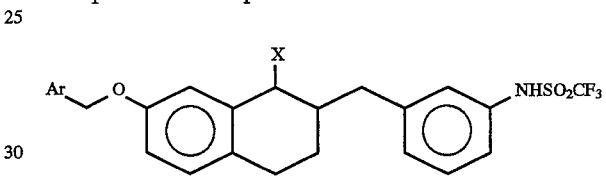

| Ex | Ar | X | Stereo-chemistry | |
|---|---|---|---|---|
| 69 |  | OH | cis (−) | MS (Cl): 585 M + H $[\alpha]_D$: −48°, c = 0.128 ($CHCl_3$) |
| 70 |  | OH | cis (−) | MS (Cl): 577 M + H, 178 Base $[\alpha]_D$: −47.4°, c = 0.152 ($CHCl_3$) |

-continued

| Ex | Ar | X | Stereo-chemistry | |
|----|----|---|------------------|---|
| 71 |  | OH | cis (+) | CHN C: C 58.28 H 4.19 N 4.86<br>F: 57.81 4.02 4.65<br>[α]_D: +50.0°,<br>c = 0.338<br>(CHCl_3) |
| 72 | 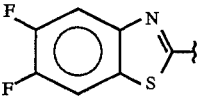 | OH | cis (+) | MS (Cl): 585 M + H<br>CHN C: C 53.41 H 3.62 N 4.79<br>F: 53.09 3.53 4.63<br>[α]_D: +42.6°, c = 0.244<br>(CHCl_3) |
| 73 | 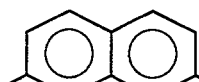 | H | (−) | mp: 197–9°<br>MS: 561 M + H, 403 Base<br>[α]_D: −49.6°, c = 0.262 (THF) |
| 74 | 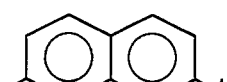 | H | (+) | mp: 197–9°<br>MS (Cl): 561 M + H, 403 Base<br>[α]_D: +50.7°, c = 0.345 (THF) |
| 75 |  | OH | cis (+) | MS (Cl): 561 M + H, 161 Base<br>$^1$H NMR (CDCl_3) δ 5.28 (s, 2H) |
| 76 |  | OH | cis (+) | MS (Cl): 553 M + H, Base<br>$^1$H NMR (CDCl_3) δ 5.26 (s, 2H),<br>3.65 (quintet, 1H) |

The compounds of Examples 77 through 84 were prepared according to the method of Example 51, except that the salts were recrystallized from ethyl acetate:hexanes and not isopropyl ether:CH_2Cl_2.

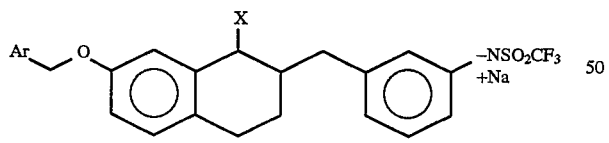

| Ex | Ar | X | Stereo-chemistry | |
|----|----|---|------------------|---|
| 77 | 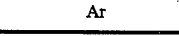 | OH | cis (−) | mp: 271–273°<br>MS: 607 M + H<br>[α]_D: −50.2°, c = 0.305 (THF)<br>CHN C: C 51.49 H 3.32 N 4.62<br>F: 51.17 3.42 4.49 |

-continued

| Ex | Ar | X | Stereo-chemistry | | | | |
|---|---|---|---|---|---|---|---|
| 78 | 6-Cl-quinolin-2-yl | OH | cis (−) | mp: 262–264° <br> $[\alpha]_D$: −57.9°, c = 0.568 (THF) | | | |
| | | | | CHN | C: | H | N |
| | | | | C: | 56.14 | 3.87 | 4.68 |
| | | | | F: | 55.48 | 3.60 | 4.58 |
| 79 | 6-Cl-quinolin-2-yl | OH | cis (+) | mp: 259–261° <br> $[\alpha]_D$: +67.0, c = 0.476 (THF) | | | |
| | | | | CHN | C | H | N |
| | | | | C: | 56.14 | 3.87 | 4.68 |
| | | | | F: | 55.27 | 3.73 | 4.42 |
| 80 | 5,6-difluorobenzothiazol-2-yl | OH | cis (+) | mp: 273–275° <br> $[\alpha]_D$: +52°, c = 0.250 (THF) <br> $^1$H NMR (DMSO-$d_6$) δ 5.53 (s, 2H) | | | |
| 81 | 6-Cl-quinolin-2-yl | H | (−) | mp: 90–100° (d) <br> $[\alpha]_D$: −43.7°, c = 0.611 (THF) <br> IR (cm$^{-1}$): 2920, 1610, 1500 | | | |
| 82 | 6-Cl-quinolin-2-yl | H | (+) | mp: 100–110° (d) <br> $[\alpha]_D$: −48.9°, c = 0.568 (THF) <br> IR (cm$^{-1}$): 2920, 1610, 1500 | | | |
| 83 | 6-F-quinolin-2-yl | OH | cis (+) | mp: 278–279° <br> $[\alpha]_D$: +57.6°, c = 0.917 (THF) | | | |
| | | | | CHN | C | H | N |
| | | | | C: | 57.72 | 3.98 | 4.81 |
| | | | | F: | 57.23 | 3.74 | 4.73 |
| 84 | 5-cyclobutylthiazol-2-yl | OH | cis (+) | mp: 272–274° <br> $[\alpha]_D$: +49.3, c = 0.615 (THF) | | | |
| | | | | CHN | C | H | N |
| | | | | C: | 54.34 | 4.56 | 4.88 |
| | | | | F: | 54.16 | 4.10 | 4.72 |

The compounds of Examples 85 and 86 were prepared according to the method of Example 51, except the salts were triturated with petroleum ether and not recrystallized from isopropyl ether:CH$_2$Cl$_2$.

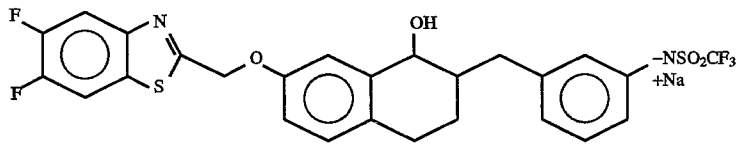

| Example | Stereochemistry | |
|---|---|---|
| 85 | cis (+) | mp: 120° + (d)<br>[α]$_D$: +23.2°, c = 1.011 (CH$_3$OH)<br>IR (cm$^{-1}$): 3350, 2940, 1475 |
| 86 | cis (−) | mp: 120° + (d)<br>[α]$_D$: −22.6°, c = 0.936 (CH$_3$OH)<br>IR (cm$^{-1}$): 3350, 2940, 1475 |

EXAMPLE 87 cis-N-{3-[6-(7-Chloroquinolin-2-ylmethoxy)-4-hydroxychroman-3-ylmethyl]-4-hydroxyphenyl}-C,C,C-trifluoromethanesulfonamide 3.46 mL (3.46 mmol) of 1.0M BBr3 in CH$_2$Cl$_2$ were added to a −78° C. solution of 702 mg (1.15 mmol) of the product of Example 35 in 70 mL of anhydrous CH$_2$Cl$_2$. The reaction was allowed to stir under N$_2$ and warm to room temperature overnight. After 16 hours, the reaction mixture was chilled in an ice bath and 50 mL of H$_2$O were added dropwise. After stirring 15 minutes at 0° C., the mixture was extracted three times with 150 mL ethyl acetate. The ethyl acetate extracts were combined, washed two times with 100 mL H$_2$O, one time with 100 mL brine, and dried over Na$_2$SO$_4$. Filtration, concentration and drying gave 0.75 g of a yellow-tan foam, which was purified on a silica gel column (2 to 4% CH$_3$OH in CH$_2$Cl$_2$) to afford 48 mg of pure product, a white foam. (7% yield).

$^1$H NMR (acetone-d$_6$): δ5.26 (s, 2H); 4.0 (m, 2H).
Mp: 126°–133° (d). MS (Cl): 595 M+H, 147 Base.

EXAMPLE 88

N-[4-Chloro-3-(6-hydroxy-4-oxochroman-3-ylmethyl)phenyl]-C,C,C-trifluoromethanesulfonamide This compound was prepared according to the sequence which afforded the product of Example 4 starting with 2-chloro-5-nitrobenzaldehyde instead of 3-nitrobenzaldehyde. After column chromatography (silica gel, 7% methanol in methylene chloride) final product was obtained in 84% yield as a colorless oil. $^1$H NMR (DMSO-d$_6$): δ2.75 (dd, 1H); 3.0 (m, 1H); 3.30 (dd, 1H); 4.30 (m, 2H). MS (Cl, NH$_3$) m/e: 453 (M$^+$+18); IR (KBr): 3640, 3260, 1680 cm$^{-1}$.

EXAMPLE 89

N-{4-Chloro-3-[6-(5,6-difluorobenzothiazol-2-ylmethoxy)-4-oxochroman-3-ylmethyl]phenyl}-C,C,C-trifluoromethane sulfonamide To a stirred solution of 1.45 g (3.33 mmol) of the product of Example 88 in dimethylformamide (30 mL) was added 1.4 g (9.98 mmol) potassium carbonate. The mixture was stirred at room temperature for 20 minutes, then 877 mg (4.0 mmol) 2-(chloromethyl)-5,6-difluorobenzothiazole was added and the mixture stirred at room temperature for 3 days. The mixture was poured into water, acidified to ph 1–4 with 1N HCl and extracted with ethyl acetate. The ethyl acetate extract was washed with water and brine, dried, and concentrated to give an oil. Flash chromatography on silica gel eluting with 2.5% methanol in dichloromethane afforded 1.96 g (95%) of the title product as a foam. NMR (CDCl$_3$): δ2.75 (dd, 1H); 3.10 (m, 1H); 3.40 (dd, 1H); 4.20 (dd, 1H); 4.40 (dd, 1H); 5.40 (s, 2H); MS (Cl, NH$_3$) m/e: 619 (M+) 615 (25), 597 (30), 453 (40), 414 (40), 348 (100); IR (CHCl$_3$): 1680 cm$^{-1}$.

EXAMPLE 90

(±)-N-{4-Chloro-3-[6-(5,6-difluorobenzothiazol-2-ylmethoxy)-4-cis-hydroxychroman-3-yl-methyl]phenyl}-C,C,C-trifluoro-methane sulfonamide To a stirred solution of 1.9 g (3.07 mmol) of the product of Example 89 and 2.3 g (6.14 mmol) cerium III chloride heptahydrate in methanol (15 mL) and tetrahydrofuran (15 mL) at −50° C. was added 232 mg (6.14 mmol) sodium borohydride. The mixture was stirred at −50° C. for 30 minutes, then poured into water, acidified to ph 1–4 with 1N HCl, and extracted with ethyl acetate. The ethyl acetate extract was, washed with water, brine, dried, and concentrated in vacuo to give an oil. Flash chromatography on silica gel eluting with 5% methanol in dichloromethane gave 1.6 g (84%) of the title product as a foam. NMR (CDCl$_3$): δ2.40 (m, 1H); 2.80 (dd, 1H); 2.95 (dd, 1H); 4.05 (d, 2H); 4.40 (m, 1H); 5.30 (s, 2H). MS (LSIMS) m/e: 620 (M+), 603 (100). IR (CHCl$_3$): 3380 cm$^{-1}$.

EXAMPLE 91

Resolution of (±)-N-{4-chloro-3-[6-(5,6-difluorobenzothiazol-2-ylmethoxy)-4-cis-hydroxychroman-3-yl-methyl]phenyl-C,C,C-trifluoromethanesulfonamide;

(+)-N-2-tert-Butoxycarbonylamino-1H-indol-3-yl) propionic acid 3-[2-chloro-3-[2-chloro-5-trifluoromethanesulfonylamino)benzyl]6-(5,6-difluorobenzothiazol-2-yl-methoxy)cis-chroman-4-yl ester (Compound 91A); and (−)-N-2-tert-Butoxycarbonylamino-3-(1H-indol-3-yl)-propionic acid-3-[2-chloro-3-[2-chloro-5-(trifluoromethanesulfonylamino)benzyl]-6-(5,6-difluorobenzothiazol-2-yl-methoxy)cis-chroman-4-yl ester (Compound 91 B)

These compounds were obtained following the procedure described for compounds 9A and 9B (Example 9). Purification on a silica gel column eluting with 2.5% methanol in methylene chloride gave compounds (91A) (less polar) and (91B) (more polar) as a white foamy solid. Compound (91A) (less polar). NMR (CDCl$_3$): δ1.45 (s, 9H); 2.55 (t, 1H), 2.95 (m, 1H); 3.05 (dd, 1H); 3.20 (dd, 1H); 3.30 (dd, 1H); 3.50 (s, 1H); 4.05 (t, 1H); 4.30 (dd, 1H); 4.65 (m, 1H); 5.05 (m, 1H); 5.20 (q, 2H); 5.30 (s, 1H). MS (LSIMS) m/e: 906 (M$^+$, 1), 603 (100).

Compound (91B) (more polar): NMR (CDCl$_3$): δ1.50 (s, 9H); 2.45 (m, 1H); 2.70 (m, 2H); 2.80 (m, 2H); 4.00 (m, 1H); 4.50 (m, 1H); 5.10 (d, 1H); 5.30 (s, 2H); 5.60 (s, br, 1H). MS (LSIMS) m/e: 603 (M$^+$-BOC-Try-OH, 100).

EXAMPLE 92

(+)-N-{4-Chloro-3-[6-(5,6-difluorobenzothiazol-2-ylmethoxy)-4-cis-hydroxychroman-3-yl-methyl] phenyl}-C,C,C-trifluoromethanesulfonamide Following the hydrolysis procedure described for compound 9A (Example 12), the compound of Example 92 was obtained in 84% yield. Mp: 129°–131° [α]$_D$=+51.4° c=0.28 (CH$_3$OH).

EXAMPLE 93

(−)-N-{4-Chloro-3-[6-5,6-difluorobenzothiazol-2-ylmethoxy)-4-cis-hydroxychroman-3-yl-methyl] phenyl-C,C,C-trifluoromethanesulfonamide Following the hydrolysis procedure described for compound 9B (Example 13), the compound of Example 93 was obtained in 51% yield. Mp: 128°–130° [α]$_D$=−48.6°, c=0.60 (CH$_3$OH).

EXAMPLE 94

(+)-N-{4-Chloro-3-[6-(5,6-difluorobenzothiazol-2-ylmethoxy)-4-cis-hydroxychroman-3-yl-methyl]phenyl-C,C,C-trifluoromethanesulfonamide sodium salt dihydrate A mixture of 178 mg (0.29 mmol) of the product of Example 92 and 1.0N sodium hydroxide in methanol (3 mL) was stirred at room temperature for 2 hours. The mixture was concentrated and dried in vacuo then crystallized from

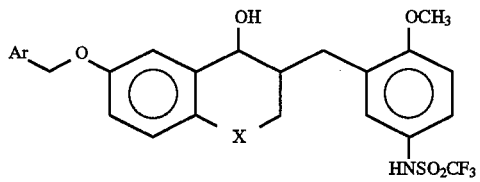

| Ex. | X | Ar | Stereo-chemistry | |
|---|---|---|---|---|
| 96 | O | 7-chloroquinolin-2-yl | (±) | NMR (CDCl$_3$): δ 2.40 (m, 1H); 2.80 (m, 1H); 2.90 (m, 1H); 4.05 (d, 2H); 4.40 (d, 1H); 5.20 (s, 2H). MS (LSIMS) M$^+$613. |
| 97 | O | 7-chloroquinolin-2-yl | (+) | NMR (DMSO-d$_6$): δ 2.10 (m, 1H); 2.45 (m, 1H); 2.75 (dd, 1H); 3.90 (m, 2H); 4.44 (s, 1H); 5.30 (s, 2H). [α]$_D$: +66.9° c = 0.32 (CH$_3$OH) |
| 98 | CH$_2$ | 5,6-difluorobenzothiazol-2-yl | (±) | NMR (DMSO-d$_6$): δ 1.45 (m, 1H); 1.75 (m, 1H); 1.90 (m, 1H); 2.50 (m, 1H); 2.70 (m, 1H); 2.90 (m, 1H); 4.35 (d, 1H); 5.53 (s, 2H). mp: 143–145° C. |
| 99 | CH$_2$ | 5,6-difluorobenzothiazol-2-yl | (+) | [α]$_D$: +47.3° c = 20.57 (CH$_3$OH). NMR (DMSO-d$_6$): δ 1.50 (m, 1H); 1.70 (m, 1H); 1.90 (m, 1H); 2.50 (m, 2H); 2.80 (m, 2H); 4.40 (s, 1H); 5.50 (s, 2H). | isopropyl ether/dichloromethane to afford 125 mg (68%) of the title product as a white solid. Mp 175°–180° C. NMR (DMSO-d$_6$): δ2.10 (m, 1H); 2.45 (dd, 1H); 2.80 (dd, 1H); 3.90 (m 2H); 4.40 (s, 1H); 5.50 (s, 2H). MS (LSIMS) m/e: 664 (M$^+$+Na, 100), 642 (M+, 75).

IR (KBr): 3200 cm$^{-1}$. [α]$_D$=+57.5°, c=0.3 (CH$_3$OH).

Calculated for C$_{25}$H$_{17}$N$_2$S$_2$O$_5$ClF$_5$Na·2H$_2$O: C, 44.22; H, 3.12; N, 4.13. Found: C, 44.64; H, 3.16; N, 4.31.

EXAMPLE 95

(−)-N-{4-Chloro-3-[6-5,6-difluorobenzothiazol-2-ylmethoxy)-4-cis-hydroxychroman-3-yl-methyl]phenyl}-C,C,C-trifluoromethanesulfonamide sodium salt dihydrate This compound was prepared according to the method of Example 94. [α]$_D$: −54.7°, c=0.28 (CH$_3$OH). NMR (DMSO-d$_6$): δ2.10 (m, 1H); 2.45 (m, 1H); 2.80 (dd, 1H); 3.90 (m, 2H); 4.40 (m, 1H); 5.50 (s, 2H).

The compounds of Examples 96 through 99 and their corresponding sodium salts were prepared according to the methods of Examples 88 through 94 using appropriate starting material and/or intermediates.

EXAMPLE 100

6-Benzyloxy-2,2-dimethylchroman-4-one

A mixture of 25.0 g (0.103 mole) 2-hydroxy-5-benzyloxyacetophenone, 8 mL (6.0 g, 0.130 mole) acetone and 4 mL (3.7 g, 0.052 mole) pyrrolidine in 100 mL toluene was stirred at room temperature for 4 hours, then refluxed over a Dean-Stark trap for 3 hours. An additional 8 mL (6.0 g, 0.130 mole) acetone and 4 mL (3.7 g, 0.052 mole) pyrrolidine was added and the mixture refluxed for 18 hours. The mixture was concentrated, poured into water, basified to pH 8 with ammonium hydroxide, then extracted with ether. The ether extract was washed successively with 1N KOH, 1N HCl, water and brine, then dried (MgSO$_4$) and concentrated to give an oil. Flash chromatography on silica gel eluting with 20% ethyl acetate in hexanes afforded a solid. Recrystallization from ethyl acetate in hexanes afforded a solid. Recrystallization from ethyl acetate in hexanes yielded the title product as a solid 13.6 g (47%), mp 105°–107° C. NMR (CDCl$_3$): δ1.4 (s, 6H); 2.7 (s, 2H); 5.1 (s, 2H).

Analysis calculated for C$_{18}$H$_{18}$O$_3$: C, 76.57; H, 6.43. Found: C, 76.16; H, 6.42.

EXAMPLE 101

6-Benzyloxy-3-(2-methoxy-5-nitrobenzylidene)-2,2-dimethylchroman-4-one

A mixture of 5.0 g (17.7 mmole) of the product of Example 100, 1.1 g (19 mmol) potassium fluoride, 3.5 g (19.5 mmole) 2-methoxy-5-nitrobenzaldehyde and 2.9 mL (2.97 g, 19.5 mmole) tetramethylortho-silicate in 15 mL dimethylformamide was heated at 80° C. for 7 hours. The mixture was poured into water and extracted with ethyl acetate. The ethyl acetate extract was and washed successively with 1N HCl, 5% NaHCO$_3$, water and brine and then dried (MgSO$_4$) and concentrated to give an oil. Flash chromatography on silica gel eluting with 30% ethyl acetate in hexanes gave 6.23 g (79%) of a foam. Recrystallization from ethyl acetate in hexanes yielded the title product as a solid m.p. 110°–112° C. NMR (CDCl$_3$): δ1.70 (s, 6H); 3.82 (s, 3H); 5.02 (s, 2H). Analysis calculated for C$_{20}$H$_{23}$NO$_6$: C, 70.10; H, 5.20; N, 3.14. Found: C, 70.19; H, 5.21; N, 3.14.

EXAMPLE 102

3-(5-Amino-2-methoxybenzyl)-6-hydroxy-2,2-dimethylchroman-4-one

A mixture of 6.2 g (13.91 mmole) of the product of Example 101, 1.2 g 5% palladium on carbon in 50 mL ethyl acetate and 10 mL methanol was shaken in a Parr hydrogenator under 20 psi hydrogen for 3 hours. The mixture was filtered through Celite and the filtrate concentrated to give an oil. Flash chromatography on silica gel eluting with 70% ethyl acetate in hexanes gave 4.6 g of an oil (100%). NMR (CDCl$_3$): δ1.44 (d, 6H); 2.75 (m, 1H); 2.95 (m, 2H); 3.70 (s, 3H). MS (CI, NH$_3$) m/e: 345 (M$^+$+18), 328 (M$^+$+1, 100).

EXAMPLE 103

3-(5-Amino-2-methoxybenzyl)-6-(5,6-difluorobenzothiazol-2-ylmethoxy)-2,2-dimethylchroman-4-one To a stirred solution of 2.36 (7.21 mmole) of the product of Example 102 in 25 mL DMF at 0° C. was added 332 mg (8.29 mmole) 60% sodium hydride. The mixture was stirred at 0° C. then a solution of 2.06 g (9.37 mmole) 2-(chloromethyl)-5,6-difluorobenzothiazole in 15 mL DMF was added dropwise. The mixture was slowly warmed to room temperature and stirred for 18 hours. The mixture was poured into water and then extracted with ethyl acetate. The ethyl acetate extract was washed successively with 1N KOH, water and brine and then dried (MgSO$_4$) and concentrated to give an oil. Flash chromatography on silica gel eluting with 50% ethyl acetate in hexanes gave 2.3 g (62%) of the title product as a solid. NMR (CDCl$_3$): δ1.45 (d, 6H); 2.90 (m, 3H); 3.69 (s, 3H); 5.39 (s, 2H). MS (CI, NH$_3$) m/e: 528 (M$^+$+18), 511 (M$^+$+1,100).

EXAMPLE 104

N-{3-[6-(5,6-Difluorobenzothiazol-2-ylmethoxy)-2,2-dimethyl-4-oxochroman-3-ylmethyl]-4-methoxyphenyl}-C,C,C-trifluoromethane sulfonamide To a stirred solution of 2.25 g (440 mmole) of the product of Example 103 and 0.8 mL (558 mg, 5.51 mmole) triethylamine in 20 mL dichloromethane at 0° C. was added 0.9 mL (1.6 g, 5.51 mmole) trifluoromethanesulfonic (triflic) anhydride. The mixture was stirred at 0° C. for 1 hour, then concentrated to give an oil. The oil was dissolved in 20 mL methanol and 10 mL tetrahydrofuran then 4 mL of 5N NaOH (22.0 mmole) was added at 0° C. The mixture was warmed to room temperature and stirred for 1 hour, then poured into water, acidified to ph 1–4 with 1N HCl, and extracted with ethyl acetate. The ethyl acetate extract was, washed with water and brine and then dried (MgSO$_4$) and concentrated to give an oil. Flash chromatography on silica gel eluting with 30% ethyl acetate in hexanes yielded 2.25 g (80%) of a solid. Recrystallization from ethyl acetate in hexanes yielded a pure product, m.p. 198°–200° C. NMR (DMSO-d$_6$): δ1.37 (d, 6H); 2.80 (m, 3H); 3.62 (s, 3H). Analysis calculated for C$_{28}$H$_{23}$N$_2$S$_2$O$_6$F$_5$: C, 52.33; H, 3.61; N, 4.36. Found: C, 52.36; H, 3.72; N, 4.03.

EXAMPLE 105

(±)-N-{-3-[6-(5,6-Difluorobenzothiazol-2-ylmethoxy)-cis-4-hydroxy-2,2-dimethylchroman-3-ylmethyl]-4-methoxyphenyl}-C,C,C-trifluoromethanesulfonamide.

To a stirred solution of 1.36 g (2.12 mole) of the product of Example 104 in 20 mL tetrahydrofuran at −78° C. was added dropwise 4.7 mL (4.66 mL) 1.0M LiB(C$_2$H$_5$)$_3$H in THF (Super-Hydride [trademark]). The mixture was allowed to come to room temperature over 3 hours, then quenched with 10 mL 10% ammonium chloride. The mixture was poured into water, acidified to ph 1–4 with 1N HCl and then extracted with ethyl acetate. The ethyl acetate extract was washed with water and brine, dried (MgSO$_4$) and concentrated to give an oil. Flash chromatography on silica gel eluting with 30% ethyl acetate in hexanes gave 670 mg (48%) of pure product. NMR (CDCl$_3$): δ1.40 (s, 3H); 1.53 (s, 3H); 2.10 (m, 1H); 2.90 (m, 2H); 3.88 (s, 3H); 4.23 (s, br, 1H); 5.29 (s, 2H). MS (LSIMS) m/e: 644 (M+, 12), 627 (32), 268 (100).

EXAMPLE 106

(+)-N-2-tert-Butoxycarbonylamino-3-(1H-indol-3-yl)propionic acid 6-(5,6-difluorobenzothiazol-2-ylmethoxy)-3-[2-methoxy-5-(trifluoromethanesulfonylamino)benzyl]-2,2-dimethylchroman-cis-4-yl-ester This compound was prepared according to the method of Example 9.

NMR (CDCl$_3$): δ1.40 (s, 9H); 2.30 (m, 2H); 2.60 (m, 2H); 2.90 (m, 1H); 3.30 (m, 3H); 3.80 (s, 3H); 4.70 (m, 1H); 5.20 (m, 2H).

EXAMPLE 107

(−)-N-2-tert-Butoxycarbonylamino-3-(1H-indol-3-yl)propionic acid 6-(5,6-difluorobenzothiazol-2-ylmethoxy)-3-[2-methoxy-5-(trifluoromethanesulfonylamino)benzyl]-2,2-dimethylchroman-cis-4-yl-ester This compound was prepared according to method in Example 9.

NMR (CDCl$_3$): δ1.45 (s, 9H); 2.30 (m, 1H); 2.60 (m, 1H); 3.05 (m, 1H); 3.30 (m, 3H); 3.80 (s, 3H); 4.40 (m, 1H); 5.05 (d, 1H); 5.30 (s, 2H); 5.60 (d, 1H).

EXAMPLE 108

(+)-N-{3-(5,6-Difluorobenzothiazol-2-ylmethoxy)-cis-4-hydroxy-2,2-dimethylchroman-3-ylmethyl]-4-methoxyphenyl}-C,C,C-trifluoromethanesulfonamide This compound was prepared from the product of Example 106 according to the method of Example 12.

NMR (CDCl$_3$): δ1.40 (s, 3H); 1.53 (s, 3H); 2.10 (m, 1H); 2.90 (m, 2H); 3.88 (s, 3H); 4.20 (d, 1H); 5.32 (s, 2H). [α]$_D$: +22.8°, c=0.32 (CHCl$_3$).

EXAMPLE 109

6-Methoxy-2,2-dimethylchroman-4-one

A mixture of 48.9 g (0.294 mole) 2-hydroxy-5-methoxyacetophenone, 32 mL (0.441 mole) acetone and 12 mL (0.147 mmole) pyrrolidine in 300 mL toluene was stirred at room temperature for 3 hours, then refluxed over a Dean-Stark trap for 3 hours. An additional 32 mL (0.441 mole) acetone and 12 mL (0.147 mole) pyrrolidine was added and the mixture again refluxed over the Dean-Stark trap for 18 hours. The mixture was concentrated, poured into water, basified, and extracted with ether. The ether extract was, washed with 1N KOH, water and brine and then dried ($MgSO_4$) and concentrated to give an oil. Flash chromatography on silica gel with 20% ethyl acetate in hexanes afforded a solid. Recrystallization from ether/hexanes yielded 32.0 g (53%) of pure product. mp 71°–73° C. Analysis calculated for $C_{12}H_{14}O_3$: C, 69.89; H, 6.84. Found: C, 69.85; H, 7.08.

EXAMPLE 110

6-Methoxy-2,2-dimethyl-3-(3-nitrobenzylidene)chroman-4-one

A mixture of 7.0 g (0.034 mole) of the product of Example 109, 2.5 mL (2.6 g, 0.017 mole) tetramethyl orthosilicate, 1.9 g (0.034 mole) potassium fluoride and 5.1 g (0.034 mole) 3-nitrobenzaldehyde in 10 mL dimethylformamide was heated to 80° C. for 4 hours. The mixture was diluted with ether and washed successively with 1N HCl, 5% $NaHCO_3$, water and brine and then dried ($MgSO_4$) and concentrated to give an oil. Flash chromatography on silica gel eluting with 20% ethyl acetate in hexanes yielded an oil. Recrystallization from ether/hexanes afforded 6.9 g (60%) of the title product as a solid. Mp 103°–105° C. Analysis calculated for $C_{15}H_{17}NO_5$: C, 67.25; H, 5.05; N, 4.13. Found: C, 67.22; H, 4.87; N, 4.11.

EXAMPLE 111

3-(3-Aminobenzyl)-6-methoxy-2,2-dimethylchroman-4-one

A mixture of 7.3 g (0.0125) of the product of Example 110 and 700 mg 5% palladium on carbon in 200 mL ethyl acetate and 50 mL tetrahydrofuran was shaken in a Parr hydrogenator under 30 psi hydrogen for 3 hours. The mixture was filtered through Celite and concentrated to give an oil. Flash chromatography on silica gel eluting with 50% ethyl acetate in hexanes yielded 6.8 g (99%) of the title product as an oil. NMR ($CDCl_3$): $\delta 1.38$ (s, 3H); 1.47 (s, 3H); 2.20 (dd, 1H); 2.90 (m, 1H); 3.00 (dd, 1H); 3.60 (s, br, 2H); 3.78 (s, 3H). MS (Cl, $NH_3$) m/e: 329 ($M^+$+18), 312 ($M^+$+1,2 100).

EXAMPLE 112

C,C,C-Trifluoro-N-[3-(6-methoxy-2,2-dimethyl-4-oxochroman-3-ylmethyl)phenyl]methanesulfonamide To a stirred solution of 6.8 g (0.022 mole) of the product of Example 111 and 6.8 mL (5.0 g, 0.049 mole) triethylamine in 300 mL dichloromethane at 0° C. was added 8.3 mL (13.9 g, 0.049 mole) triflic anhydride dropwise. The mixture was stirred at 0° C. for 1 hour, then concentrated, and dissolved in 50 mL methanol and 22 mL (0.110 mole) 5N NaOH was added. The mixture was stirred at room temperature for 1 hour, poured into water, acidified to ph 1–4 with 1N HCl, and extracted with ethyl acetate. The ethyl acetate extract was and washed with water and brine and then dried ($MgSO_4$) and concentrated to give an oil. Flash chromatography on silica gel eluting with 2.5% methanol in dichloromethane yielded an oil. Trituration with ether in hexanes afforded 7.0 g (72%) of the title product as a solid. Mp 128°–130° C. Analysis calculated for $C_{20}H_{20}NSO_5F_3$: C, 54.17; H, 4.55; N, 3.16. Found: C, 54.61; H, 4.41; N, 3.42.

EXAMPLE 113

C,C,C-Trifluoro-N-[3-(6-hydroxy-2,2-dimethyl-4-oxochroman-3-ylmethyl)phenyl]methanesulfonamide A mixture of 7.0 g (0.016 mole) of the product of Example 112 in 20 mL 48% hydrobromic acid and 20 mL glacial acetic acid was refluxed for 3 hours. The mixture was poured into water and extracted with ethyl acetate. The ethyl acetate extract was, washed with water and brine and then dried ($MgSO_4$) and concentrated to give an oil. Flash chromatography on silica gel eluting with 5% methanol in dichloromethane gave 6.9 g (100% of the title product as an oil). NMR ($CDCl_3$): $\delta 1.46$ (d, 6H); 2.85 (m, 1H); 2.95 (m, 2H). MS (Cl, $NH_3$) m/e: 447 ($M^+$+18, 100), 430 ($M^+$+1).

EXAMPLE 114

N-{3-[6-(5,6-Difluorobenzothiazol-2-ylmethoxy)-2,2-dimethyl-4-oxochroman-3-ylmethyl]phenyl}-C,C,C-trifluoromethane sulfonamide To a stirred solution of 6.9 g ((0.016 mole) of the product of Example 113 in 60 mL dimethylformamide was added 7.8 g (0.056 mole) potassium carbonate. The mixture was stirred at room temperature for 30 minutes, then 4.6 g (0.021 mole) 2-(chloromethyl)-5,6difluorobenzothiazole was added. The mixture was stirred at room temperature for 48 hours, poured into water, acidified to ph 1–4 with 1N HCl and then extracted with ethyl acetate. The ethyl acetate extract was, washed with water and brine and then dried ($MgSO_4$), and concentrated to give an oil. Flash chromatography on silica gel eluting with 2.5% methanol in dichloromethane yielded 6.7 g (68%) of the title product as a foam. NMR ($CDCl_3$): $\delta 1.43$ (s, 3H); 1.47 (s, 3H); 2.95 (m, 3H); 5.39 (s, 2H). MS (Cl, $NH_3$) m/e: 613 ($M^+$+1), 447, 315, 298, 265 (100).

EXAMPLE 115

(±)-N-{3-[6-5,6-Difluorobenzothiazol-2-ylmethoxy)-cis-4-hydroxy-2,2-dimethylchroman-3-yl]-phenyl}C,C,C-trifluoromethanesulfonamide To a stirred solution of 6.5 g (0.016) mole of the product of Example 114 and 4.36 g (0.0117 mole) cerium (111) chloride heptahydrate in 50 mL methanol and 50 mL tetrahydrofuran at −50° C. was added 440 mg (0.117 mole) sodium borohydride. The mixture was slowly warmed to 0° C. then quenched with 10 mL 10% ammonium chloride. The mixture was concentrated, poured into water, acidified to ph 1–4 with 1N HCl, and extracted with ethyl acetate. The ethyl acetate extract was, washed with water and brine and then dried ($MgSO_4$) and concentrated to give an oil. Flash chromatography on silica gel eluting 2.5% methanol in dichloromethane gave 1.61 g (25%) of the title product as a solid. NMR ($CDCl_3$): $\delta 1.38$ (s, 3H); 1.50 (s, 3H); 2.15 (m, 1H); 2.90 (m, 2H); 4.29 (s, br, 1H); 5.30 (s, 2H). MS (Cl, $NH_3$) m/e: 615 ($M^+$+1), 414, 282 (100).

EXAMPLE 116

(+)-N-2-tert-Butoxycarbonylamino-3-(1H-indol-3-yl)-propionic acid 6-(5,6-difluorobenzothiazol-2-ylmethoxy)-2,2-dimethyl-3-[3-trifluoromethanesulfonylamino)benzyl]-cis-chroman-4-yl ester This compound was prepared (68%) by the method in Example 9.

NMR (CDCl$_3$: δ1.46 (s, 9H); 1.54 (s, 3H); 1.64 (s, 3H); 2.50 (m, 1H); 2.75 (t, 1H); 3.10 (dd, 1H); 3.30 (ddd, 1H); 4.70 (m, 1H); 5.10 (d, 1H); 5.20 (dq, 2H); 5.40 (d, 1H); 6.40 (d, 1H).

EXAMPLE 117

(−)-N-2-tert-Butoxycarbonylamino-3-(1H-indol-3-yl)-propionic acid 6-(5,6-difluorobenzothiazol-2-ylmethoxy)-2,2-dimethyl-3-[3-trifluoromethanesulfonylamino)benzyl]-cis-chroman-4-yl ester This compound was prepared (74%) by the method in Example 9.

NMR (CDCl$_3$): δ1.32 (s, 3H); 1.44 (s, 9H); 1.50 (s, 3H); 2.40 (m, 1H); 2.50 (t, 1H); 2.90 (dd, 1H); 3.30 (ddd, 1H); 4.50 (dt, 1H); 5.05 (d, 1H); 5.24 (s, 2H); 5.60 (d, 1H).

EXAMPLE 118

(+)-N-{3-[6-(5,6-Difluorobenzothiazol-2-ylmethoxy)-cis-4-hydroxy-2,2-dimethylchroman-3-yl]phenyl}-C,C,C-trifluoromethanesulfonamide This compound was prepared (84%) by the method in Example 12.

Mp 194°–196° C. [α]$_D$: =+46.7°, c=0.26 (CH$_3$OH).

EXAMPLE 119

(−)-N-{3-[6-(5,6-Difluorobenzothiazol-2-ylmethoxy)-cis-4-hydroxy-2,2-dimethylchroman-3-yl]phenyl}-C,C,C-trifluoromethanesulfonamide This compound was prepared (43%) by the method in Example 13.

Mp 191°–193° C. [α]$_D$: =−42.0°, c=0.40 (CH$_3$OH).

EXAMPLE 120

1-(2-Benzyloxy-5-methoxyphenyl)-3-(3-nitrophenyl)-prop-2-en-1-one

To a stirred solution of 13.5 g (0.053 mole) of 5-methoxy-2-benzyloxyacetophenone in 100 ml absolute methanol at ambient temperature was added 2.84 g (0.053 mole) sodium methoxide. After 20 minutes, 8.0 g (0.053 mole) 3-nitrobenzaldehyde was added and the reaction mixture was stirred at ambient temperature for 18 hours. The resulting precipitate was filtered, washed with absolute methanol and then dried in vacuo to afford 20.2 g (98%) the title product as a solid, mp 108°–110° C. Analysis calculated for C$_{23}$H$_{19}$NO$_3$: C, 70.94; H, 4.92; N, 3.60. Found: C, 71.07; H, 4.47; N, 3.46.

EXAMPLE 121

3-(3-Aminophenyl)-1-(2-hydroxy-5-methoxyphenyl)-propan-1-one

A mixture of 15.0 g (0.039 mole) of the title product from Example 120 and 1.5 g 5% palladium on charcoal in 300 ml tetrahydrofuran and 200 ml absolute methanol was shaken in a Parr hydrogenator under 10 psi hydrogen at ambient temperature for 3 hours. The reaction mixture was filtered through Celite and the filtrate was evaporated in vacuo to yield an oil. Column chromatography of the oil on silica gel eluting with ethyl acetate: hexanes (1:2, v/v) gave 9.42 g (90%) of the title product as an oil; $^1$H NMR (CDCl$_3$): δ2.98 (t, J=8 Hz, 2H); 3.28 (t, J=8 Hz, 2H); 3.65 (s, br, 2H); 3.77 (s, 3H); 6.65 (m, 3H); 6.93 (d, J=9 Hz, 1H); 7.10 (m, 3H); 11.95 (s, 1H). Analysis calculated for C$_{16}$H$_{17}$NO$_3$: C, 70.83; H, 6.32; N, 5.16. Found: C, 70.51; H, 6.30; N, 4.97.

EXAMPLE 122

Acetic acid 4-methoxy-2-[3-(3-nitrophenyl)-propionyl]phenyl ester

To a stirred solution of 16.5 g (0.061 mole) product from Example 121, 43 ml (0.305 mole) triethylamine and 0.7 g (0.006 mole) dimethylaminopyridine in 200 ml methylene chloride at 0° was added dropwise 10.8 ml (0.152 mole) acetyl chloride. The reaction mixture was allowed to warm to ambient temperature over 1 hour, then the volume was reduced in vacuo. The concentrate was diluted with ethyl acetate and washed successively with 1N hydrochloric acid, water and brine and then dried (magnesium sulfate) and evaporated in vacuo to give an oil. Column chromatography of the oil on silica gel eluting with methanol:methylene chloride (1:40, v/v) afforded 19.0 g (88%) the title product as an oil; $^1$H NMR (CDCl$_3$): δ2.13 (s, 3H); 2.27 (s, 3H); 2.97 (t, J=7 Hz, 2H); 3.17 (t, J=8 Hz, 2H); 3.80 (s, 3H); 6.94 (d, J=8 Hz, 1H); 702 (s, 2H); 7.25 (m, 3H); 7.38 (d, J=8 Hz, 1H); 7.46 (s, br, 1H). Analysis calculated for C$_{20}$H$_{21}$NO$_5$: C, 67.59; H, 5.96; N, 3.94. Found: C, 67.28; H, 5.83; N, 3.54.

EXAMPLE 123

N-[3-(6-Methoxy-2-methyl-4-oxo-4H-chroman-3-ylmethyl)-phenyl]acetamide

To a stirred suspension of 3.8 g (0.095 mole) 60% sodium hydride in 50 ml dimethylsulfoxide at 20° was added, dropwise, a solution of 9.6 g (0.027 mole) of the product from Example 122 in 100 mL dimethylsulfoxide. The reaction mixture was stirred at 20° for 1 hour, then slowly poured into a slurry of ice in an oxalic acid solution. The aqueous mixture was extracted with ethyl acetate which in turn was successively washed with water and brine and then dried (magnesium sulfate) and evaporated in vacuo to afford an oil. The oil was dissolved in 50 ml glacial acetic acid and 1 ml hydrochloric acid and then refluxed for 30 minutes. The reaction mixture was poured into water and then extracted with ethyl acetate. The ethyl acetate extract was successively washed with water and brine and then dried (magnesium sulfate) and evaporated in vacuo to afford an oil. Column chromatography of the oil on silica gel eluting with methanol:methylene chloride (1:40 v/v) yielded 7.7 g (85%) the title product as a solid, mp 176°–178° C.

Analysis calculated for C$_{20}$H$_{19}$NO$_4$: C, 71.20; H, 5.68; N, 4.15. Found: C, 71.22; H, 5.48; N, 4.22.

EXAMPLE 124

3-(3-Aminobenzyl)-6-methoxy-2-methylchroman-4-one

A mixture of 2.78 g (8.23 mmole) product from Example 123, 20 mL hydrochloric acid, 20 mL water, and 20 mL methanol was refluxed for 2 hours. The mixture was poured into water, basified, and extracted with ethyl acetate. The ethyl acetate extract was washed with water and brine and then dried (MgSO$_4$) and concentrated to give a solid. Flash chromatography on silica gel eluting with 2.5% methanol/ dichloromethane gave 2.19 g (90%) the title product as a solid, mp 110°–112° C. Analysis calculated for $C_{18}H_{17}NO_3$: C, 73.20; H, 5.80; N, 4.74. Found: C, 73.33; H, 5.27; N, 4.76.

EXAMPLE 125

C,C,C-Trifluoro-N-[3-(6-methoxy-2-methyl-4-oxo-4H-chromen-3-ylmethyl)phenyl] methanesulfonamide To a stirred solution of 2.15 g (7.27 mmole) of the product from Example 124 and 2.1 mL (15.3 mmole) triethylamine in 50 mL dichloromethane at 0° C. was added dropwise 2.6 mL (15.3 mmole) triflic anhydride. The mixture was stirred at 0° C. for 1 hour, concentrated, then dissolved in 50 mL methanol and 18 mL (38.3 mmole) 2N sodium hydroxide was added. The mixture was stirred at room temperature for 1 hour, poured into water, acidified to ph 1–4 with 1N HCl, then extracted with ethyl acetate. The ethyl acetate extracts was washed with water and brine and dried (MgSO$_4$), and concentrated to give an oil. Flash chromatography on silica gel eluting with 30% ethyl acetate in hexanes yielded 2.19 g (70%) the title product as a solid, mp 172°–174° C. Analysis calculated for $C_{19}H_{16}NO_5SF_3$: C, 53.40; H, 3.77; N, 3.28. Found: C, 53.29; H, 3.60; N, 2.95.

EXAMPLE 126

C,C,C-Trifluoro-N-[3-(6-hydroxy-2-methyl-4-oxo-4H-chromen-3-yl-methyl)phenyl] methanesulfonamide A mixture of 2.1 g (4.91 mmole) of the product from Example 125, 25 mL 48% hydrobromic acid and 25 mL glacial acetic acid was refluxed for 18 hours. The mixture was poured into a stirred slurry of ice and water and stirred for 1 hour. The mixture was filtered, and the filtrant washed with water and dried to give a solid. Flash chromatography on silica gel eluting with 5% methanol in dichloromethane afforded 1.89 g (93%) the title product as a solid, mp 232°–234° C.

Analysis calculated for $C_{18}H_{14}NO_5SF_3$: C, 52.30; H, 3.41; N, 3.39. Found: C, 52.12; H, 3.23; N, 3.10.

EXAMPLE 127

C,C,C-Trifluoro-N-{3-[6-(5-fluorobenzothiazol-2-ylmethoxy)-2-methyl-4-oxo-4H-chromen-3-ylmethyl]phenyl}methanesulfonamide To a stirred solution of 1.8 g (4.4 mmole) of the product from Example 126 in 50 mL dimethylformamide was added 2.4 g (17.4 mmole) potassium carbonate. The mixture was stirred at room temperature for 1 hour then 1.2 g (5.72 mmole) 2-(chloromethyl)-5-fluorobenzothiazole was added. The mixture was stirred for 18 hours, poured into water, acidified to ph 1–4 with 1N HCl, and extracted with ethyl acetate. The ethyl acetate extract was washed with water and brine and then dried (MgSO$_4$), and concentrated to give a solid. Trituration with ether afforded 2.45 g (97%) of the title product as a solid, mp 218°–220° C. Analysis calculated for $C_{26}H_{18}N_2S_2O_5F_4$: C, 53.98; H, 3.14; N, 4.84. Found: C, 53.94; H, 2.91; N, 4.55.

EXAMPLE 128

(±)-C,C,C-Trifluoro-N-{3-[6-(5-fluorobenzothiazol-2-ylmethoxy)-trans-2-methyl-4-oxochroman-3-ylmethyl]phenyl}methanesulfonamide To a stirred suspension of 2.59 g (4.48 mmole) product from Example 127 in 100 mL tetrahydrofuran was added dropwise 9 mL (9.40 mmole) LiB(sec-butyl)$_3$H (1M in THF, L-Selectride®) at –78° C. The mixture was stirred for 2 hours, then quenched with 5% ammonium chloride. The mixture was poured into water, acidified to ph 1–4 with 1N HCl, and extracted with ethyl acetate. The ethyl acetate extract was washed with water and brine and dried (MgSO$_4$) and concentrated to give an oil. Flash chromatography on silica gel eluting with 2.5% methanol in dichloromethane afforded 1.4 g (54%) of the title product as a solid, mp 183°–185° C. Analysis calculated for $C_{26}H_{20}N_2S_2O_5F_4$: C, 53.79; H, 3.47; N, 4.83. Found: C, 53.25; H, 3.23; N, 4.45.

EXAMPLE 129

(±)-Bis-C,C,C-trifluoro-N,N-{3-[6-(5-fluorobenzothiazol-2-ylmethoxy)-trans-2-methyl-4-oxochroman-3-ylmethyl] phenyl}methanesulfonamide To a stirred solution of 1.34 g (2.31 mmole) product from Example 128, and 0.4 mL (2.7 mmole) triethylamine in 50 mL dichloromethane at 0° C. was added 0.4 mL (2.5 mmole) triflic anhydride. The mixture was stirred at 0° C. for 2 hours, concentrated, diluted with ethyl acetate and washed with water and brine and then dried (MgSO$_4$) and concentrated to give an oil. Flash chromatography on silica gel eluting with 20% ethyl acetate in hexanes afforded 760 mg (46%) of the title product as a solid, mp 141°–143° C. NMR (CDCl$_3$): δ1.40 (d, 3H); 2.30 (m, 1H); 2.75 (9, 1H); 3.13 (d, 2H); 4.30 (dt, 1H); 5.45 (s, 2H). Analysis calculated for $C_{27}H_{19}N_2S_3O_7F_7$: C, 45.51; H, 2.69; N, 3.93. Found: C, 47.62; H, 2.76; N, 3.60.

EXAMPLE 130

(±)-Bis-C,C,C-trifluoro-N,N-{3-[6-(5-fluorobenzothiazol-2-ylmethoxy)-cis-4-hydroxy-trans-2-methylchroman-3-ylmethyl]phenyl}-methanesulfonamide To a stirred solution of 450 mg (1.05 mmole) product from Example 129 and 430 mg (1.16 mmole) cerium (111) chloride heptahydrate in 20 mL methanol and 20 mL tetrahydrofuran at –60° C. was added 44 mg (1.16 mmole) sodium borohydride. The mixture was stirred at –60° C. for 2 hours, then quenched with 5% ammonium chloride. The mixture was was poured into water and extracted with ethyl acetate. The ethyl acetate extract was washed with water and brine and then dried (MgSO$_4$) and concentrated to give an oil. Flash chromatography on silica gel eluting with 30% ethyl acetate in hexanes yielded 320 mg (43%) of the title product as an oil. NMR (CDCl$_3$): δ1.49 (d, 3H); 1.90 (m, 1H); 2.60 (m, 1H); 2.85 (d, 2H); 4.13 (m, 1H); 4.25 (m, 1H); 5.36 (s, 2H). MS (LSIMS) m/e: 715 (M$^+$, 100).

EXAMPLE 131

(–)-N-2-tert-Butoxycarbonylamino-3-(1H-indol-3-yl)-propionic acid 6-(5-fluorobenzothiazol-2-ylmethoxy)-2-trans-methyl-3-[3-bis (trifluoromethanesulfonylamino)benzyl]-chroman-4-cis-yl ester This compound was prepared from the product of Example 130 by the method in Example 9.

NMR (CDCl$_3$): δ1.44 (s, br, 12H); 2.15 (m, 1H); 2.35 (t, 1H); 2.85 (dd, 1H); 3.30 (ddd, 2H); 5.00 (d, 1H); 5.10 (m, 1H); 5.28 (s, 2H); 5.45 (d, 1H). MS (LSIMS) m/e: 869 (5, M$^+$–132), 565 (100, M$^+$–436).

EXAMPLE 132

(+)-N-2-tert-Butoxycarbonylamino-3-(1H-indol-3-yl)-propionic acid 6-(5-fluorobenzothiazol-2-ylmethoxy)-2-trans-methyl-3-[3-bis (trifluoromethanesulfonylamino)benzyl]-chroman-4-cis-yl ester This compound was prepared from the product of Example 130 by the method in Example 9.

NMR (CDCl$_3$): δ1.46 (s, 9H); 1.54 (d, 3H); 2.25 (m, 1H); 2.50 (t, 1H); 3.05 (dd, 1H); 3.25 (ddd, 2H); 4.20 (m, 1H); 4.65 (m, 1H); 5.00 (d, 1H); 5.10 (m, 1H); 5.20 (d, 1H); 5.25 (q, 1H). MS (LSIMS) m/e: 869 (5, M$^+$–132), 565 (100, M$^+$–436).

EXAMPLE 133

(+)-C,C,C-Trifluoro-N-{3-[6-(5-fluorobenzothiazol-2-ylmethoxy)-cis-4-hydroxy-trans-2-methylchroman-3-ylmethyl]-phenyl}methanesulfonamide This compound was prepared from the product of Example 132 by the method in Example 12.

Mp: 174°–176° C. [α]$_D$: +76.9°, c=0.2 (acetone)

EXAMPLE 134

(–)-C,C,C-Trifluoro-N-{3-[6-(5-fluorobenzothiazol-2-ylmethoxy)-cis-4-hydroxy-trans-2-methylchroman-3-ylmethyl] phenyl}methanesulfonamide This compound was prepared from the product of Example 130 by the method in Example 13.

Mp: 174°–176° C. [α]$_D$: –72.0°, c=0.2 (acetone)

EXAMPLE 135

(+)-N-{3-[6-(5,6-Difluorobenzothiazol-2-ylmethoxy)-cis-4-hydroxy-trans-2-methylchroman-3-ylmethyl] phenyl}-C,C,C-trifluoromethanesulfonamide sodium salt monohydrate This compound was prepared from the product of Example 126 by an analogous sequence which afforded the product in Example 123. The sodium salt was prepared according to the method in Example 94. Mp: 185°–188° C. (ethyl acetate in. hexanes). [α]$_D$: +79.2°, c=0.37 (methanol). Analysis calculated for $C_{26}H_{20}N_2O_5S_2F_5Na \cdot H_2O$: C, 48.78; H, 3.46; N, 4.37. Found: C, 47.60; H, 3.69; N, 394.

EXAMPLE 136

(+)-3-(6-Hydroxychroman-3-ylmethyl)benzoic acid methyl ester

A mixture of 5.0 g (0.017 mole) of (3R-cis)-3-(4,6-dihydroxychroman-3-ylmethyl)benzoic acid methyl ester (prepared by esterification of the corresponding carboxylic acid (prepared according to the method of co-pending U.S. Pat. Application of Murtiashaw, et al., U.S. Ser. No. 07/964, 336 filed Oct. 21, 1992) and 1.0 g palladium hydroxide in 100 mL glacial acetic acid was shaken in a Parr hydrogenator under 50 psi hydrogen at room temperature for 3 hours. The mixture was filtered through Celite and the filtrate concentrated to give an oil. Flash chromatography on silica gel eluting with 5% methanol in dichloromethane yielded 4.3 g (81% of the title product as an oil). NMR (CDCl$_3$): δ2.30 (m, 1H); 2.50 (dd, 1 ,H) ; 2.75 (m, 3H); 3.80 (dd, 1H); 3.92 (s, 3H); 4.15 (dd, 1H). MS (Cl, NH$_3$) m/e: 316 (100).

EXAMPLE 137

(+)-3-(6-Benzyloxychroman-3-ylmethyl)benzoic acid methyl ester

To a stirred suspension of 4.2 g (0.013 mole) of the product of Example 136 and 5.5 g (0.04 mole) potassium acetonate in 100 mL dimethylformamide was added 1.7 mL (0.015 mole) benzyl bromide. The mixture was stirred at room temperature for 3 days, poured into water and extracted with ethyl acetate. The ethyl acetate extract was washed with water and brine and dried (MgSO$_4$) and concentrated to give a solid. Recrystallization from ethyl acetate in hexanes yielded 4.9 g (88%) of the title product as a solid. [α]$_D$: 45.8°, c=0.9 (chloroform). NMR (CDCl$_3$): δ2.35 (m, 1H); 2.50 (dd, 1H); 2.75 (m, 3H); 3.80 (dd, 1H); 3.95 (s, 3H); 4.15 (dd, 1H); 5.00 (s, 2H).

EXAMPLE 138

(+)-3-(6-Benzyloxychroman-3-ylmethyl)benzoic acid

A mixture of 4.8 g (12.4 mmole) of the product of Example 127 and 25 mL (0.124 mole) 5N NaOH in 100 mL methanol and 20 mL tetrahydrofuran was refluxed for 1 hour. The mixture was concentrated, poured into water, acidified to ph 1–4 with 1N HCl, and extracted with ethyl acetate. The ethyl acetate extract was washed with water and brine and added (MgSO$_4$) and concentrated to afford a solid. Recrystallization from ethyl acetate in hexanes gave 4.46 g, of the title product mp 128°–130°. [α]$_D$: +47.71°, c=0.35 (chloroform). Analysis calculated for $C_{24}H_{22}O_4$: C, 76.99; H, 5.92. Found: C, 75.97; H, 5.60.

EXAMPLE 139

(+)-N-3-(6-Benzyloxychroman-3-ylmethyl) carbobenzyloxyphenylamine

A mixture of 3.92 g (0.010 mole) of the product from Example 138, 1.4 mL (0.013 mole) benzyl alcohol, 3.5 mL triethylamine (0.025 mole) and 2.4 mL (0.011 mole) diphenylphosphoryl azide in 50 mL dioxane was refluxed for 2 hours. The mixture was poured into water, and extracted with ethyl acetate. The ethyl acetate extract was then washed successively with 1N hydrochloric acid, 1N potassium hydroxide, water and brine, then dried (MgSO$_4$) and concentrated to yield a solid. Flash chromatography on silica gel eluting with 20% ethyl acetate in hexanes gave 4.46 g (93%) of the title product as a solid, mp 106°–108° C. [α]$_D$: +36.3°, c=0.35 (chloroform). Analysis calculated for $C_{31}H_{29}NO_4$: C, 77.64; H, 6.09; N, 2.92. Found: C, 77.11; H, 5.88; N, 3.09.

EXAMPLE 140

(+)-3-(3-Aminobenzyl)chroman-6-ol

A mixture 4.9 g (10.21 mmole) of the product from Example 139 and 0.5 g palladium hydroxide in 50 mL methanol and 50 mL tetrahydrofuran was shaken in a Parr hydrogenator under 50 psi hydrogen for 3 hours. The mixture was filtered through Celite and concentrated to give a solid. Trituration with ether yielded 2.41 g (92%) of the title product as a solid, mp 162°–164° C. Analysis calculated for $C_{16}H_{17}NO_2$: C, 75.27; H, 6.71; N, 5.49. Found: C, 74.50; H, 6.51; N, 5.73.

EXAMPLE 141

(+)-3-[6-(7-Chloroquinolin-2-ylmethoxy)chroman-3-ylmethyl]phenylamine

To a stirred solution of 350 mg (1.37 mmole) of the product from Example 140 in 10 mL dimethylformamide at 0° C. was added 60 mg (1.51 mmole) sodium hydride. The mixture was stirred at 0° C. for 30 minutes, then 349 mg (1.64 mmole) 2-(chloromethyl)-7-chloroquinoline was added. The mixture was warmed to room temperature and stirred for 72 hours. The mixture was poured into water and extracted with ethyl acetate. The ethyl acetate extract was washed with water and brine, dried (MgSO$_4$) and concentrated to give an oil. Flash chromatography on silica gel eluting with 40% ethyl acetate in hexanes yielded 476 mg (81%) of the title product as a solid, mp 128°–130° C. Analysis calculated for $C_{26}H_{23}N_2O_2Cl$: C, 72.47; H, 5.38; N, 650. Found: C, 72.47; H, 5.12; N, 6.43.

EXAMPLE 142

(+)-N-{3-[6-(7-Chloroquinotin-2-ylmethoxy)chroman-3-ylmethyl]phenyl}-C,C,C-trifluoromethanesulfonamide sodium salt monohydrate To a stirred solution of 455 mg (0.947 mmole) of the product from Example 141 and 0.3 mL triethylamine (2.40 mmole) in 15 mL dichloromethane at 0° C. was added 0.2 mL (1.18 mmole) triflic anhydride. The mixture was stirred at 0° C. for 1 hour, then concentrated to give a foam which was dissolved in 15 mL methanol and 1 mL tetrahydrofuran. The solution was cooled to ° C. and 3 mL 2N sodium hydroxide was added. The mixture was poured into water, acidified to ph 1–4 with 1N HCl, and extracted with ethyl acetate. The ethyl acetate extract was and washed with water and brine, dried (MgSO$_4$) and concentrated to give an oil. Flash chromatography on silica gel eluting with 35% ethyl acetate in hexanes afforded 515 mg (97%) solid. Recrystallization from ethyl acetate in hexanes yielded 464 mg solid, mp 178°–180° C. This solid was dissolved in 10 mL methanol and 0.8 mL 1.0N sodium hydroxide was added. The mixture was stirred at room temperature for 2 hours, concentrated, dried and then recrystallized from ethyl acetate in hexanes to afford 455 mg of the title product as a solid, mp 120°–123° C. [α]$_D$: +43.10°, c=0.32 (methanol). Analysis calculated for $C_{27}H_{21}N_2O_4SClF_3Na \cdot H_2O$: C, 53.78; H, 3.84; N, 4.65. Found: C, 54.40; H, 3.67; N, 4.19.

EXAMPLE 143

(+)-N-{3-[6-(5,6-Difluorobenzothiazol-2-ylmethoxy)chroman-3-ylmethyl]phenyl}-C,C,C-trifluoromethanesulfonamide sodium salt This compound was prepared from the product of Example 140 by the same sequence which afforded the product in Example 142, mp 137°–140° C. (ethyl acetate in hexanes). [α]$_D$: +38.8, c=0.35 (methanol). Analysis calculated for $C_{25}H_{19}N_2S_2O_4F_5Na$: C, 50.68; H, 3.06; N, 4.73. Found: C, 50.17; H, 3.41; N, 4.05.

I claim:

1. A racemic or optically active compound of the formula

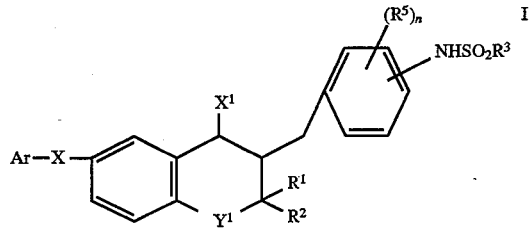

wherein

Y$^1$ is selected from the group consisting of a O, S, SO and SO$_2$;

X$^1$ is hydrogen or hydroxyl;

Ar is an optionally substituted 5–8-membered heteroaryl or optionally substituted benzene fused optionally substituted heteroaryl ring wherein said heteroaryl ring comprises 1 to 4 heteroatoms selected from nitrogen, oxygen and sulfur wherein said substituents are selected from the group consisting of halo, (C$_1$–C$_6$) alkyl wherein said alkyl groups may be straight chained, branched or cyclic or a combination thereof, optionally substituted aryl or cycloheteroaryl wherein said alky;

X is selected from the group consisting of CH$_2$O, CH$_2$—CH$_2$, CH=CH, C≡C, CH$_2$S, CH$_2$SO$_2$ and CH$_2$SO;

R$^1$ and R$^2$ are each independently selected from hydrogen, halo, optionally substituted (C$_1$–C$_6$)alkyl and halo(C$_1$–C$_6$)alkyl or R$^1$ and R$^2$ together with the carbon to which they are attached form a 3–6 membered cycloalkyl or cycloheteroalkyl ring;

R$^3$ is selected from the group consisting of optionally substituted (C$_3$–C$_6$) cycloalkyl-(C$_1$–C$_6$)alkyl, optionally halogenated (C$_1$–C$_6$)alkyl, optionally halogenated (C$_3$–C$_6$) cycloalkyl and optionally substituted aryl wherein said substituents are selected from the group consisting of optionally halogenated (C$_1$–C$_6$)alkyl, halogen, nitro, carboxyl, N-disubstituted carboxamide, and (C$_1$–C$_6$)alkoxy;

R$^5$ is selected from the group consisting of hydroxyl, (C$_1$–C$_6$)alkoxy, (C$_1$–C$_6$)alkyl, halo(C$_1$–C$_6$)alkyl and (C$_3$–C$_8$)cycloalkyl wherein the alkyl groups of said alkyl, alkoxy and cycloalkyl residues may be straight chained, branched or cyclic or a combination thereof, and halogen; and R$^6$ is hydrogen or (C$_1$–C$_4$)alkyl;

and n is 0 or an integer between 1 and 4;

and pharmaceutically acceptable salts and prodrugs thereof.

2. The compound of claim 1 selected from the cis-racemic mixture and the cis-(+) and cis-(–) enantiomers.

3. The compound of claim 2 wherein X is CH$_2$O and Y$^1$ is oxygen and Ar, X$^1$, n, R$^1$, R$^2$, R$^3$ and R$^5$ are defined as in claim 1.

4. The compound of claim 3 wherein R$^1$ is hydrogen or optionally substituted (C$_1$–C$_6$)alkyl and R$^2$ is optionally substituted (C$_1$–C$_6$)alkyl.

5. The compound of claim 4 wherein R$^1$ and R$^2$ are each methyl or R$^1$ is hydrogen and R$^2$ is trans-methyl.

6. The compound of claim 3 wherein R$^5$ is selected from optionally substituted (C$_1$–C$_6$)alkyl, (C$_1$–C$_6$)alkoxy and halo when n is not equal to 0.

7. The compound of claim 2 wherein X$^1$ is hydrogen and X, Y$^1$, Ar, R$^1$, R$^2$, R$^3$, R$^5$ and n are as defined in claim 1.

8. The compound of claim 7 wherein n is 0.

9. The compound of claim 1 selected from:

cis-(±)-N-[3-(6-(5-fluorobenzothiazol-2ylmethoxy)-4-hydroxy-chroman-3-ylmethyl)phenyl]trifluoromethanesulfonamide;

cis-(+)-N-[3-(6-(5-fluorobenzothiazol-2ylmethoxy)-4-hydroxy-chroman-3-ylmethyl)phenyl]trifluoromethanesulfonamide;

cis-(−)-N-[3-(6-(5-fluorobenzothiazol-2ylmethoxy)-4-hydroxy-chroman-3-ylmethyl)-phenyl]trifluoromethanesulfonamide;

cis-(±)-N-(3-[6-(5,6-difluorobenzothiazol-2-ylmethoxy)-4-hydroxy-chroman-3-ylmethyl)-phenyl]-trifluoromethanesulfonamide;

cis-(+)-N-[3-(6-(5,6-difluorobenzothiazol-2ylmethoxy)-4-hydroxy-chroman-3-ylmethyl)phenyl]trifluoromethanesulfonamide;

cis-(−)-N-[3-(6-(5,6-difluorobenzothiazol-2ylmethoxy)-4-hydroxy-chroman-3-ylmethyl)phenyl]trifluoromethanesulfonamide;

cis-(±)-N-[3-(6-(7-chloroquinolin-2ylmethoxy)-4-hydroxy-chroman-3-ylmethyl)phenyl]trifluoromethanesulfonamide;

cis-(+)-N-[3-(6-(7-chloroquinolin-2ylmethoxy)-4-hydroxy-chroman-3-ylmethyl)phenyl]trifluoromethanesulfonamide;

cis-(−)-N-[3-(6-(7-chloroquinolin-2ylmethoxy)-4-hydroxy-chroman-3-ylmethyl)phenyl]trifluoromethanesulfonamide;

cis-(±)-N-[3-(6-(4-isopropylthiazol-2-ylmethoxy)-4-hydroxy-chroman-3-ylmethyl)phenyl]trifluoromethansulfonamide;

cis-(+)-N-[3-(6-(4-isopropylthiazol-2-ylmethoxy)-4-hydroxy-chroman-3-ylmethyl)phenyl]trifluoromethansulfonamide;

cis-(−)-N-[3-(6-(4-isopropylthiazol-2-ylmethoxy)-4-hydroxy-chroman-3-ylmethyl)phenyl]trifluoromethansulfonamide;

cis-(±)-N-[3-(6-(4-cyclobutylthiazol-2-ylmethoxy)-4-hydroxy-chroman-3-ylmethyl)phenyl]trifluoromethansulfonamide;

cis-(+)-N-[3-(6-(4-cyclobutylthiazol-2-ylmethoxy)-4-hydroxy-chroman-3-ylmethyl)phenyl]trifluoromethansulfonamide;

cis-(−)-N-[3-(6-(4-cyclobutylthiazol-2-ylmethoxy)-4-hydroxy-chroman-3-ylmethyl)phenyl]trifluoromethansulfonamide;

cis-(±)-N-(3-[6-(6-fluoroquinolin-2-ylmethoxy)-4-hydroxy-chroman-3-ylmethyl)phenyl]-trifluoromethanesulfonamide;

cis-(+)-N-(3-[6-(6-fluoroquinolin-2-ylmethoxy)-4-hydroxy-chroman-3-ylmethyl)phenyl]-trifluommethanesulfonamide;

cis-(−)-N-(3-[6-(6-fluoroquinolin-2-ylmethoxy)-4-hydroxy-chroman-3-ylmethyl)phenyl]-trifluommethanesulfonamide;

cis-(±)-N-(3-[6-(quinolin-2-ylmethoxy)-4-hydroxy-chroman-3-ylmethyl)-phenyl]trifluoromethanesulfonamide;

cis-(+)-N-(3-[6-(quinolin-2-ylmethoxy)-4-hydroxy-chroman-3-ylmethyl)-phenyl]trifluoromethanesulfonamide;

cis-(−)-N-(3-[6-(quinolin-2-ylmethoxy)-4-hydroxy-chroman-3-ylmethyl)-phenyl]trifluoromethanesulfonamide;

cis-(±)-C,C,C-Trifluoro-N,N-{3-[6-(5-fluorobenzothiazol-2-ylmethoxy)-4-hydroxy-trans-2-methylchroman-3-ylmethyl]phenyl}-methanesulfonamide;

cis-(+)-C,C,C-Trifluoro-N-{3-[6-(5-fluorobenzothiazol-2-ylmethoxy)-4-hydroxy-trans-2-methylchroman-3-ylmethyl]-phenyl}methanesulfonamide;

cis-(−)-C,C,C-Trifluoro-N-{3-[6-(5-fluorobenzothiazol-2-ylmethoxy)-4-hydroxy-trans-2-methylchroman-3-ylmethyl]phenyl}methanesulfonamide;

cis-(+)-N-{3-[6-(7-Chloroqinolin-2-ylmethoxy)-4-hydroxychroman-3-ylmethyl]-4-methoxyphenyl}-C,C,C-trifluoromethanesulfonamide;

cis-(−)-N-{3-[6-(7-Chloroqinolin-2-ylmethoxy)-4-hydroxychroman-3-ylmethyl]-4-methoxyphenyl}-C,C,C-trifluoromethanesulfonamide;

cis-(+)-N-{3-[6-(5,6-Difluorobenzothiazol-2-ylmethoxy)-4-hydroxychroman-3-ylmethyl]-4-methoxyphenyl}-C,C,C-trifluoromethanesulfonamide;

cis-(+)-N-{3-[6-(5,6-Difluorobenzothiazol-2-ylmethoxy)-4-hydroxychroman-3-ylmethyl]-4-methoxyphenyl}-C,C,C-trifluoromethanesulfonamide;

cis-(+)-N-{3-[6-(4-Cyclobutylthiazol-2-ylmethoxy)-4-hydroxychroman-3-ylmethyl]-4-methoxyphenyl}-C,C,C-trifluoromethanesulfonamide;

cis-(−)-N-{3-[7-(5,6-Difluorobenzothiazol-2-ylmethoxy)-1-hydroxy-1,2,3,4-tetrahydronapth-2-ylmethyl]-phenyl}-C,C,C-trifluoromethanesulfonamide;

cis-N-{3-[6-(7-Chloroquinolin-2-ylmethoxy)-chroman-3-ylmethyl]-phenyl}-C,C,C-trifluoromethanesulfonamide;

cis-(±)-N-{4-Chloro-3-[6-(7-chloroqinolin-2-ylmethoxy)-4-hydroxychroman-3-ylmethyl]-phenyl}-C,C,C-trifluoromethanesulfonamide;

cis-(+)-N-{4-Chloro-3-[6-(7-chloroqinolin-2-ylmethoxy)-4-hydroxychroman-3-ylmethyl]-phenyl}-C,C,C-trifluoromethanesulfonamide;

cis-(±)-N-{4-Chloro-3-[6-(5,6-difluorobenzothiazol-2-ylmethoxy)-4-hydroxychroman-3-yl-methyl]phenyl}-C,C,C-trifluoromethanesulfonamide;

cis-N-{3-[6-(5,6-Difluorobenzothiazol-2-ylmethoxy)-4-hydroxy-trans-2-methylchroman-3-ylmethyl]-phenyl}-C,C,C-trifluoromethanesulfonamide;

cis-(±)-N-{3-[6-(5,6-Difluorobenzothiazol-2-ylmethoxy)-4-hydroxy-2,2-dimethylchroman-3-yl]-phenyl}C,C,C-trifluoromethanesulfonamide;

cis-(+)-N-{3-[6-(5,6-Difluorobenzothiazol-2-ylmethoxy)-4-hydroxy-2,2-dimethylchroman-3-yl]phenyl}-C,C,C-trifluoromethanesulfonamide;

cis-(−)-N-{3-[6-(5,6-Difluorobenzothiazol-2-ylmethoxy)-4-hydroxy-2,2-dimethylchroman-3-yl]phenyl}-C,C,C-trifluoromethanesulfonamide;

cis-(+)-N-{4-Chloro-3-[6-(5,6-difluorobenzothiazol-2-ylmethoxy)-4-hydroxychroman-3-yl-methyl]phenyl}-C,C,C-trifluoromethanesulfonamide;

cis-(−)-N-{4-Chloro-3-[6-(5,6-difluorobenzothiazol-2-ylmethoxy)-4-hydroxychroman-3-yl-methyl]phenyl}-C,C,C-trifluoromethanesulfonamide;

cis-(+)-N-{4-Chloro-3-[6-(5,6-difluorobenzothiazol-2-ylmethoxy)-4-hydroxy-2,2-dimethyl-chroman-3-ylmethyl]-phenyl}-C,C,C-trifluoromethanesulfonamide;

cis-N-{3-[6-(5,6-Difluorobenzothiazol-2-ylmethoxy)-2,2-dimethyl-2H-chromen-3-ylmethyl]-4-methoxyphenyl}-C,C,C-trifluoromethanesulfonamide;

cis-N-{3-[6-(7-Chloroqinolin-2-ylmethoxy)-4-hydroxy-chorman-3-ylmethyl]-4-methoxyphenyl}-C,C,C-trifluoromethanesulfonamide;

cis-(±)-N-{3-[6-(5,6-Difluorobenzothiazol-2-ylmethoxy)-4-hydroxy-2,2-dimethylchroman-3-ylmethyl]-4-methoxyphenyl}-C,C,C-trifluoromethanesulfonamide;

cis(+)-N-{3-[6-(5,6-Difluorobenzothiazol-2-ylmethoxy)-4-hydroxy-2,2-dimethylchroman-3-ylmethyl]-4-methoxyphenyl}-C,C,C-trifluoromethanesulfonamide;

cis-N-{3-[6-(7-Chloroqinolin-2-ylmethoxy)-4-hydroxychroman-3-ylmethyl]-4-hydroxyphenyl}-C,C,C-trifluoromethanesulfonamide;

cis-N-{3-[6-(7-Chloroquinolin-2-ylmethoxy)-4-hydroxychroman-3-ylmethyl]-4-hydroxyphenyl}-C,C,C-trifluoromethanesulfonamide;

cis-N-{3-[6-(5,6-Difluorobenzothiazol-2-ylmethoxy)-4-hydroxychroman-3-ylmethyl]-4-methoxyphenyl}-C,C,C-trifluoromethanesulfonamide;

cis-N-{3-[6-(5,6-Difluorobenzothiazol-2-ylmethoxy)-4-hydroxy-2,2-dimethylchroman-3-ylmethyl]-4-methoxyphenyl}-C,C,C-trifluoromethanesulfonamide; and 3-[6-(5,6-Difluorobenzothiazol-2-ylmethoxy)-4-hydroxy-2,2-dimethylchroman-3-ylmethyl]-4-methoxybenzoic acid.

10. A pharmaceutical composition for the treatment of a condition, in a mammal, selected from asthma, arthritis, psoriasis, ulcers and myocardial infarction comprising an amount of a compound according to claim 1 effective to treat said condition and pharmaceutically acceptable carrier.

11. A method for the treatment of a condition, in a mammal, selected from asthma, arthritis, psoriasis, ulcers and myocardial infarction in a subject in need of such treatment comprising administering to said mammal an asthma, arthritis, psoriasis, ulcers and myocardial infarction treating mount of a compound according to claim 1.

* * * * *